United States Patent
Sellman et al.

(10) Patent No.: US 9,879,070 B2
(45) Date of Patent: Jan. 30, 2018

(54) **ANTIBODIES TO *S. AUREUS* SURFACE DETERMINANTS**

(71) Applicant: MEDIMMUNE, LLC, Gaithersburg, MD (US)

(72) Inventors: Brett Sellman, Gaithersburg, MD (US); Christine Tkaczyk, Gaithersburg, MD (US); Partha S. Chowdhury, Gaithersburg, MD (US); Lei Hua, Gaithersburg, MD (US); Peter Pavlik, Gaithersburg, MD (US); Rebecca Buonpane, Gaithersburg, MD (US); Chew-Shun Chang, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/440,748

(22) PCT Filed: Nov. 6, 2013

(86) PCT No.: PCT/US2013/068624
§ 371 (c)(1),
(2) Date: May 5, 2015

(87) PCT Pub. No.: WO2014/074540
PCT Pub. Date: May 15, 2014

(65) Prior Publication Data
US 2015/0291685 A1    Oct. 15, 2015

Related U.S. Application Data

(60) Provisional application No. 61/723,137, filed on Nov. 6, 2012, provisional application No. 61/782,405, filed on Mar. 14, 2013.

(51) Int. Cl.
| | |
|---|---|
| *C07K 16/12* | (2006.01) |
| *G01N 33/569* | (2006.01) |
| *A61K 39/40* | (2006.01) |
| *A61K 45/06* | (2006.01) |
| *A61K 39/00* | (2006.01) |

(52) U.S. Cl.
CPC .......... *C07K 16/1271* (2013.01); *A61K 39/40* (2013.01); *A61K 45/06* (2013.01); *G01N 33/56938* (2013.01); *A61K 2039/505* (2013.01); *A61K 2039/507* (2013.01); *C07K 2317/52* (2013.01); *C07K 2317/56* (2013.01); *C07K 2317/565* (2013.01); *C07K 2317/567* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,979,446 | B2 * | 12/2005 | Patti | C07K 16/1271 424/130.1 |
| 7,364,738 | B2 * | 4/2008 | Patti | C07K 16/1271 424/130.1 |
| 7,396,917 | B2 * | 7/2008 | Bowdish | C07K 14/505 530/387.1 |
| 8,715,687 | B2 * | 5/2014 | Dequesne | A61K 39/085 424/190.1 |
| 8,808,699 | B2 * | 8/2014 | Schneewind | A61K 39/085 424/139.1 |
| 8,889,145 | B2 * | 11/2014 | Anderson | A61K 39/085 424/165.1 |
| 9,399,673 | B2 * | 7/2016 | Beaumont | C07K 16/1271 |
| 9,527,905 | B2 * | 12/2016 | Sellman | C07K 16/1271 |
| 9,527,927 | B2 * | 12/2016 | Chowdhury | C07K 16/468 |
| 2003/0044772 | A1 | 3/2003 | Watkins et al. | |
| 2003/0099656 | A1 * | 5/2003 | Patti | C07K 16/1271 424/165.1 |
| 2005/0013819 | A1 | 1/2005 | Kinch et al. | |
| 2005/0136053 | A1 | 6/2005 | Hufton et al. | |
| 2005/0287164 | A1 * | 12/2005 | Patti | C07K 16/1271 424/190.1 |
| 2007/0004910 | A1 | 1/2007 | Sexton et al. | |
| 2007/0044171 | A1 | 2/2007 | Kovalic et al. | |
| 2008/0050361 | A1 | 2/2008 | Heinrichs et al. | |
| 2008/0299129 | A1 | 12/2008 | Lewis et al. | |
| 2010/0040606 | A1 | 2/2010 | Lantto et al. | |
| 2015/0291685 | A1 * | 10/2015 | Sellman | C07K 16/1271 424/133.1 |
| 2016/0194377 | A1 * | 7/2016 | Hook | A61K 38/363 435/7.92 |

(Continued)

FOREIGN PATENT DOCUMENTS

| | | | |
|---|---|---|---|
| WO | WO 2002/072600 | * | 9/2002 |
| WO | WO 2007/145689 A1 | | 12/2007 |

(Continued)

OTHER PUBLICATIONS

Bebbington et al, Current Opinion in Biotechnology, 2008, 19:613-619.*
Domanski et al, Infection and Immunity, Aug. 2005, 73/8:5229-5232.*
Ganesh et al, EBioMedicine, 2016, 13:328-338.*
Hall et al, Infection and Immunity, Dec. 2003, 71/12:6864-6870.*
Patti, Vaccine, 2004, 22S:S39-S43.*
Peerschke et al, Blood, Nov. 16, 2000, 96/11,Part 1, pp. 38a (abstract only).*
Tkaczyk et al, mBio Jun. 28, 2016, 7(3):e00528-16.*

(Continued)

*Primary Examiner* — Nita M. Minnifield

(57) ABSTRACT

Antibodies and antigen binding fragments thereof directed against *Staphylococcus aureus* (*S. aureus*) surface determinant antigens and secreted toxins are disclosed. Methods of detecting, diagnosing and treating *S. aureus* using the antibodies and antigen binding fragments thereof are also provided.

6 Claims, 18 Drawing Sheets

(56) References Cited

U.S. PATENT DOCUMENTS

| | | | |
|---|---|---|---|
| 2016/0235832 A1* | 8/2016 | Ko | A61K 39/085 |
| 2017/0015734 A1* | 1/2017 | Simard | A61K 38/14 |
| 2017/0023569 A1* | 1/2017 | Daiss | G01N 33/569 |

FOREIGN PATENT DOCUMENTS

| | | | |
|---|---|---|---|
| WO | WO 2008/152447 A2 | | 12/2008 |
| WO | WO 2010/042481 | * | 4/2010 |
| WO | WO 2012/109285 A2 | | 8/2012 |
| WO | WO 2014/074540 A2 | * | 5/2014 |

OTHER PUBLICATIONS

Bendig, Methods A Companion to Methods in Enzymology 1995; 8: 83-93.*

Dryla, A., et al., "High-Affinity Binding of the *Staphylococcal* HarA Protein to Haptoglobin and Hemoglobin Involves a Domain with an Antiparallel Eight-Stranded β-Barrel Fold," Journal of Bacteriology, 189(1): 254-264 (2007).

Clarke, S., et al., "Identification of in Vivo-Expressed Antigens of *Staphylococcus aureus* and Their Use in Vaccinations for Protection against Nasal Carriage," Journal of Infections Diseases, 193: 1098-1108 (2006).

Myszka, D., et al., "Improving biosensor analysis," Journal of Molecular Recognition, 12: 279-284 (1999).

Smith, E., et al., "The Sbi Protein is a Multifunctional Immune Evasion Factor of *Staphylococcus aureus*" Infection and Immunity, 79(9): 3801-3809 (2011).

Visai, L., et al., "Immune evasion by *Staphylococcus aureus* conferred by iron-regulated surface determinant protein IsdH," Microbiology, 155: 667-679 (2009).

UniProt_F2U1I7, Putative uncharacterized protein, Version 1, Last modified May 31, 2011 [online]. Retrieved from the Internet.

International Search Report dated May 20, 2014, in connection with corrresponding International Application No. PCT/US2013/068624, filed Nov. 6, 2013.

Smith et al., "The Sbi Protein is a Multifunctional Immune Evasion Factor of *Staphyloccus aureus*", Infect. Immun., 2011, vol. 79, pp. 3801-3809.

Hurd et al., "The Iron-Regulated Surface Proteins IsdA, IsdB, and IsdH are not Required for Heme Iron Utilization in *Staphylococcus aureus*", FEMS Microbiology Letters, vol. 329, 2012, pp. 93-100.

Hamilton et al., "In Vitro and In Vivo Characterization of *S. aureus* Anti-IsdH mAb 2F4 (861705)", 54th Intersci Conf Antimicrob Agents Chemother (ICAAC), 2014, p. 1.

International Preliminary Report on Patentability and Written Opinion for International Application No. PCT/US2013/068624 dated May 20, 2014.

Supplementary Partial European Search Report for Application No. EP 13852597 dated Dec. 12, 2016.

Tkacyk et al., "Identification of Anti-Alpha Toxin Monoclonal Antibodies that Reduce the Severity of *Staphylococcus aureus* Dermonecrosis and Exhibit a Correlation between Affinity and Potency," Clinican and Vaccine Immunology, vol. 19, No. 3, Mar. 1, 2012, pp. 377-385.

Digiandomenico, et al., "Antibacterial monoclonal antibodies: the next generation?," Current Opinion in Microbiology, vol. 27, Aug. 25, 2015, pp. 78-85.

* cited by examiner

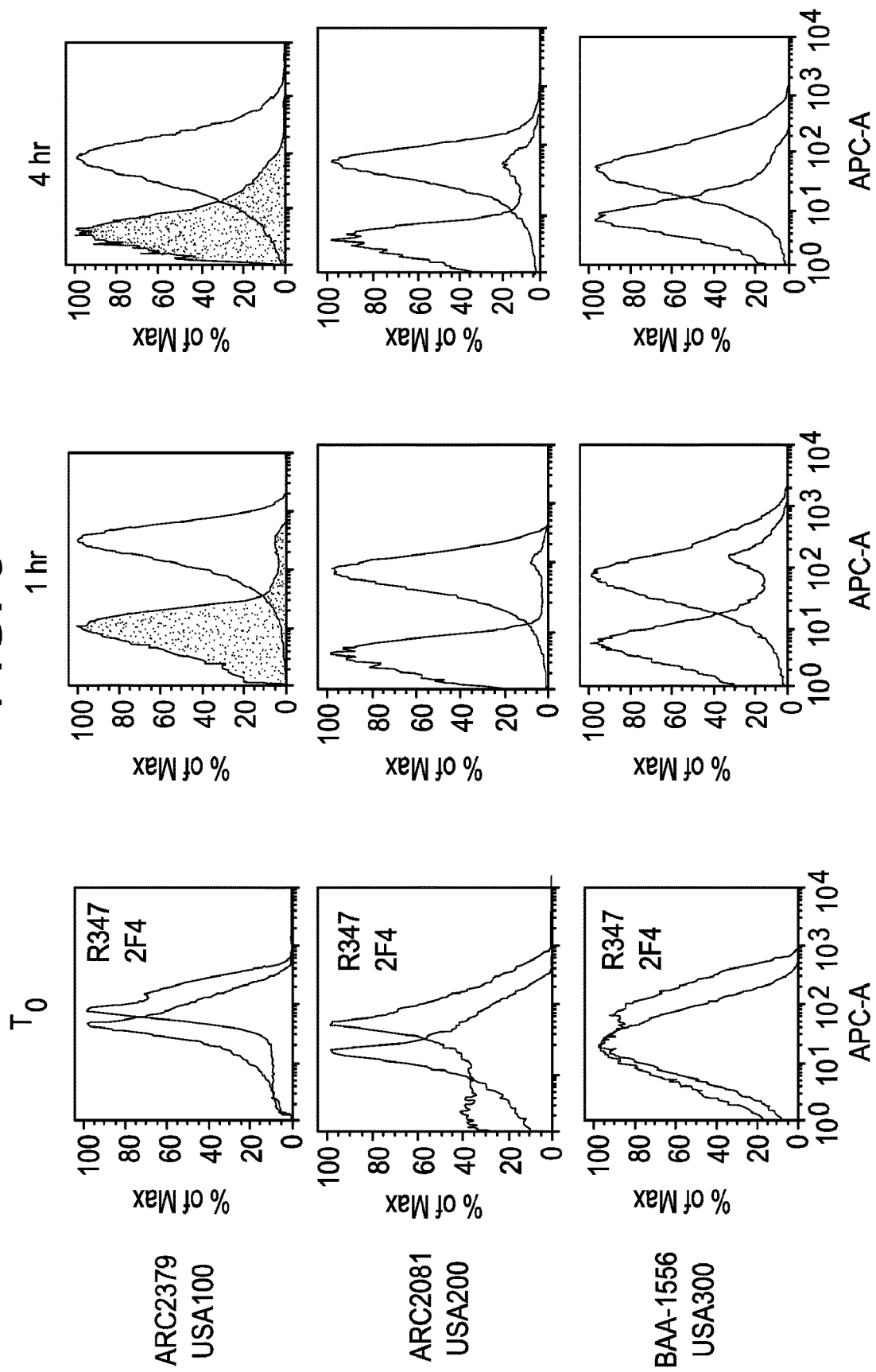

Newman (n=3)

ARC 634 (USA100)
Nares isolate

ARC20981 (USA200)

BAA-1556 (USA300)

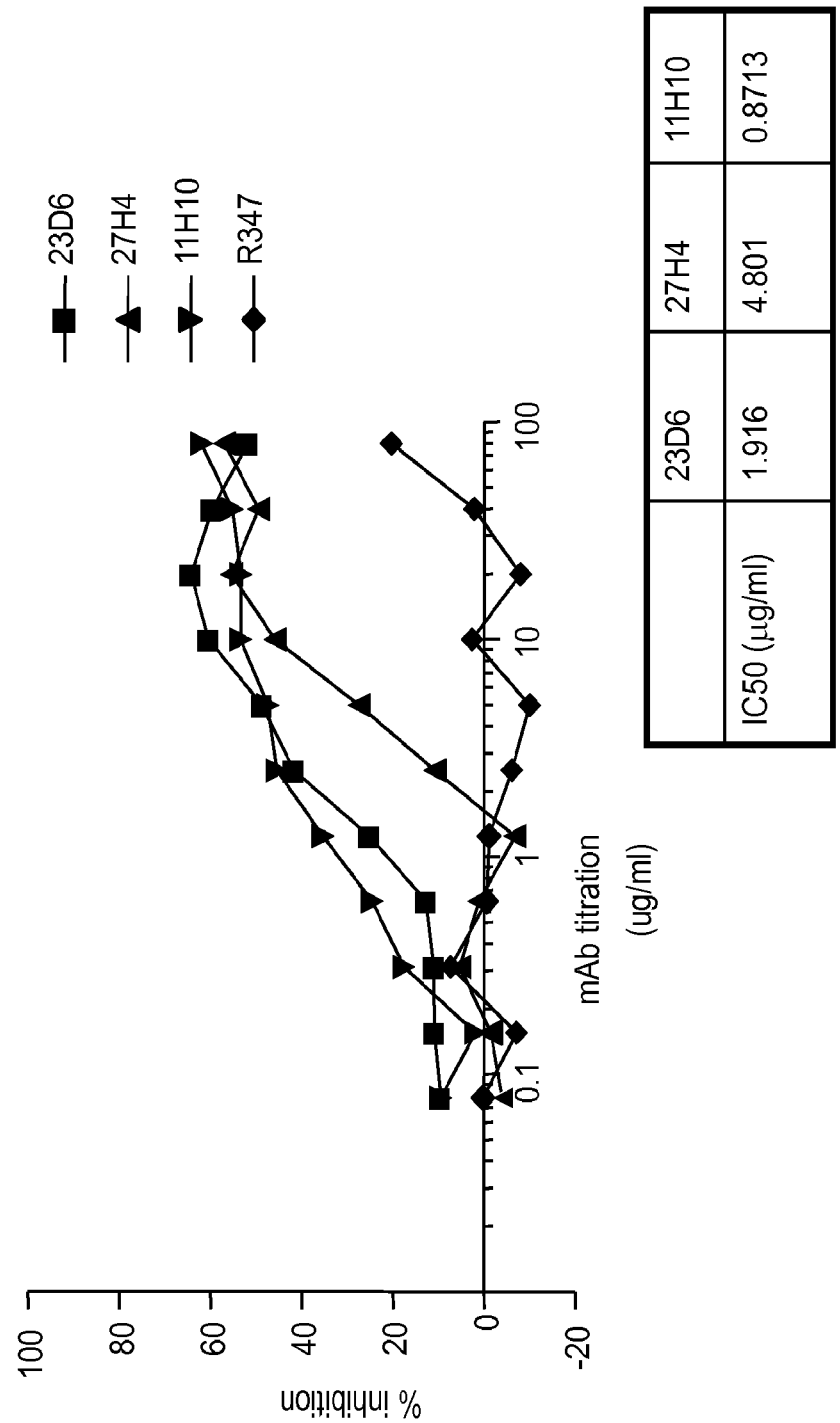

Figure 16
LC10/11H10 Combo effect on IV lethal challenge with CA-MRSA USA300 (strain SF8300, 6.4e7 cfu/mouse)
B.
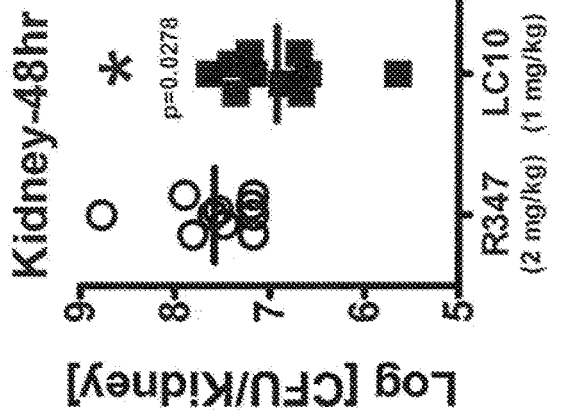
C.
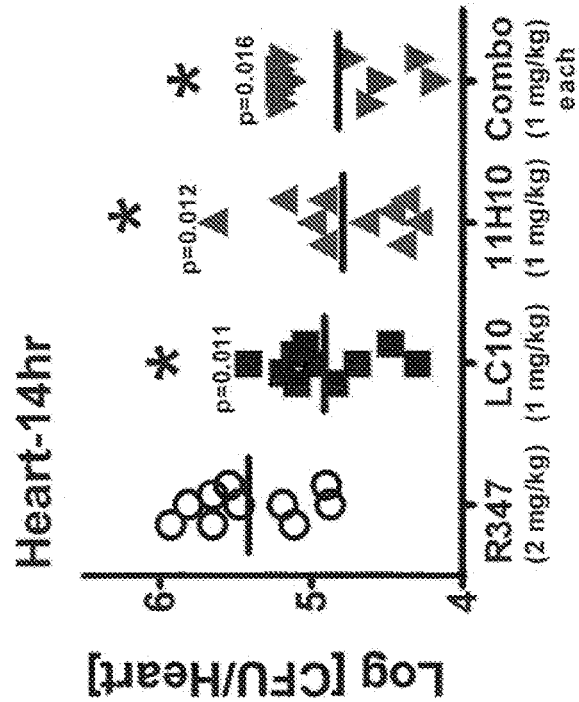
p value (CFU): *Mann Whitney U test*
p value (Survival): *Log-rank (Mantel-Cox) test*

ANTIBODIES TO *S. AUREUS* SURFACE DETERMINANTS

CROSS-REFERENCE TO RELATED APPLICATIONS

This application is a U.S. National Stage application of International Application No. PCT/US2013/068624, filed on Nov. 6, 2013, said International Application No. PCT/US2013/068624 claims benefit under 35 U.S.C. §119(e) of U.S. Provisional Application Nos. 61/723,137, filed Nov. 6, 2012, and 61/782,405, filed Mar. 14, 2013. Each of the above listed applications is incorporated by reference herein in its entirety for all purposes.

REFERENCE TO THE SEQUENCE LISTING

This application incorporates by reference a Sequence Listing submitted with this application as text file entitled ATOX-150US1_SL, created on May 5, 2015, and having a size of 6.16 MB.

The present disclosure relates generally to antibodies that bind to *Staphylococcus aureus* (*S. aureus*) surface determinants and antibodies that bind to *S. aureus* secreted toxins. The present disclosure also relates to combinations of antibodies that bind to *S. aureus* surface determinants together with antibodies that bind to *S. aureus* secreted toxins, compositions comprising such combinations of antibodies, and methods of preventing *S. aureus*-associated diseases comprising administering such combinations of antibodies.

*Staphylococcus aureus* is a Gram-positive, aerobic, clump-forming cocci bacteria that commonly colonizes the nose and skin of healthy humans. Approximately 20-30% of the population is colonized with *S. aureus* at any given time. *Staphylococcus aureus* bacteria, sometimes also referred to as "staph", "*Staph. aureus*", or "*S. aureus*", are considered opportunistic pathogens that cause minor infections (e.g., pimples, boils and other soft tissue infections) and systemic infections (e.g., pneumonia, septicemia, osteomyelitis, and endocarditis).

Mucosal and epidermal barriers (skin) normally protect against *S. aureus* infections. Interruption of these natural barriers as a result of injuries (e.g., burns, trauma, and surgical procedures) dramatically increases the risk of infection. Diseases that compromise the immune system (e.g., diabetes, end-stage renal disease, and cancer) also increase the risk of infection. Opportunistic *S. aureus* infections can become serious, causing a variety of diseases or conditions, non-limiting examples of which include bacteremia, cellulitis, eyelid infections, food poisoning, joint infections, skin infections, scalded skin syndrome, toxic shock syndrome, pneumonia, osteomyelitis, endocarditis, meningitis and abscess formation.

*S. aureus* expresses a number of surface determinant antigens, including the serine-aspartic acid repeat proteins SdrC, SdrD, and SdrE, the clumping factor proteins ClfA and ClfB, the iron-regulated surface determinant proteins IsdA, IsdB, IsdC, IsdE and IsdH, *S. aureus* protein A (SpA) and polysaccharide poly-N-aceytlglucosamine (PNAG). These surface antigens play a role in colonization of host tissue, evasion of the host immune response, and bacterial fitness. Mutations to ClfA, SpA, IsdA, IsdB, and IsdH have been shown to reduce *S. aureus* virulence.

Proteins such as IsdH play a role in the ability of *S. aureus* to evade certain host immune responses, such as neutrophil-mediated phagocytosis, a process that is critical for *S. aureus* to cause infection. IsdH is part of a complex that is activated under iron-restricted conditions, serving to bind hemoglobin and the haptoglobin-hemoglobin complex, and then extracting and transporting heme into the cytoplasm. Three N-terminal NEAr Transporter (NEAT) motifs are present within IsdH, the determined structure of NEAT1 indicating that certain residues within this motif are involved in ligand binding. IsdH-defective mutants of *S. aureus* have been shown to have reduced virulence compared with wild-type, and are engulfed more rapidly by human neutrophils in the presence of serum opsonins. The protective mechanism of IsdH appears to stem from an accelerated degradation of the serum opsonin C3b. IsdH thus plays a role in the antiphagocytic properties of the *S. aureus* organism.

ClfA is a virulence factor that binds fibrinogen. This function of ClfA appears to further contribute to the antiphagocytic properties of *S. aureus*. In addition, ClfA also promotes *S. aureus* agglutination in blood and biofilm formation to biomaterial surfaces.

*S. aureus* also expresses several additional virulence factors, including capsular polysaccharides and protein toxins. One virulence factor often associated with *S. aureus* infection is alpha toxin (also known as alpha-hemolysin or Hla), a pore-forming and hemolytic exoprotein produced by most pathogenic strains of *S. aureus*. The toxin forms heptameric pores in membranes of susceptible cells such as white blood cells, platelets, erythrocytes, peripheral blood monocytes, macrophages, keratinocytes, fibroblasts and endothelial cells. Alpha toxin pore formation often leads to cell dysfunction or lysis. It can also lead to a disruption of epithelial and endothelial tight junctions and immune dysregulation.

Currently, *S. aureus* is the leading cause of infection-related mortality in the US, and is the leading cause of hospital-acquired infection. Further, growing antibiotic resistance to *S. aureus* has compounded the problem. Therefore, it would be desirable to develop effective alternative methods of diagnosing and treating *S. aureus* infections, including combination antibody therapies.

As disclosed previously in U.S. Prov. Appl. No. 61/440,581 and in Intl. Appl. No. PCT/US2012/024201 (published as WO2012/109205), the contents of each which are herein incorporated by reference, antibodies that bind to *S. aureus* alpha-toxin have been shown to reduce CA-MRSA disease severity in a murine dermonecrosis model and promote bacterial clearance in a mouse model of staphycoccal pneumonia. Thus, such antibodies can be utilized for the treatment of various *S. aureus*-associated diseases.

In addition to antibodies that bind to *S. aureus* alpha-toxin, the present disclosure provides for antibodies directed against *S. aureus* surface determinant antigens, as well as combinations thereof. The present invention provides for compositions comprising such antibodies, or combinations of such antibodies, as well as methods of prevention and/or treatment of *S. aureus*-associated diseases using such antibodies, or combinations of such antibodies. Methods of prevention and/or treatment of *S. aureus*-associated diseases using antibodies that bind to *S. aureus* alpha-toxin are described in U.S. Prov. Appl. No. 61/440,581 and in Intl. Appl. No. PCT/US2012/024201 (published as WO2012/109205), the contents of which are herein incorporated by reference, as well as in the U.S. Provisional Application filed concomitantly with the current application, to Sellman et al., entitled "Methods of Treating *S. Aureus* Associated Diseases," the contents of which are herein incorporated by reference.

The present invention also provides for certain combinations of antibodies, such as an antibody that binds to an *S.* aureus surface determinant in combination with an antibody that binds to *S. aureus* alpha toxin, where such combinations work synergistically together. The present invention also provides for combining an antibody that targets an *S. aureus* surface determinant antigen involved in evading opsonophagocytic functions of the host together with an antibody that targets an *S. aureus* secreted toxin involved in directly damaging host cells.

DESCRIPTION OF THE DRAWINGS

FIG. 5A shows the concentration of *S. aureus* colony forming units (CFU) measured in a mouse bacteremia model in the presence of antibody 2F4 with the results having a p value of 0.02, whereas FIG. 5B shows the concentration of *S. aureus* colony forming units (CFU) measured in a mouse bacteremia model in the presence of antibody 2F4 with the results having a p value of 0.005. CFU concentration is reported as $\log_{10}[\text{CFU/ml}]$.

FIG. 6 illustrates 2F4 binding, measured as a percentage of maximum binding, as compared to control antibody R347, at time $T_0$, $T_{1hr}$, and $T_{4hr}$ in *S. aureus* strains ARC2379 (USA100), ARC2081 (USA200) and BAA-1556 (USA 300).

FIG. 10 shows that anti-ClfA antibodies inhibit ClfA binding to immobilized fibrinogen. Anti-ClfA antibodies 23D6, 27H4, 11H10 shown increased inhibition of binding to fibrinogen as compared to the control R347.

FIG. 16 shows the effect of the combination of anti-ClfA antibody 11H10 with the anti-At antibody LC10 in a murine sepsis model (IV lethal challenge) with HA-MRSA USA100 challenge.

DESCRIPTION OF ILLUSTRATIVE EMBODIMENTS

Figure 1:
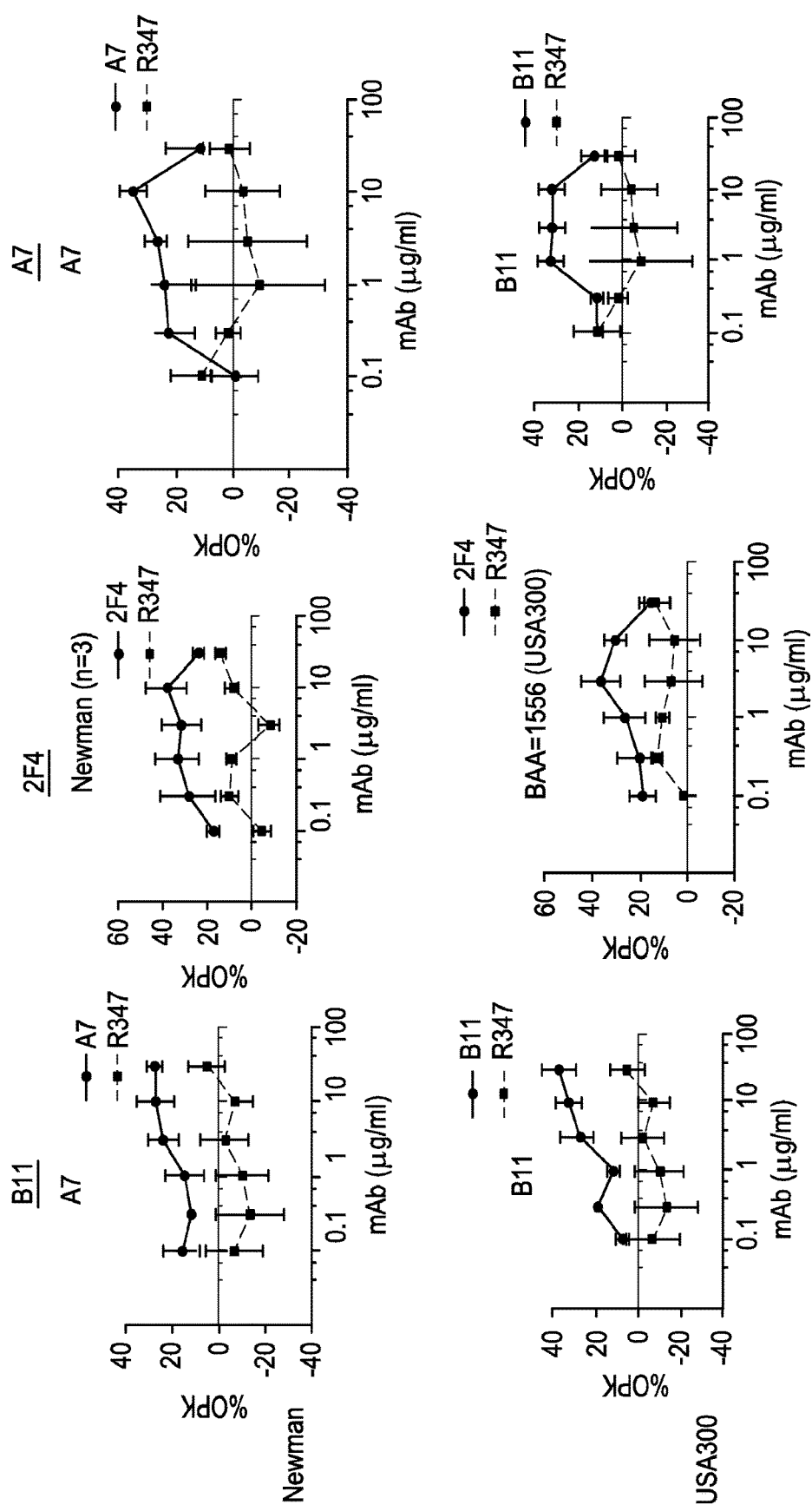
FIG. 1 shows the percentage of opsonophagocytic killing (OPK) induced by anti-IsdH antibodies B11, 2F4, and A7, as compared to percent OPK induced by control antibody R347, when tested with *S. aureus* strains Newman and USA300.

Reference will now be made in detail to certain exemplary embodiments according to the present disclosure, certain examples of which are illustrated in the accompanying drawings.

Disclosed herein are antibodies, including human, humanized and/or chimeric forms, as well as fragments, derivatives/conjugates and compositions thereof, that bind to *S. aureus* surface determinant antigens and antibodies that bind to *S. aureus* secreted toxins. Such antibodies can be useful for detecting and/or visualizing *S. aureus* and therefore may be useful in diagnostic methods and assays. Antibodies described herein also interfere with *S. aureus* surface determinants, thereby interfering with colonization and immune evasion, thereby making the antibodies useful for therapeutic and prophylactic methods. Likewise, antibodies described herein can bind *S. aureus* secreted toxins, thereby reducing the virulence of *S. aureus* infection. Combining antibodies that target both *S. aureus* surface determinants and secreted toxins can increase the therapeutic or prophylactic effect achieved by either antibody when administered individually.

*S. aureus* expresses a number of surface determinant antigens that are important for *S. aureus* colonization, immune evasion, and fitness. Such surface determinants include SdrC, SdrD, SdrE, ClfA, ClfB, IsdA, IsdB, IsdC, IsdE, IsdH, SpA, FnbA and PNAG. Antibodies disclosed herein can target the surface determinant antigens.

*S. aureus* also produces a large number of secreted and cell-associated proteins, many of which are involved in pathogenesis, such as alpha-toxin (AT), beta-toxin, gamma-toxin, delta-toxin, leukocidin, toxic shock syndrome toxin (TSST), enterotoxins, coagulase, protein A, fibrinogen, and the like. Alpha toxin is one of the virulence factors of *Staphylococcus aureus* and is produced by the majority of pathogenic *S. aureus* strains.

A. Antibodies Directed Against *S. aureus* Surface Determinants and Secreted Toxins As used herein, the terms "antibody," "antibodies" (also known as immunoglobulins) and "antigen-binding fragments," encompass monoclonal antibodies (including full-length monoclonal antibodies), polyclonal antibodies, multispecific antibodies formed from at least two different epitope binding fragments (e.g., bispecific antibodies), human antibodies, humanized antibodies, camelid antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g., the antigen binding portion), disulfide-linked Fvs (dsFv), and anti-idiotypic (anti-Id) antibodies (including, e.g., anti-Id antibodies to antibodies herein provided), intrabodies, and epitope-binding fragments of any of the above. In particular, antibodies include immunoglobulin molecules and immunologically active fragments of immunoglobulin molecules, i.e., molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Antibodies may be derived from any mammal, including, but not limited to, humans, monkeys, pigs, horses, rabbits, dogs, cats, mice, and the like, or other animals such as birds (e.g., chickens).

In certain embodiments, an antibody, or immunospecific fragment thereof of the invention includes an antigen binding domain. An antigen binding domain is formed by antibody variable regions that vary from one antibody to another. Naturally occurring antibodies comprise at least two antigen binding domains, i.e., they are at least bivalent. As used herein, the term "antigen binding domain" includes a site that specifically binds an epitope on an antigen (e.g., a cell surface or soluble antigen). The antigen binding domain of an antibody typically includes at least a portion of an immunoglobulin heavy chain variable region and at least a portion of an immunoglobulin light chain variable region. The binding site formed by these variable regions determines the specificity of the antibody.

As used herein, unless otherwise specifically indicated, a "mutation" encompasses an addition, deletion, substitution (including conservative substitution) or other alteration of at least one amino acid or nucleic acid. A "conservative substitution," unless otherwise specifically indicated, refers to the replacement of a first amino acid by a second amino acid that does not substantially alter the chemical, physical and/or functional properties of the antibody or antigen binding fragment thereof (e.g., the antibody or antigen binding fragment thereof retains the same charge, structure, polarity, hydrophobicity/hydrophilicity, and/or preserves functions such as the ability to bind alpha toxin and thereby reduce *S. aureus* virulence). A conservative substitution also refers to the replacement of a first nucleic acid by a second nucleic acid encoding for the conservative amino acid substitution described previously.

Antibodies provided herein include full length or intact antibodies, antibody fragments, native sequence antibodies or amino acid variants of native antibodies, human, humanized, post-translationally modified, chimeric or fusion antibodies, immunoconjugates, and functional fragments thereof. The antibodies can be modified in the Fc region, and certain modifications can provide desired effector functions or altered serum half-life.

The numbering of amino acids in the variable domain, complementarity determining region (CDRs) and framework regions (FR), of an antibody follow, unless otherwise indicated, the Kabat definition as set forth in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, to be used for the Fv region. In addition, the identity of certain individual residues at any given Kabat site number may vary from antibody chain to antibody chain due to interspecies or allelic divergence.

In certain embodiments, isolated antibodies are provided. The term "isolated antibody," as used herein, refers to an antibody which is substantially free of other antibodies and molecules normally present in the native cellular environment. Thus, in some embodiments, antibodies provided are isolated antibodies where they have been separated from antibodies with a different antigen specificity. An isolated antibody may be a monoclonal antibody or a polyclonal antibody. An isolated antibody that specifically binds to an epitope, isoform or variant of *S. aureus* surface antigen or secreted toxin may, however, have cross-reactivity to other related antigens, e.g., from other species (e.g., *Staphylococcus* species homologs). An isolated antibody as provided may be substantially free of one or more other cellular materials. In some embodiments, a combination of "isolated" monoclonal antibodies is provided, and pertains to antibodies having different specificities and combined in a defined composition.

Also disclosed are isolated nucleic acid sequences that encode for the amino acid sequences of the disclosed antibodies and antigen binding fragments thereof of antibodies. Due to the degeneracy of the nucleotide code, more than one nucleotide may be present at any nucleic acid position while still encoding for the same amino acid. In some embodiments, nucleic acid sequences are provided that encode for amino acid sequences that are 70%, 75%, 80%, 85%, 90%, 95%, 99%, or 100% identical (or any percentage in between) to the amino acid sequence of a disclosed antibody or antigen binding fragment thereof that binds an *S. aureus* surface antigen or secreted toxin. In further embodiments, the nucleic acid sequences encode for amino acid sequences that retain the functional abilities of the disclosed antibodies and antigen binding fragments thereof, e.g. to bind an *S. aureus* surface antigen or secreted toxin and thereby reduce *S. aureus* colony growth, evasion of opsonophagocytosis, or toxicity of a secreted toxin.

In various embodiments, the antibodies or fragments disclosed herein can specifically bind to an *S. aureus* surface antigen or secreted toxin polypeptide or antigenic fragment thereof. In certain embodiments, the surface antigen is SdrC, SdrD, SdrE, ClfA, ClfB, IsdA, IsdB, IsdC, IsdE, IsdH, SpA, FnbA or PNAG. In further embodiments, the surface antigen is IsdH. In other embodiments, the surface antigen is ClfA. In some embodiments, the secreted toxin is alpha toxin or a phenol-soluble modulin. In further embodiments, the secreted toxin is alpha toxin. Certain amino acid and nucleic acid sequences for alpha toxin antibodies useful in the present disclosure are disclosed in U.S. Prov. Appl. No. 61/440,581 and in Intl. Appl. No. PCT/US2012/024201 (published as WO2012/109205), the contents of each which are hereby incorporated in their entireties.

Antibodies provided herein can specifically bind to one or more epitopes specific to an *S. aureus* surface determinant antigen or secreted toxin protein, and generally do not specifically bind to other polypeptides. The term "epitope" as used herein refers to a peptide, subunit, fragment, portion, oligomer or any combination thereof capable of being bound by an antibody.

In certain embodiments, an *S. aureus* surface determinant antigen or secreted toxin antibody or antigen binding fragment thereof may bind an epitope conserved across species. In some embodiments, an antibody or antigen binding fragment thereof binds an *S. aureus* surface determinant antigen or secreted toxin or a homolog or ortholog from another bacterial species, as well as antigenic fragments thereof. In some embodiments the antibody or antigen binding fragment thereof may bind to one or more isoforms of a surface determinant antigen or secreted toxin.

In various embodiments, an epitope is comprised of at least a portion of an *S. aureus* surface determinant antigen. These surface determinant antigens can include SdrC, SdrD, SdrE, ClfA, ClfB, IsdA, IsdB, IsdC, IsdE, IsdH, SpA, FnbA or PNAG. In some embodiments, the antigen is IsdH. In other embodiments, the antigen is ClfA. In other embodiments, an epitope is comprised of at least a portion of an *S. aureus* secreted toxin. In some embodiments, the secreted toxin is alpha toxin, which is involved in formation of an alpha toxin heptamer complex.

A specified epitope can comprise any amino acid sequence comprising at least 3 contiguous amino acid residues from the amino acid sequence of the target antigen. The epitope may comprise longer amino acid sequences, up to and including the entire amino acid sequence of the target antigen. In some embodiments, the epitope comprises at least 4 amino acid residues, at least 5 amino acid residues, at least 6 amino acid residues, at least 7 amino acid residues, at least 8 amino acid residues, at least 9 amino acid residues, at least 10 amino acid residues, at least 11 amino acid residues, at least 12 amino acid residues, at least 13 amino acid residues, at least 14 amino acid residues, or at least 15 amino acid residues from the amino acid sequence of the target antigen. In certain other embodiments, the epitope comprises 2, 3, 4, 5, 6, 7, 8, 9, 10, 11, 12, 13, 14 or 15 contiguous or non-contiguous amino acid residues from the amino acid sequence of the target antigen.

In certain embodiments, a combination is provided, comprising an isolated antibody or antigen binding fragment thereof that specifically binds to an *S. aureus* secreted toxin and an isolated antibody that specifically binds to an *S. aureus* surface determinant antigen. In further embodiments, the antibody that binds an *S. aureus* surface determinant antigen binds an antigen selected from SdrC, SdrD, SdrE, ClfA, ClfB, IsdA, IsdB, IsdC, IsdE, IsdH, SpA, FnbA or PNAG. In still further embodiments, the surface determinant antigen is IsdH. In certain embodiments, the antibody that binds an *S. aureus* secreted toxin binds a toxin selected from alpha toxin and a phenol-soluble modulin. In further embodiments, the secreted toxin is alpha toxin.

In certain embodiments, the antibody or combination of antibodies is present in an aqueous solution. In other embodiments, the antibody or combination of antibodies is present in a powdered or lyophilized form. In certain embodiments, the antibody or combination of antibodies is at a concentration sufficient for therapeutic or diagnostic uses. In some embodiments, the antibody or combination of antibodies is present in a sterile vessel or container.

In certain embodiments, an antibody or antigen binding fragment thereof capable of binding an *S. aureus* surface antigen or secreted toxin is prepared from a parent antibody. As used herein, the term "parent antibody" refers to an antibody that is encoded by an amino acid sequence used for the preparation of a variant or derivative antibody, as defined herein. A parent polypeptide may comprise a native antibody sequence (i.e., a naturally occurring antibody polypeptide, including a naturally occurring allelic variant) or an antibody sequence with pre-existing amino acid sequence modifications (such as insertions, deletions and/or substitutions) of a naturally occurring sequence. A parent antibody may be a humanized antibody or a human antibody. In specific embodiments, the *S. aureus* surface antigen or secreted toxin antibodies and antigen binding fragments thereof are variants of the parent antibody. As used herein, the term "variant" refers to antibody or antigen binding fragment thereof that differs in its amino acid sequence from a "parent" antibody or antigen binding fragment thereof amino acid sequence by virtue of addition, deletion and/or substitution of one or more amino acid residue(s) from the parent antibody sequence.

The present *S. aureus* surface antigen or secreted toxin antibodies and antigen binding fragments thereof comprise at least one antigen binding domain. The antigen-binding portion of an antibody comprises one or more fragments of an antibody that retain the ability to specifically bind to an antigen. These retained portions may comprise the heavy and/or light chain variable region from a parent antibody or a variant of a parent antibody.

B. Anti-IsdH Antibodies

As used herein, the terms "percent (%) sequence identity" or "homology" are defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and excluding conservative substitutions. Optimal alignment of the sequences for comparison may be produced, besides manually, by means of local homology algorithms known in the art or by means of computer programs which use these algorithms (e.g., GAP, BESTFIT, FASTA, BLAST P, BLAST N and TFASTA).

In some embodiments, an isolated antibody or antigen binding fragment thereof that specifically binds to the surface antigen IsdH comprises a heavy chain variable region (VH) having 65%, 70%, 75%, 80%, 85%, 90%, 95%, 99% or 100% identity to the amino acid sequence of SEQ ID NO:

80, 82, 84, 86, or 88. In certain embodiments, an antibody or antigen binding fragment thereof that specifically binds to IsdH comprises a light chain variable region (VL) having 65%, 70%, 75%, 80%, 85%, 90%, 95%, 99% or 100% identity to amino acid sequence of SEQ ID NO: 81, 83, 85, 87, or 89. In particular embodiments, an antibody or antigen binding fragment thereof that specifically binds to IsdH comprises a VH having 65%, 70%, 75%, 80%, 85%, 90%, 95%, 99% or 100% identity to the amino acid sequence of SEQ ID NO: 80, 82, 84, 86, or 88 and a VL comprising the amino acid sequence of SEQ ID NO: 81, 83, 85, 87, or 89.

In particular embodiments, an antibody or antigen binding fragment thereof that specifically binds to IsdH comprises a VH and a VL, wherein the VH and VL are selected from the group consisting of SEQ ID NOs: 80 and 81; SEQ ID NOs: 82 and 83; SEQ ID NOs: 84 and 85; SEQ ID NOs: 86 and 87; and SEQ ID NOs: 88 and 89. In certain embodiments an antibody or antigen binding fragment thereof that specifically binds to IsdH comprises a VH and a VL, wherein the VH and VL correspond to SEQ ID NOs: 80 and 81. Example 7, Table 12 provides for representative VH and VL sequences as presented herein which can be present in any combination to form an anti-surface antigen antibody or antigen binding fragment thereof.

In further embodiments the antibody or antigen binding fragment thereof that specifically binds to IsdH comprises a VH amino acid sequence having 1, 2, 3, 4, 5, 6, 7, 8, 9, or 10 mutations (including additions, deletions, and substitutions, such as conservative substitutions) in the amino acid sequence of SEQ ID NO: 80, 82, 84, 86, or 88. In various embodiments the antibody or antigen binding fragment thereof that specifically binds to IsdH comprises a VL amino acid sequence having 1, 2, 3, 4, 5, 6, 7, 8, 9, or 10 mutations (including additions, deletions, and substitutions, such as conservative substitutions) in the amino acid sequence of SEQ ID NO: 81, 83, 85, 87, or 89.

In certain embodiments, the antibody or antigen binding fragment that specifically binds to the surface antigen IsdH has one or more of the following characteristics:

(a) disassociation constant ($K_D$) for an *S. aureus* surface antigen of about 100 nM or less, about 90 nM or less, about 80 nM or less, about 70 nM or less, about 60 nM or less, about 50 nM or less, about 40 nM or less, about 20 nm or less, about 10 nm or less, about 9, 8, 7, 6, 5, 4, 3, 2, or 1 nm. (or any value in between);

(b) reduces the ability of *S. aureus* to evade opsonophagocytosis by immune cells by at least 50%, 60%, 70%, 80%, 90% or 95% (or any percentage in between), as measured by an opsonophagocytic killing assay;

(c) reduces the concentration of *S. aureus* colony forming units (CFUs) by at least 50%, 60%, 70%, 80%, 90% or 95% (or any percentage in between), as measured by a bacteremia model; or (d) reduces immune cell infiltration, bacterial burden, and pro-inflammatory cytokine release.

The present antibodies and antigen binding fragments thereof that specifically bind *S. aureus* surface antigens or secreted toxins comprise at least one antigen binding domain that includes at least one complementarity determining region (e.g., at least one of CDR1, CDR2 or CDR3). In some embodiments, an antibody or antigen binding fragment thereof comprises a VH that includes at least one VH CDR (e.g., VH CDR1, VH CDR2 or VH CDR3). In certain embodiments, an antibody or antigen binding fragment thereof comprises a VL that includes at least one VL CDR (e.g., VL CDR1, VL CDR2 or VL CDR3). In some embodiments, an antibody or antigen binding fragment thereof comprises a VH that includes at least one VH CDR and at least one VL CDR.

The CDR regions disclosed herein can be combined in a variety of combinations, as each CDR region can be independently selected and combined with any other CDR region for a given antibody. In certain embodiments VH and/or VL CDR sequences can be present in any combination to form an antibody or antigen binding fragment thereof directed against an *S. aureus* surface antigen or secreted toxin.

In some embodiments, an isolated antibody or antigen-binding fragment thereof that specifically binds to IsdH and includes (a) a VH CDR1 comprising an amino acid sequence identical to, or comprising 1, 2, or 3 amino acid residue mutations relative to, SEQ ID NO: 90, 96, 102, 108, or 114; (b) a VH CDR2 comprising an amino acid sequence identical to, or comprising 1, 2, or 3 amino acid residue mutations relative to SEQ ID NO: 91, 97, 103, 109, or 115; and/or (c) a VH CDR3 comprising an amino acid sequence identical to, or comprising 1, 2, or 3 amino acid residue mutations relative to SEQ ID NO: 92, 98, 104, 110, or 116.

In some embodiments, the isolated antibody or antigen-binding fragment thereof that specifically binds to IsdH includes, (a) a VL CDR1 comprising an amino acid sequence identical to, or comprising 1, 2, or 3 amino acid residue mutations relative to SEQ ID NO: 93, 99, 105, 111, or 117; (b) a VL CDR2 comprising an amino acid sequence identical to, or comprising 1, 2, or 3 amino acid residue mutations relative to SEQ ID NO: 94, 100, 106, 112, or 118; and/or (c) a VL CDR3 comprising an amino acid sequence identical to, or comprising 1, 2, or 3 amino acid residue mutations relative to SEQ ID NO: 95, 101, 107, 113, or 119.

In some embodiments, the isolated antibody or antigen-binding fragment thereof that specifically binds to IsdH comprises a VH CDR1, VH CDR2, VH CDR3, VL CDR1, VL CDR2 and VL CDR3 comprising amino acid sequences identical to, or comprising 1, 2, or 3 amino acid residue mutations in each CDR relative to: (a) a VH CDR1 comprising the amino acid sequence of SEQ ID NO: 90, 96, 102, 108, or 114; (b) a VH CDR2 comprising the amino acid sequence of SEQ ID NO: 91, 97, 103, 109, or 115; (c) a VH CDR3 comprising the amino acid sequence of SEQ ID NO: 92, 98, 104, 110, or 116; (d) a VL CDR1 comprising the amino acid sequence of SEQ ID NO: 93, 99, 105, 111, or 117; (e) a VL CDR2 comprising the amino acid sequence of SEQ ID NO: 94, 100, 106, 112, or 118; and (f) a VL CDR3 comprising the amino acid sequence of SEQ ID NO: 95, 101, 107, 113, or 119.

In particular embodiments, the isolated antibody or antigen-binding fragment thereof that specifically binds to IsdH comprises a VH CDR1, VH CDR2, VH CDR3, VL CDR1, VL CDR2 and VL CDR3, wherein the VH CDR1, VH CDR2, VH CDR3, VL CDR1, VL CDR2 and VL CDR3 are selected from the group consisting of SEQ ID NOs: 90, 91, 92, 93, 94 and 95; SEQ ID NOs: 96, 97, 98, 99, 100, and 101; SEQ ID NOs: 102, 103, 104, 105, 106, and 107; SEQ ID NOs: 108, 109, 110, 111, 112, and 113; SEQ ID NOs: 114, 115, 116, 117, 118 and 119. In a further embodiment, the isolated antibody or antigen-binding fragment thereof that specifically binds to IsdH comprises a VH CDR1, VH CDR2, VH CDR3, VL CDR1, VL CDR2 and VL CDR3, wherein the VH CDR1, VH CDR2, VH CDR3, VL CDR1, VL CDR2 and VL CDR3 corresponds to SEQ ID NOs: 90, 91, 92, 93, 94 and 95.

In some embodiments, the isolated antibody or antigen-binding fragment thereof that specifically binds to IsdH corresponds to any one of the isolated antibody or antigen-binding fragments as described above, and has one or more of the following characteristics:

(a) disassociation constant ($K_D$) for an *S. aureus* surface antigen of about 100 nM or less, about 90 nM or less, about 80 nM or less, about 70 nM or less, about 60 nM or less, about 50 nM or less, or about 40 nM or less, about 20 nm or less, about 10 nm or less, about 9, 8, 7, 6, 5, 4, 3, 2, or 1 nm. (or any value in between);

(b) reduces the ability of *S. aureus* to evade opsonophagocytosis by immune cells by at least 50%, 60%, 70%, 80%, 90% or 95% (or any percentage in between), as measured by an opsonophagocytic killing assay;

(c) reduces the number of *S. aureus* colony forming units (CFUs) by at least 50%, 60%, 70%, 80%, 90% or 95% (or any percentage in between), as measured by a bacteremia model; or (d) reduces immune cell infiltration, bacterial burden, and pro-inflammatory cytokine release.

In further embodiments, the invention provides an isolated antibody or antigen-binding fragment thereof which specifically binds to the same IsdH epitope as any one of the anti-ClfA antibodies or antigen binding fragments described above.

C. Anti-ClfA Antibodies

In some embodiments, an isolated antibody or antigen binding fragment thereof that specifically binds to the surface antigen ClfA comprises a heavy chain variable region (VH) having 65%, 70%, 75%, 80%, 85%, 90%, 95%, 99% or 100% identity to the amino acid sequence of SEQ ID NO: 132 or 140. In certain embodiments, an antibody or antigen binding fragment thereof that specifically binds to ClfA comprises a light chain variable region (VL) having 65%, 70%, 75%, 80%, 85%, 90%, 95%, 99% or 100% identity to amino acid sequence of SEQ ID NO: 136 or 144. In particular embodiments, an antibody or antigen binding fragment thereof that specifically binds to ClfA comprises a VH having 65%, 70%, 75%, 80%, 85%, 90%, 95%, 99% or 100% identity to the amino acid sequence of SEQ ID NO: 132 or 136 and a VL comprising the amino acid sequence of SEQ ID NO: 140 or 144. In particular embodiments, an antibody or antigen binding fragment thereof that specifically binds to ClfA comprises a VH and a VL, wherein the VH and VL are selected from the group consisting of SEQ ID NOs: 132 and 140; and SEQ ID NOs: 136 and 144. Example 7, Table 14 provides for representative VH and VL sequences as presented herein which can be present in any combination to form an anti-surface antigen antibody or antigen binding fragment thereof.

In further embodiments the isolated antibody or antigen binding fragment thereof that specifically binds to ClfA comprises a VH amino acid sequence having 1, 2, 3, 4, 5, 6, 7, 8, 9, or 10 mutations (including additions, deletions, and substitutions, such as conservative substitutions) in the amino acid sequence of SEQ ID NO: 132 or 140. In various embodiments the antibody or antigen binding fragment thereof that specifically binds to ClfA comprises a VL amino acid sequence having 1, 2, 3, 4, 5, 6, 7, 8, 9, or 10 mutations (including additions, deletions, and substitutions, such as conservative substitutions) in the amino acid sequence of SEQ ID NO: 136 or 144.

In some embodiments, an isolated antibody or antigen-binding fragment thereof that specifically binds to ClfA and includes (a) a VH CDR1 comprising an amino acid sequence identical to, or comprising 1, 2, or 3 amino acid residue mutations relative to, SEQ ID NO: 133 or 141; (b) a VH CDR2 comprising an amino acid sequence identical to, or comprising 1, 2, or 3 amino acid residue mutations relative to SEQ ID NO: 134 or 142; and/or (c) a VH CDR3 comprising an amino acid sequence identical to, or comprising 1, 2, or 3 amino acid residue mutations relative to SEQ ID NO: 135 or 143.

In some embodiments, the isolated antibody or antigen-binding fragment thereof that that specifically binds to ClfA includes, (a) a VL CDR1 comprising an amino acid sequence identical to, or comprising 1, 2, or 3 amino acid residue mutations relative to SEQ ID NO: 137 or 145; (b) a VL CDR2 comprising an amino acid sequence identical to, or comprising 1, 2, or 3 amino acid residue mutations relative to SEQ ID NO: 138 or 146; and/or (c) a VL CDR3 comprising an amino acid sequence identical to, or comprising 1, 2, or 3 amino acid residue mutations relative to SEQ ID NO: 139 or 147.

In some embodiments, the isolated antibody or antigen-binding fragment thereof that specifically binds to ClfA comprises a VH CDR1, VH CDR2, VH CDR3, VL CDR1, VL CDR2 and VL CDR3 comprising amino acid sequences identical to, or comprising 1, 2, or 3 amino acid residue mutations in each CDR relative to: (a) a VH CDR1 comprising the amino acid sequence of SEQ ID NO: 133 or 141; (b) a VH CDR2 comprising the amino acid sequence of SEQ ID NO: 134 or 142; (c) a VH CDR3 comprising the amino acid sequence of SEQ ID NO: 135 or 143; (d) a VL CDR1 comprising the amino acid sequence of SEQ ID NO: 137 or 145; (e) a VL CDR2 comprising the amino acid sequence of SEQ ID NO: 138 or 146; and (f) a VL CDR3 comprising the amino acid sequence of SEQ ID NO: 139 or 147.

In particular embodiments, the isolated antibody or antigen-binding fragment thereof that specifically binds to IsdH comprises a VH CDR1, VH CDR2, VH CDR3, VL CDR1, VL CDR2 and VL CDR3, wherein the VH CDR1, VH CDR2, VH CDR3, VL CDR1, VL CDR2 and VL CDR3 are selected from the group consisting of SEQ ID NOs: 133, 134, 135, 137, 138 and 139; and SEQ ID NOs: 141, 142, 143, 144, 145, 146 and 147.

In further embodiments, the invention provides an isolated antibody or antigen-binding fragment thereof which specifically binds to the same ClfA epitope as any one of the anti-ClfA antibodies or antigen binding fragments described above.

D. Anti-Alpha Toxin (AT) Antibodies

In some embodiments, an antibody or antigen binding fragment thereof directed against a secreted toxin comprises a VH comprising the amino acid sequence of SEQ ID NO: 20, 22, 24, 26, 28, 41, 43, 45, 47, 49, 51, 53, 55, 57, 79, 59, 61, or 62. In certain embodiments, an anti-secreted toxin antibody or antigen binding fragment thereof comprises a VL comprising the amino acid sequence of SEQ ID NO: 19, 21, 23, 25, 27, 42, 44, 46, 48, 50, 52, 54, 56, 58, 60 or 63. In yet another embodiment, an anti-alpha toxin antibody or antigen binding fragment thereof comprises a VH comprising the amino acid sequence of SEQ ID NO: 20, 22, 24, 26, 28, 41, 43, 45, 47, 49, 51, 53, 55, 57, 79, 59, 61, or 62 and a VL comprising the amino acid sequence of SEQ ID NO: 19, 21, 23, 25, 27, 42, 44, 46, 48, 50, 52, 54, 56, 58, 60 or 63. See Example 7, Table 7 for a representation of VH and VL sequences as presented herein which can be present in any combination to form an anti-alpha toxin antibody or antigen binding fragment thereof, or present in a combination to form a mAb of the invention. In some embodiments, the VH is SEQ ID NO: 20, 22, 24, 26, 28, 41, 43, 45, 47, 49, 51, 53, 55, 57, 79, 59, 61, or 62. In various embodiments, the VL is SEQ ID NO: 19, 21, 23, 25, 27, 42, 44, 46, 48, 50, 52, 54, 56, 58, 60 or 63.

Certain VH and VL nucleotide sequences encoding the VH and VL amino acid sequences discussed herein are presented in Example 7, Table 8.

In some embodiments, the isolated antibodies or antigen-binding fragments disclosed herein comprise a VH and a VL, where the VH and VL have amino acid sequences represented by SEQ ID NOs: 20 and 19; SEQ ID NOs: 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

In certain embodiments, antibodies or fragments directed against *S. aureus* surface antigens or secreted toxins comprise a VH and/or VL that has a given percent identify to at least one of the VH and/or VL sequences disclosed in Table 7.

In some embodiments, an anti-secreted toxin antibody or antigen binding fragment thereof comprises a VH amino acid sequence comprising at least 65%, 70%, 75%, 80%, 85%, 90%, 95%, 99% or 100% (or any percentage in between) identity to the amino acid sequence of SEQ ID NO: 20, 22, 24, 26, 28, 41, 43, 45, 47, 49, 51, 53, 55, 57, 79, 59, 61, or 62. In certain embodiments the antibody or antigen binding fragment thereof comprises a VH amino acid sequence having 1, 2, 3, 4, 5, 6, 7, 8, 9, or 10 mutations (including additions, deletions, and substitutions, such as conservative substitutions) in the amino acid sequence of SEQ ID NO: 20, 22, 24, 26, 28, 41, 43, 45, 47, 49, 51, 53, 55, 57, 79, 59, 61, or 62. As used herein, a "conservative substitution" refers to the replacement of a first amino acid by a second amino acid that does not substantially alter the chemical, physical and/or functional properties of the antibody or antigen binding fragment thereof (e.g., the antibody or antigen binding fragment thereof retains the same charge, structure, polarity, hydrophobicity/hydrophilicity, and/or preserves functions such as the ability to bind alpha toxin and thereby reduce *S. aureus* virulence). In certain embodiments, the antibody or antigen binding fragment thereof comprises a VH amino acid sequence with a given percent identify to SEQ ID NO: 20, 22, 24, 26, 28, 41, 43, 45, 47, 49, 51, 53, 55, 57, 79, 59, 61, or 62 and has one or more of the following characteristics:

(a) disassociation constant ($K_D$) for *S. aureus* alpha toxin of about 13 nM or less;

(b) inhibits the formation of alpha toxin oligomers by at least 50%, 60%, 70%, 80%, 90% or 95% (or any percentage in between);

(c) reduces alpha toxin cytolytic activity by at least 50%, 60%, 70%, 80%, 90% or 95% (or any percentage in between) (e.g., as determined by cell lysis and hemolysis assays); or (d) reduces immune cell infiltration, bacterial burden, and pro-inflammatory cytokine release (e.g., in an animal pneumonia model).

In certain embodiments, an anti-secreted toxin antibody or antigen binding fragment thereof comprises a VL amino acid sequence comprising at least 65%, 70%, 75%, 80%, 85%, 90%, 95% or 100% (or any percentage in between) identity to the amino acid sequence of SEQ ID NO: 19, 21, 23, 25, 27, 42, 44, 46, 48, 50, 52, 54, 56, 58, 60 or 63. In various embodiments the antibody or antigen binding fragment thereof comprises a VL amino acid sequence having 1, 2, 3, 4, 5, 6, 7, 8, 9, or 10 mutations (including additions, deletions, and substitutions, such as conservative substitutions) in the amino acid sequence of SEQ ID NO: 19, 21, 23, 25, 27, 42, 44, 46, 48, 50, 52, 54, 56, 58, 60 or 63. In certain embodiments, the antibody or antigen binding fragment thereof comprises a VL amino acid sequence with a given percent identify to SEQ ID NO: 19, 21, 23, 25, 27, 42, 44, 46, 48, 50, 52, 54, 56, 58, 60 or 63 and has one or more of the following characteristics:

(a) disassociation constant ($K_D$) for *S. aureus* alpha toxin of about 13 nM or less;

(b) inhibits the binding of alpha toxin to the cell surface thereby disrupting formation of alpha toxin oligomers by at least 50%, 60%, 70%, 80%, 90% or 95% (or any percentage in between);

(c) reduces alpha toxin cytolytic activity by at least 50%, 60%, 70%, 80%, 90% or 95% (or any percentage in between) (e.g., as determined by cell lysis and hemolysis assays); or (d) reduces immune cell infiltration, bacterial burden, and pro-inflammatory cytokine release (e.g., in an animal pneumonia model).

In some embodiments, the isolated antibody or antigen-binding fragment specifically binds to a *Staphylococcus aureus* alpha toxin polypeptide and includes (a) a VH CDR1 comprising an amino acid sequence identical to, or comprising 1, 2, or 3 amino acid residue mutations relative to SEQ ID NO: 7, 10, 13 or 69; (b) a VH CDR2 comprising an amino acid sequence identical to, or comprising 1, 2, or 3 amino acid residue mutations relative to SEQ ID NO: 8, 11, 14, 17, 70 or 75; and/or (c) a VH CDR3 comprising an amino acid sequence identical to, or comprising 1, 2, or 3 amino acid residue mutations relative to SEQ ID NO: 9, 12, 15, 18, 16, 65, 66, 67, 71, 72, 76 or 78.

In particular embodiments, the isolated antibody or antigen-binding fragment that specifically binds to a *Staphylococcus aureus* alpha toxin polypeptide comprises a VH CDR1, VH CDR2 and VH CDR3 comprising amino acid sequences identical to, or comprising 1, 2, or 3 amino acid residue mutations in each CDR relative to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs: 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

In some embodiments, the isolated antibody or antigen-binding fragment thereof that specifically binds to a *Staphylococcus aureus* alpha toxin polypeptide includes (a) a VL CDR1 comprising an amino acid sequence identical to, or comprising 1, 2, or 3 amino acid residue mutations relative to SEQ ID NO: 1 or 4; (b) a VL CDR2 comprising an amino acid sequence identical to, or comprising 1, 2, or 3 amino acid residue mutations relative to SEQ ID NO: 2, 5, 73 or 77; and/or (c) a VL CDR3 comprising an amino acid sequence identical to, or comprising 1, 2, or 3 amino acid residue mutations relative to SEQ ID NO: 3, 6, 64, 68 or 74.

In particular embodiments, the isolated antibody or antigen-binding fragment thereof that specifically binds to a *Staphylococcus aureus* alpha toxin polypeptide comprises a VL CDR1, VL CDR2 and VL CDR3 comprising amino acid sequences identical to, or comprising 1, 2, or 3 amino acid residue mutations in each CDR relative to SEQ ID NOs: 1, 2 and 3; SEQ ID NOs: 4, 5 and 6; SEQ ID NOs: 1, 2 and 64; SEQ ID NOs: 1, 2 and 68; SEQ ID NOs: 1, 73 and 74; or SEQ ID NOs: 1, 77 and 74.

In some embodiments, the isolated antibody or antigen-binding fragment thereof that specifically binds to a *Staphylococcus aureus* alpha toxin polypeptide comprises a VH CDR1, VH CDR2, VH CDR3, VL CDR1, VL CDR2 and VL CDR3 comprising amino acid sequences identical to, or comprising 1, 2, or 3 amino acid residue mutations in each CDR relative to: (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; (c) a VH CDR3 comprising the amino acid sequence of SEQ ID NO: 9, 12, 15, 18, 16, 65, 66, 67, 71, 72, 76 or 78; (d) a VL CDR1 comprising the amino acid sequence of SEQ ID NO: 1 or 4; (e) a VL CDR2 comprising the amino acid sequence of SEQ ID NO: 2, 5, 73, or 77; or (f) a VL CDR3 comprising the amino acid sequence of SEQ ID NO: 3, 6, 64, 68 or 74.

In particular embodiments, the isolated antibody or antigen-binding fragment thereof that specifically binds to a *Staphylococcus aureus* alpha toxin polypeptide comprises a VH CDR1, VH CDR2, VH CDR3, VL CDR1, VL CDR2, and VL CDR3 comprising amino acid sequences identical to, or comprising 1, 2, or 3 amino acid residue mutations in each CDR relative to SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs; 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; or SEQ ID NOs: 69, 70, 71, 1, 77 and 74.

In some embodiments, provided is a composition that comprises an isolated antibody or antigen-binding fragment thereof that (i) includes a VH chain domain comprising three CDRs and a VL chain domain comprising three CDRs; and (ii) specifically binds to a *Staphylococcus aureus* alpha toxin polypeptide, where the three CDRs of the VH chain domain include (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; and (c) a VH CDR3 comprising the amino acid sequence of SEQ ID NO: 9, 12, 15, 18, 16, 65, 66, 67, 71, 72, 76 or 78. In particular embodiments, the VH CDR1, VH CDR2 and VH CDR3 correspond to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

In certain embodiments, an antibody or antigen binding fragment thereof specifically binds an *S. aureus* secreted toxin and comprises (a) a VH CDR1 comprising an amino acid sequence identical to, or comprising 1, 2, or 3 amino acid residue mutations relative to SEQ ID NO: 7, 10, 13 or 69; (b) a VH CDR2 comprising an amino acid sequence identical to, or comprising 1, 2, or 3 amino acid residue mutations relative to SEQ ID NO: 8, 11, 14, 17, 70 or 75; and (c) a VH CDR3 comprising an amino acid sequence identical to, or comprising 1, 2, or 3 amino acid residue mutations relative to SEQ ID NO: 9, 12, 15, 18, 16, 65, 66, 67, 71, 72, 76 or 78; (d) a VL CDR1 comprising the amino acid sequence of SEQ ID NO: 1 or 4; (e) a VL CDR2 comprising the amino acid sequence of SEQ ID NO: 2, 5, 73, or 77; and (f) a VL CDR3 comprising the amino acid sequence of SEQ ID NO: 3, 6, 64, 68 or 74 and has one or more of the following characteristics:

(a) dissociation constant ($K_D$) for alpha toxin of about 13 nM or less;

(b) binds to alpha toxin monomers;

(c) inhibits the formation of alpha toxin oligomers by at least 50%, 60%, 70%, 80%, 90% or 95% (or any percentage in between);

(d) reduces alpha toxin cytolytic activity by at least 50%, 60%, 70%, 80%, 90% or 95% (or any percentage in between) (e.g., as determined by cell lysis and hemolysis assays); or (e) reduces immune cell infiltration, bacterial burden and pro-inflammatory cytokine release (e.g., in animal pneumonia model).

In certain embodiments, an antibody or antibody fragment specifically binds to an *S. aureus* surface antigen or secreted toxin and comprises a heavy chain variable domain comprising at least 90% identity to the amino acid sequence of SEQ ID NO: 20, 22, 24, 26, 28, 41, 43, 45, 47, 49, 51, 53, 55, 57, 79, 59, 61, 62, 80, 82, 84, 86, or 88 and comprises a light chain variable domain comprising at least 90% identity to the amino acid sequence of SEQ ID NO: 19, 21, 23, 25, 27, 42, 44, 46, 48, 50, 52, 54, 56, 58, 60, 63, 81, 83, 85, 87, or 89. In further embodiments, the antibody or antigen binding fragment thereof reduces the ability of *S. aureus* to evade opsonophagocytosis by at least 50%. In further embodiments, the antibody or antigen binding fragment thereof reduces the concentration of *S. aureus* CFUs by at least 50%. In other embodiments, the antibody or antigen binding fragment thereof inhibits the binding of one or more alpha toxin monomers to each other (e.g., inhibits oligomerization) and/or reduces *S. aureus* virulence.

In some embodiments, the isolated antibody or antigen-binding fragment specifically binds to a *Staphylococcus aureus* alpha toxin polypeptide and includes (a) a VH CDR1 comprising an amino acid sequence identical to, or comprising 1, 2, or 3 amino acid residue mutations relative to SEQ ID NO: 7, 10, 13 or 69; (b) a VH CDR2 comprising an amino acid sequence identical to, or comprising 1, 2, or 3 amino acid residue mutations relative to SEQ ID NO: 8, 11, 14, 17, 70 or 75; and/or (c) a VH CDR3 comprising an amino acid sequence identical to, or comprising 1, 2, or 3 amino acid residue mutations relative to SEQ ID NO: 9, 12, 15, 18, 16, 65, 66, 67, 71, 72, 76 or 78.

In particular embodiments, the isolated antibody or antigen-binding fragment that specifically binds to a *Staphylococcus aureus* alpha toxin polypeptide comprises a VH CDR1, VH CDR2 and VH CDR3 comprising amino acid sequences identical to, or comprising 1, 2, or 3 amino acid residue mutations in each CDR relative to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

In some embodiments, the isolated antibody or antigen-binding fragment thereof that specifically binds to a *Staphylococcus aureus* alpha toxin polypeptide includes (a) a VL CDR1 comprising an amino acid sequence identical to, or comprising 1, 2, or 3 amino acid residue mutations relative to SEQ ID NO: 1 or 4; (b) a VL CDR2 comprising an amino acid sequence identical to, or comprising 1, 2, or 3 amino acid residue mutations relative to SEQ ID NO: 2, 5, 73 or 77;

and/or (c) a VL CDR3 comprising an amino acid sequence identical to, or comprising 1, 2, or 3 amino acid residue mutations relative to SEQ ID NO: 3, 6, 64, 68 or 74.

In particular embodiments, the isolated antibody or antigen-binding fragment thereof that specifically binds to a *Staphylococcus aureus* alpha toxin polypeptide comprises a VL CDR1, VL CDR2 and VL CDR3 comprising amino acid sequences identical to, or comprising 1, 2, or 3 amino acid residue mutations in each CDR relative to SEQ ID NOs: 1, 2 and 3; SEQ ID NOs: 4, 5 and 6; SEQ ID NOs: 1, 2 and 64; SEQ ID NOs: 1, 2 and 68; SEQ ID NOs: 1, 73 and 74; or SEQ ID NOs: 1, 77 and 74.

In some embodiments, the isolated antibody or antigen-binding fragment thereof that specifically binds to a *Staphylococcus aureus* alpha toxin polypeptide comprises a VH CDR1, VH CDR2, VH CDR3, VL CDR1, VL CDR2 and VL CDR3 comprising amino acid sequences identical to, or comprising 1, 2, or 3 amino acid residue mutations in each CDR relative to: (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; (c) a VH CDR3 comprising the amino acid sequence of SEQ ID NO: 9, 12, 15, 18, 16, 65, 66, 67, 71, 72, 76 or 78; (d) a VL CDR1 comprising the amino acid sequence of SEQ ID NO: 1 or 4; (e) a VL CDR2 comprising the amino acid sequence of SEQ ID NO: 2, 5, 73, or 77; or (f) a VL CDR3 comprising the amino acid sequence of SEQ ID NO: 3, 6, 64, 68 or 74.

In particular embodiments, the isolated antibody or antigen-binding fragment thereof that specifically binds to a *Staphylococcus aureus* alpha toxin polypeptide comprises a VH CDR1, VH CDR2, VH CDR3, VL CDR1, VL CDR2, and VL CDR3 comprising amino acid sequences identical to, or comprising 1, 2, or 3 amino acid residue mutations in each CDR relative to SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs: 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; or SEQ ID NOs: 69, 70, 71, 1, 77 and 74.

In some embodiments, provided is a composition that comprises an isolated antibody or antigen-binding fragment thereof that (i) includes a VH chain domain comprising three CDRs and a VL chain domain comprising three CDRs; and (ii) specifically binds to a *Staphylococcus aureus* alpha toxin polypeptide, where the three CDRs of the VH chain domain include (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; and (c) a VH CDR3 comprising the amino acid sequence of SEQ ID NO: 9, 12, 15, 18, 16, 65, 66, 67, 71, 72, 76 or 78. In particular embodiments, the VH CDR1, VH CDR2 and VH CDR3 correspond to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

In certain embodiments, the combination of CDR sequences present to form an anti-secreted toxin antibody include a VH CDR1 comprising SEQ ID NO: 7, 10, 13 or 69, a VH CDR2 comprising SEQ ID NO: 8, 11, 14, 17, 70 or 75 and a VH CDR3 comprising SEQ ID NO: SEQ ID NO: 9, 12, 15, 18, 16, 65, 66, 67, 71, 72, 76 or 78, as depicted in Table 9. In some embodiments, the VL CDR1 comprises SEQ ID NO: 1 or 4, the VL CDR2 comprises SEQ ID NO: 2, 5, 73, or 77 and the VL CDR3 comprises SEQ ID NO: 3, 6, 64, 68 or 74, as depicted in Table 9.

Antibodies and antigen binding fragments thereof, as disclosed herein, can comprise one or more amino acid sequences substantially the same as an amino acid sequences described herein. Amino acid sequences that are substantially the same include sequences comprising conservative amino acid substitutions, as well as amino acid deletions and/or insertions.

E. Framework Regions

Variable domains of the heavy and light chains each comprise at least one framework regions (FR1, FR2, FR3, FR4 or alternatively FW1, FW2, FW3, FW4). The framework regions of the heavy chain are here designated VH FR, while the framework regions of the light chain are here designated VL FR. In certain embodiments the framework regions can contain substitutions, insertions, or other alterations. In certain embodiments, these alterations result in an improvement or optimization in the binding affinity of the antibody. Non-limiting examples of framework region residues that can be modified include those that non-covalently bind antigen directly, interact with/effect the conformation of a CDR, and/or participate in the VL-VH interface.

In certain embodiments a framework region may comprise one or more amino acid changes for the purposes of "germlining." For example, the amino acid sequences of selected antibody heavy and light chains can be compared to germline heavy and light chain amino acid sequences and where certain framework residues of the selected VL and/or VH chains differ from the germline configuration (e.g., as a result of somatic mutation of the immunoglobulin genes used to prepare the phage library), it may be desirable to "back mutate" the altered framework residues of the selected antibodies to the germline configuration (i.e., change the framework amino acid sequences of the selected antibodies so that they are the same as the germline framework amino acid sequences). Such "back mutation" (or "germlining") of framework residues can be accomplished by standard molecular biology methods for introducing specific mutations (e.g., site-directed mutagenesis or PCR-mediated mutagenesis). In some embodiments, variable light and/or heavy chain framework residues are back mutated. In certain embodiments, a variable heavy chain of an isolated antibody or antigen-binding fragment disclosed presently is back mutated. In certain embodiments, a variable heavy chain of an isolated antibody or antigen-binding fragment comprises at least one, at least two, at least three, at least four or more back mutations.

In certain embodiments, the VH of an anti-alpha toxin antibody or antigen binding fragment thereof may comprise an FR1, FR2, FR3 and/or FR4 having amino acid sequences that are about 65% to about 100% identical to the corresponding VH framework regions within SEQ ID NO: 20, 22, 24, 26, 28, 41, 43, 45, 47, 49, 51, 53, 55, 57, 79, 59, 61, or 62. In some embodiments, an anti-alpha toxin antibody or antigen binding fragment thereof comprises a VH FR amino acid sequence (FR1, FR2, FR3 and/or FR4) at least 65%, 70%, 75%, 80%, 85%, 90%, 95% or 100% identical (or any percentage in between) to the corresponding FR regions of VH SEQ ID NO: 20, 22, 24, 26, 28, 41, 43, 45, 47, 49, 51, 53, 55, 57, 79, 59, 61, or 62. In certain embodiments an anti-alpha toxin antibody or antigen binding fragment thereof comprises a VH FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR of VH SEQ ID NO: 20, 22, 24, 26, 28, 41, 43, 45, 47, 49, 51, 53, 55, 57, 79, 59, 61, or 62.

In certain embodiments, an anti-alpha toxin antibody or antigen binding fragment thereof may comprise a VH FR (FR1, FR2, FR3 and/or FR4) comprising an amino acid sequence identical to, or comprising 1, 2 or 3 amino acid mutations relative to, the corresponding FR of VH SEQ ID NO: 20, 22, 24, 26, 28, 41, 43, 45, 47, 49, 51, 53, 55, 57, 79, 59, 61, or 62. In particular FR1, FR2, FR3 or FR4 of the VH may each have an amino acid sequence identical to or comprising 1, 2 or 3 amino acid mutations relative to the corresponding FR1, FR2, FR3 or FR4 of VH SEQ ID NO: 20, 22, 24, 26, 28, 41, 43, 45, 47, 49, 51, 53, 55, 57, 79, 59, 61, or 62.

In certain embodiments, the VL of an anti-alpha toxin antibody or antigen binding fragment thereof herein provided may comprise an FR1, FR2, FR3 and/or FR4 having amino acid sequences that are about 65% to about 100% identical to the corresponding framework regions within the FR of VL SEQ ID NO: 19, 21, 23, 25, 27, 42, 44, 46, 48, 50, 52, 54, 56, 58, 60 or 63. In some embodiments, an anti-alpha toxin antibody or antigen binding fragment thereof comprises a VL FR amino acid sequence (FR1, FR2, FR3 and/or FR4) at least 65%, 70%, 75%, 80%, 85%, 90%, 95% or 100% identical (or any percentage in between) to the corresponding FR of VL SEQ ID NO: 19, 21, 23, 25, 27, 42, 44, 46, 48, 50, 52, 54, 56, 58, 60 or 63. In certain embodiments an anti-alpha toxin antibody or antigen binding fragment thereof comprises a VL FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR of VL SEQ ID NO: 19, 21, 23, 25, 27, 42, 44, 46, 48, 50, 52, 54, 56, 58, 60 or 63.

In certain embodiments, an anti-alpha toxin antibody or antigen binding fragment thereof comprises a VL FR (FR1, FR2, FR3 and/or FR4) comprising an amino acid sequence identical to, or comprising 1, 2 or 3 amino acid mutations relative to, the corresponding FR of VL SEQ ID NO: 19, 21, 23, 25, 27, 42, 44, 46, 48, 50, 52, 54, 56, 58, 60 or 63. In particular FR1, FR2, FR3 or FR4 of the VL may each have an amino acid sequence identical to, or comprising 1, 2 or 3 amino acid mutations relative to, the corresponding FR1, FR2, FR3 or FR4 of VH SEQ ID NO: 19, 21, 23, 25, 27, 42, 44, 46, 48, 50, 52, 54, 56, 58, 60 or 63.

In certain embodiments, an isolated antibody or antigen-binding fragment that specifically binds an S. aureus secreted toxin comprises a VH FR (FR1, FR2, FR3 and/or FR4) comprising amino acid sequences identical to, or comprising 1, 2 or 3 amino acid mutations relative to, the corresponding FR of VH SEQ ID NO: 20, 22, 24, 26, 28, 41, 43, 45, 47, 49, 51, 53, 55, 57, 79, 59, 61, or 62 and/or VL FR (FR1, FR2, FR3 and/or FR4) comprising an amino acid sequence identical to, or comprising 1, 2 or 3 amino acid mutations relative to, the corresponding FR of VL SEQ ID NO: 19, 21, 23, 25, 27, 42, 44, 46, 48, 50, 52, 54, 56, 58, 60 or 63.

In certain embodiments, an isolated antibody or antigen-binding fragment thereof specifically binds an S. aureus secreted toxin and comprises a VH FR (FR1, FR2, FR3 and/or FR4) comprising an amino acid sequence identical to, or comprising 1, 2 or 3 amino acid mutations relative to, the corresponding FR of VH SEQ ID NO: 20, 22, 24, 26, 28, 41, 43, 45, 47, 49, 51, 53, 55, 57, 79, 59, 61, or 62 and/or VL FR (FR1, FR2, FR3 and/or FR4) comprising an amino acid sequence identical to, or comprising 1, 2 or 3 amino acid mutations relative to, the corresponding FR of VL SEQ ID NO: 19, 21, 23, 25, 27, 42, 44, 46, 48, 50, 52, 54, 56, 58, 60 or 63, and where the antibody has one or more of the following characteristics:

(a) affinity constant ($K_D$) for alpha toxin of about 13 nM or less;

(b) binds to alpha toxin monomers;

(c) inhibits the formation of alpha toxin oligomers by at least 50%, 60%, 70%, 80%, 90% or 95% (or any percentage in between);

(d) reduces alpha toxin cytolytic activity by at least 50%, 60%, 70%, 80%, 90% or 95% (or any percentage in between) (e.g., as determined by cell lysis and hemolysis assays); or (e) reduces immune cell infiltration, bacterial burden and pro-inflammatory cytokine release (e.g., in animal pneumonia model).

In certain embodiments, an isolated antibody or antigen-binding fragment that specifically binds the S. aureus IsdH surface antigen is provided, comprising VH FR1, FR2, FR3 and/or FR4 regions having amino acid sequences that are about 65% to about 100% identical to the corresponding amino acid sequences of the four VH framework regions within SEQ ID NOs: 80, 82, 84, 86, or 88. In some embodiments, the antibody or antigen binding fragment thereof comprises a VH FR amino acid sequence (FR1, FR2, FR3 and/or FR4) at least 65%, 70%, 75%, 80%, 85%, 90%, 95% or 100% identical (or any percentage in between) to the corresponding amino acid sequences of the four FR regions of VH SEQ ID NOs: 80, 82, 84, 86, or 88. In certain embodiments the antibody or antigen binding fragment thereof comprises a VH FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR regions of VH SEQ ID NOs: 80, 82, 84, 86, or 88.

In certain embodiments, an isolated antibody or antigen-binding fragment that specifically binds IsdH is provided, comprising VL FR1, FR2, FR3 and/or FR4 regions having amino acid sequences that are about 65% to about 100% identical to the corresponding amino acid sequences of the four VL framework regions within SEQ ID NOs: 81, 83, 85, 87, or 89. In some embodiments, the antibody or antigen binding fragment thereof comprises a VL FR amino acid sequence (FR1, FR2, FR3 and/or FR4) at least 65%, 70%, 75%, 80%, 85%, 90%, 95% or 100% identical (or any percentage in between) to the corresponding FR regions of VL SEQ ID NOs: 81, 83, 85, 87, or 89. In certain embodiments the antibody or antigen binding fragment thereof comprises a VL FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR regions of VL SEQ ID NOs: 81, 83, 85, 87, or 89.

In certain embodiments, an isolated antibody or antigen-binding fragment specifically binds IsdH and comprises a VH FR (FR1, FR2, FR3 and/or FR4) comprising an amino acid sequence identical to, or comprising 1, 2 or 3 amino acid mutations relative to, the corresponding FR of VH SEQ ID NO: 80, 82, 84, 86, or 88 and/or comprises a VL FR (FR1, FR2, FR3 and/or FR4) comprising an amino acid sequence identical to, or comprising 1, 2 or 3 amino acid mutations relative to, the corresponding FR of VL SEQ ID NO: 81, 83, 85, 87, or 89.

In certain embodiments, an isolated antibody or antigen-binding fragment that specifically binds IsdH is provided, comprising VH FR1, FR2, FR3 and/or FR4 regions having amino acid sequences that are about 65% to about 100% identical to the corresponding amino acid sequences of the four VH framework regions within SEQ ID NOs: 80, 82, 84, 86, or 88. In some embodiments, the antibody or antigen binding fragment thereof comprises a VH FR amino acid sequence (FR1, FR2, FR3 and/or FR4) at least 65%, 70%, 75%, 80%, 85%, 90%, 95% or 100% identical (or any percentage in between) to the corresponding amino acid sequences of the four FR regions of VH SEQ ID NOs: 80, 82, 84, 86, or 88. In certain embodiments the antibody or antigen binding fragment thereof comprises a VH FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR regions of VH SEQ ID NOs: 80, 82, 84, 86, or 88.

In certain embodiments, an isolated antibody or antigen-binding fragment that specifically binds IsdH is provided, comprising VL FR1, FR2, FR3 and/or FR4 regions having amino acid sequences that are about 65% to about 100% identical to the corresponding amino acid sequences of the four VL framework regions within SEQ ID NOs: 81, 83, 85, 87, or 89. In some embodiments, the antibody or antigen binding fragment thereof comprises a VL FR amino acid sequence (FR1, FR2, FR3 and/or FR4) at least 65%, 70%, 75%, 80%, 85%, 90%, 95% or 100% identical (or any percentage in between) to the corresponding FR regions of VL SEQ ID NOs: 81, 83, 85, 87, or 89. In certain embodiments the antibody or antigen binding fragment thereof comprises a VL FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR regions of VL SEQ ID NOs: 81, 83, 85, 87, or 89.

In certain embodiments, an isolated antibody or antigen-binding fragment specifically binds IsdH and comprises a VH FR (FR1, FR2, FR3 and/or FR4) comprising an amino acid sequence identical to, or comprising 1, 2 or 3 amino acid mutations relative to, the corresponding FR of VH SEQ ID NO: 80, 82, 84, 86, or 88 and/or comprises a VL FR (FR1, FR2, FR3 and/or FR4) comprising an amino acid sequence identical to, or comprising 1, 2 or 3 amino acid mutations relative to, the corresponding FR of VL SEQ ID NO: 81, 83, 85, 87, or 89.

In certain embodiments, an isolated antibody or antigen-binding fragment that specifically binds the S. aureus ClfA surface antigen is provided, comprising VH FR1, FR2, FR3 and/or FR4 regions having amino acid sequences that are about 65% to about 100% identical to the corresponding amino acid sequences of the four VH framework regions within SEQ ID NOs: 132 or 140. In some embodiments, the antibody or antigen binding fragment thereof comprises a VH FR amino acid sequence (FR1, FR2, FR3 and/or FR4) at least 65%, 70%, 75%, 80%, 85%, 90%, 95% or 100% identical (or any percentage in between) to the corresponding amino acid sequences of the four FR regions of VH SEQ ID NOs: 132 or 140. In certain embodiments the antibody or antigen binding fragment thereof comprises a VH FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR regions of VH SEQ ID NOs: 132 or 140.

In certain embodiments, an isolated antibody or antigen-binding fragment that specifically binds ClfA is provided, comprising VL FR1, FR2, FR3 and/or FR4 regions having amino acid sequences that are about 65% to about 100% identical to the corresponding amino acid sequences of the four VL framework regions within SEQ ID NOs: 136 or 144. In some embodiments, the antibody or antigen binding fragment thereof comprises a VL FR amino acid sequence (FR1, FR2, FR3 and/or FR4) at least 65%, 70%, 75%, 80%, 85%, 90%, 95% or 100% identical (or any percentage in between) to the corresponding FR regions of VL SEQ ID NOs: 136 or 144. In certain embodiments the antibody or antigen binding fragment thereof comprises a VL FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR regions of VL SEQ ID NOs: 136 or 144.

In certain embodiments, an isolated antibody or antigen-binding fragment specifically binds ClfA and comprises a VH FR (FR1, FR2, FR3 and/or FR4) comprising an amino acid sequence identical to, or comprising 1, 2 or 3 amino acid mutations relative to, the corresponding FR of VH SEQ ID NO: 132 or 136 and/or comprises a VL FR (FR1, FR2, FR3 and/or FR4) comprising an amino acid sequence identical to, or comprising 1, 2 or 3 amino acid mutations relative to, the corresponding FR of VL SEQ ID NO: 136 or 144.

In certain embodiments, an isolated antibody or antigen-binding fragment that specifically binds ClfA is provided, comprising VH FR1, FR2, FR3 and/or FR4 regions having amino acid sequences that are about 65% to about 100% identical to the corresponding amino acid sequences of the four VH framework regions within SEQ ID NOs: 132 or 140. In some embodiments, the antibody or antigen binding fragment thereof comprises a VH FR amino acid sequence (FR1, FR2, FR3 and/or FR4) at least 65%, 70%, 75%, 80%, 85%, 90%, 95% or 100% identical (or any percentage in between) to the corresponding amino acid sequences of the four FR regions of VH SEQ ID NOs: 132 or 140. In certain embodiments the antibody or antigen binding fragment thereof comprises a VH FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR regions of VH SEQ ID NOs: 132 or 140.

In certain embodiments, an isolated antibody or antigen-binding fragment that specifically binds IsdH is provided, comprising VL FR1, FR2, FR3 and/or FR4 regions having amino acid sequences that are about 65% to about 100% identical to the corresponding amino acid sequences of the four VL framework regions within SEQ ID NOs: 136 or 144. In some embodiments, the antibody or antigen binding fragment thereof comprises a VL FR amino acid sequence (FR1, FR2, FR3 and/or FR4) at least 65%, 70%, 75%, 80%, 85%, 90%, 95% or 100% identical (or any percentage in between) to the corresponding FR regions of VL SEQ ID NOs: 136 or 144. In certain embodiments the antibody or antigen binding fragment thereof comprises a VL FR amino acid sequence (FR1, FR2, FR3 and/or FR4) at least 90%, 91%, 92%, 93%, 94%, 95%, 96%, 97%, 98%, 99% or 100% identical (or any percentage in between) to the corresponding FR regions of VL SEQ ID NOs: 136 or 144.

In certain embodiments, an isolated antibody or antigen-binding fragment specifically binds ClfA and comprises a VH FR (FR1, FR2, FR3 and/or FR4) comprising an amino acid sequence identical to, or comprising 1, 2 or 3 amino acid mutations relative to, the corresponding FR of VH SEQ ID NO: 132 or 140 and/or comprises a VL FR (FR1, FR2, FR3 and/or FR4) comprising an amino acid sequence identical to, or comprising 1, 2 or 3 amino acid mutations relative to, the corresponding FR of VL SEQ ID NO: 136 or 144.

F. Nucleotide Sequences Encoding Anti-Alpha Toxin Antibodies and Antigen Binding Fragments Thereof In addition to the amino acid sequences described above, further provided are nucleotide sequences corresponding to the amino acid sequences disclosed herein. In some embodiments, a nucleotide sequence encodes an antibody or antigen binding fragment thereof directed against an S. aureus surface antigen or secreted toxin. The nucleotide sequences are provided in Example 7, Table 8. Thus, also provided are polynucleotide sequences encoding VH and VL regions, including FR regions and CDRs, for the antibodies or fragments described herein, as well as expression vectors for their efficient expression in cells (e.g., mammalian cells).

Also disclosed herein are polynucleotides substantially identical to those coding for the amino acid sequences disclosed herein. Substantially identical sequences may be polymorphic sequences, i.e., alternative sequences or alleles in a population. Substantially identical sequences may also comprise mutagenized sequences, including sequences comprising silent mutations. A mutation may comprise one or more residue changes, a deletion of one or more residues, or an insertion of one or more additional residues. Substantially identical sequences may also comprise various nucleotide sequences that encode for the same amino acid at any given amino acid position in an amino acid sequence disclosed herein, due to the degeneracy of the nucleic acid code.

Also disclosed herein are polynucleotides that hybridize under highly stringent or lower stringency hybridization conditions to polynucleotides that encode an antibody or antigen binding fragment thereof directed against an S. aureus surface antigen or secreted toxin. The term "stringency" as used herein refers to experimental conditions (e.g., temperature and salt concentration) of a hybridization experiment to denote the degree of homology between two nucleic acids; the higher the stringency, the higher percent homology between the two nucleic acids. As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary.

Stringent hybridization conditions include, but are not limited to, hybridization to filter-bound DNA in 6× sodium chloride/sodium citrate (SSC) at about 45 degrees Celsius, followed by one or more washes in 0.2×SSC/0.1% SDS at about 50-65 degrees Celsius. Other stringent conditions include hybridization to filter-bound DNA in 6×SSC at about 45 degrees Celsius followed by one or more washes in 0.1×SSC/0.2% SDS at about 65 degrees Celsius. Other hybridization conditions of known stringency are familiar to one of skill and are included herein.

In certain embodiments, a nucleic acid disclosed herein may encode the amino acid sequence of an antibody or antigen binding fragment thereof directed against an S. aureus surface antigen or secreted toxin, or the nucleic acid may hybridize under stringent conditions to a nucleic acid including a nucleotide sequence that encodes the amino acid sequence of the antibody or antigen binding fragment thereof.

In certain embodiments, a polynucleotide sequence may comprise a nucleotide sequence encoding an amino acid sequence of an antibody or antigen binding fragment thereof capable of binding an S. aureus surface antigen or secreted toxin and which is at least about 65%, 70%, 75%, 80%, 85%, 90%, 95% or 100% identical (or any percentage in between) to the VH amino acid sequence of SEQ ID NO: 20, 22, 24, 26, 28, 41, 43, 45, 47, 49, 51, 53, 55, 57, 79, 59, 61, 62, 80, 82, 84, 86, or 88. In certain embodiments, a polynucleotide sequence may comprise a nucleotide sequence encoding an amino acid sequence having 1, 2, 3, 4, 5, 6, 7, 8, 9, or 10 mutations (including additions, deletions, and substitutions, such as conservative substitutions) in the amino acid sequence of SEQ ID NO: 20, 22, 24, 26, 28, 41, 43, 45, 47, 49, 51, 53, 55, 57, 79, 59, 61, 62, 80, 82, 84, 86, or 88. In some embodiments, a polynucleotide sequence may comprise a nucleotide sequence encoding an amino acid sequence of an antibody or antigen binding fragment thereof capable of binding an S. aureus surface antigen or secreted toxin and which is at least about 65%, 70%, 75%, 80%, 85%, 90%, 95% or 100% identical (or any percentage in between) to a VH nucleotide sequence of SEQ ID NO: 30, 32, 34, 36, 38, 120, 122, 124, 126, or 128.

In certain embodiments, a polynucleotide sequence may comprise a nucleotide sequence encoding an amino acid sequence of an antibody or antigen binding fragment thereof capable of binding an S. aureus surface antigen or secreted toxin and which is at least about 65%, 70%, 75%, 80%, 85%, 90%, 95% or 100% identical (or any percentage in between) to the VL amino acid sequence of SEQ ID NO: 19, 21, 23, 25, 27, 42, 44, 46, 48, 50, 52, 54, 56, 58, 60, 63, 81, 83, 85, 87, or 89. In certain embodiments, a polynucleotide sequence may comprise a nucleotide sequence encoding an amino acid sequence having 1, 2, 3, 4, 5, 6, 7, 8, 9, or 10 mutations (including additions, deletions, and substitutions, such as conservative substitutions) in the amino acid sequence of SEQ ID NO: 19, 21, 23, 25, 27, 42, 44, 46, 48, 50, 52, 54, 56, 58, 60, 63, 81, 83, 85, 87, or 89. In some embodiments, the polynucleotide sequence may comprise a nucleotide sequence encoding an amino acid sequence of an antibody or antigen binding fragment thereof capable of binding an S. aureus surface antigen or secreted toxin and which is at least about 65%, 70%, 75%, 80%, 85%, 90%, 95% or 100% identical (or any percentage in between) to a VL nucleotide sequence of SEQ ID NO: 29, 31, 33, 35, 37, 121, 123, 125, 127, or 129.

In particular embodiments, a polynucleotide sequence may comprise a nucleotide sequence encoding an amino acid sequence of an antibody or antigen binding fragment thereof capable of binding an S. aureus surface antigen or secreted toxin and which is at least about 65%, 70%, 75%, 80%, 85%, 90%, 95% or 100% identical (or any percentage in between) to a VH amino acid sequence and at least about 65%, 70%, 75%, 80%, 85%, 90%, 95% or 100% identical (or any percentage in between) to a VL amino acid sequence, where the VH and VL sequences are represented by SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63; SEQ ID NOs: 80 and 81; SEQ ID NOs: 82 and 83; SEQ ID NOs: 84 and 85; SEQ ID NOs: 86 and 87; SEQ ID NOs: 88 and 89.

The disclosed polynucleotides may be obtained, and the nucleotide sequence of the polynucleotides determined, by any method known in the art. For example, if the nucleotide sequence of an antibody is known, a polynucleotide encoding the antibody may be assembled from chemically synthesized oligonucleotides. This would involve, for example, the synthesis of overlapping oligonucleotides containing portions of the sequence encoding the antibody, annealing and ligating of those oligonucleotides, and then amplification of the ligated oligonucleotides by PCR. The disclosed polynucleotides can also be generated from any suitable source of nucleic acids, such as an antibody cDNA library, or a cDNA library isolated from any tissue or cells expressing the antibody (e.g., from hybridoma cells selected to express an antibody).

G. Functional Characteristics of Antibodies or Fragments Directed Against S. aureus Surface Antigens or Secreted Toxins In certain embodiments, an antibody or antigen binding fragment thereof directed against an S. aureus surface antigen alters the biological properties of S. aureus cells that express the surface antigen. In various embodiments, the antibody binds an S. aureus surface antigen, thereby enhancing opsonophagocytosis by host cells. In further embodiments, opsonophagocytosis is increased by 50%, 60%, 70%, 80%, 90%, or 95% (or any percentage in between), as measured by an opsonophagocytic killing assay. In some embodiments, binding of the antibody to the surface determinant antigen prevents interaction between the surface antigen and a surface adhesin, thereby reducing the concentration of colony forming units (CFUs) present in a host tissue, as measured in a mouse bacteremia model. In further embodiments, the CFU concentration is reduced by 50%, 60%, 70%, 80%, 90% or 95% (or any percentage in between), as compared to the CFU concentration in the presence of a negative control antibody or in the absence of the antibody or antigen binding fragment thereof. For example, an anti-IsdH antibody may reduce CFU concentration by 50%, 60%, 70%, 80%, 90% or 95% (or any percentage in between). In some embodiments, an anti-surface antigen antibody can compete with haptoglobin and/or hemoglobin for binding to S. aureus, thereby inhibiting the ability of S. aureus to access and utilize the iron within hemoglobin. In certain embodiments, antibodies or fragments directed against a surface antigen reduce the ability of S. aureus to bind haptoglobin and/or hemoglobin by 20%, 30%, 40%, 50%, 60%, 70%, 80%, 90% or 95% (or any percentage in between), as compared to S. aureus binding in the absence of antibody. For example, an anti-IsdH antibody can reduce the ability of S. aureus to bind haptoglobin and/or hemoglobin by 20%, 30%, 40%, 50%, 60%, 70%, 80%, 90% or 95% (or any percentage in between).

As used herein, an "opsonophagocytic killing assay" (OPK) refers to any assay used to measure the percentage of phagocytic killing induced in a host tissue in vitro following addition of an antibody to a sample of tissue containing S. aureus of known concentration. This reduction in CFU is normalized against a control level of OPK observed in the presence of a control antibody. The assay measures the ability of a target antibody to induce complement activation and subsequent phagocytosis. For example, the OPK can comprise combining 10 µl of antibody and 10 µl of S. aureus ($10^6$ cells/ml), followed by adding 10 µl of human promyelocytic leukemia (HL-60) cells ($10^7$ cells/ml) and 10 µl of human sera pre-absorbed against S. aureus. 10 µl of the mixture can then be plated (at time $T_0$), followed by cell lysis using 1% saponin (at time $T_{60}$) and determination of S. aureus CFU concentration. Percentage killing can be calculated as follows: $100 \times (1-(T_{60}/T_0))$, where $T_{60}$ refers to the CFU concentration at the end of the assay (i.e., at 60 minutes) and $T_0$ refers to the CFU concentration at the beginning of the assay.

As used herein, a "bacteremia model" refers to any in vivo model of S. aureus infection used to evaluate the impact of an antibody on S. aureus bacterial burden, expressed as a percent reduction in CFUs. For example, the bacteremia model can comprise injecting an antibody into a mouse, subsequently injecting $10^8$ CFU of S. aureus intraperitoneally, and later collecting blood and measuring the CFU concentration, as compared to the CFU concentration after injecting a control antibody.

In certain embodiments, an anti-alpha toxin antibody or antigen binding fragment thereof alters the biological properties of alpha toxin and/or alpha toxin expressing cells. In some embodiments, an anti-alpha toxin antibody or antigen binding fragment thereof neutralizes the biological activity of alpha toxin by binding to the polypeptide and inhibiting membrane binding and the assembly of alpha toxin monomers into a transmembrane pore (e.g., alpha toxin heptamer). Neutralization assays can be performed using methods known in the art using, in some circumstances, commercially available reagents. Neutralization of alpha toxin often is measured with an IC50 of $1 \times 10^{-6}$ M or less, $1 \times 10^{-7}$ M or less, $1 \times 10^{-8}$ M or less, $1 \times 10^{-9}$ M or less, $1 \times 10^{-10}$ M or less and $1 \times 10^{-11}$ M or less. The term "inhibitory concentration 50%" (abbreviated as "IC50") represents the concentration of an inhibitor (e.g., an anti-alpha toxin antibody or antigen binding fragment thereof provided herein) that is required for 50% inhibition of a given activity of the molecule the inhibitor targets (e.g., alpha toxin oligomerization to form a transmembrane pore heptamer complex). A lower IC50 value generally corresponds to a more potent inhibitor.

In certain embodiments, an anti-alpha toxin antibody or antigen binding fragment thereof inhibits one or more biological activities of alpha toxin. The term "inhibition" as used herein, refers to any statistically significant decrease in biological activity, including full blocking of the activity. For example, "inhibition" can refer to a decrease of about 10%, 20%, 30%, 40%, 50%, 60%, 70%, 80%, 90%, or 100% in biological activity, or any percentage in between. In certain embodiments, an anti-alpha toxin antibody or antigen binding fragment thereof inhibits one or more biological activities of alpha toxin by at least 10%, 20%, 30%, 40%, 50%, 60%, 70%, 80%, 90%, or 100%, or any percentage in between.

In some embodiments, an anti-alpha toxin antibody or antigen binding fragment thereof may deplete alpha toxin secreted by pathogenic S. aureus. In some embodiments, an anti-alpha toxin antibody or antigen binding fragment thereof may achieve at least about 20%, at least about 30%, at least about 40%, at least about 50%, at least about 60%, at least about 70%, at least about 80%, at least about 90%, at least about 95%, or about 100% depletion of alpha toxin secreted by S. aureus, or any percentage in between. In particular embodiments, virtually all detectable secreted alpha toxin is depleted from cells infected with S. aureus.

In certain embodiments, an anti-alpha toxin antibody or antigen binding fragment thereof may inhibit the expression of one or more inducible genes that respond directly or indirectly to the environment created by an S. aureus infection and/or alpha toxin expression and function. In specific embodiments, an anti-alpha toxin antibody or antigen binding fragment thereof inhibits the expression of one or more inducible genes that responds directly or indirectly to the environment created by S. aureus alpha toxin expression and function by at least 20%, by at least 30%, by at least 40%, by at least 50%, by at least 60%, by at least 70%, by at least 80%, or by at least 90%, or any percentage in between.

H. Methods of Making Antibodies Against *S. aureus* Surface Antigens and Secreted Toxins The following describes exemplary techniques for the production of the antibodies disclosed herein. In some embodiments, recombinant or hybridoma methods can be used to generate antibodies or fragments disclosed herein. In other embodiments, antibodies or antibody fragments can be isolated from antibody phage libraries generated using techniques known in the art. Other techniques for preparing antibodies, known in the art, can also be used to prepare antibodies against *S. aureus* surface antigens and secreted toxins.

In some embodiments, anti-IsdH antibodies can be generated using native *S. aureus* IsdH, mutant IsdH, a variant, or an antigenic fragment of IsdH. *S. aureus* cells expressing IsdH can also be used to generate antibodies. IsdH, for use in producing anti-IsdH antibodies, can also be produced recombinantly in an isolated form from bacterial or eukaryotic cells using standard recombinant DNA methodology.

Polyclonal antibodies to a secreted toxin or surface antigen, such as IsdH, can be produced by various procedures known in the art. For example, an IsdH polypeptide or immunogenic fragment thereof can be administered to various host animals via subcutaneous or intraperitoneal injections of the relevant antigen to induce the production of sera containing polyclonal antibodies specific for the antigen. Host animals include, but are not limited to, rabbits, mice, and rats. In some embodiments, various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Other adjuvants known in the art may also be used.

Monoclonal antibodies to a secreted toxin or surface antigen, such as IsdH, can be prepared using a wide variety of techniques known in the art, including the use of hybridoma, recombinant, and phage display technologies, or a combination thereof. The term "monoclonal antibody" as used herein refers to an antibody obtained from a population of substantially homogeneous or isolated antibodies, e.g., the individual antibodies comprising the population are identical except for possible naturally occurring mutations that may be present in minor amounts. The modifier "monoclonal" is not to be construed as requiring production of the antibody by any particular method. Monoclonal antibodies include monoclonal mammalian, chimeric, humanized, human, domain, diabodies, vaccibodies, linear and multispecific antibodies.

Once an antibody disclosed herein has been produced, it may be purified by any method known in the art for purification of an immunoglobulin molecule, for example, by chromatography (e.g., ion exchange, affinity, and sizing column chromatography), centrifugation, differential solubility, or by any other technique for the purification of proteins. Further, the antibodies of the present technology or fragments thereof may be fused to heterologous polypeptide sequences (including epitope "tags" and other fusion proteins such as GST fusions) to facilitate antibody purification and use in subsequent assays.

In certain embodiments, the antibodies disclosed herein are chimeric antibodies. Chimeric antibodies are antibodies in which a portion of the heavy and/or light chain is identical with or homologous to corresponding sequences in antibodies derived from a particular species or belonging to a particular antibody class or subclass, while another portion of the chain(s) is identical with or homologous to corresponding sequences in antibodies derived from another species or belonging to another antibody class or subclass, as well as fragments of such antibodies, so long as they exhibit the desired biological activity. Chimeric antibodies disclosed herein include "primatized" antibodies comprising variable domain antigen-binding sequences derived from a nonhuman primate (e.g., Old World Monkey, such as baboon, rhesus or cynomolgus monkey) and human constant region sequences. Chimeric antibodies disclosed herein also include humanized antibodies, which are generated using methods known in the art.

In other embodiments, the antibodies disclosed herein are human antibodies and are generated using methods known in the art. For example, fully human antibodies can be generated through the introduction of nucleic acids encoding functional human antibody loci into a rodent or other animal so that the rodent or other animal produces fully human antibodies. In another example, human antibodies can be derived by in vitro methods. Suitable examples include but are not limited to phage display, ribosome display, yeast display, and other methods known in the art. Additional examples of methods for making human antibodies or fragments directed against *S. aureus* surface antigens or secreted toxins include the VelocImmune® mouse technology (Regeneron Pharmaceuticals). See, e.g., U.S. Pat. No. 6,596,541 (incorporated by reference in its entirety).

In certain embodiments, it may be desirable to revert a framework sequence of an antibody disclosed herein to the germline sequence, revert a CDR to germline, and/or remove a structural liability. Thus, in some embodiments, where a particular antibody disclosed herein differs from its respective germline sequence at the amino acid level, the antibody sequence can be mutated back to the germline sequence. Such corrective mutations can occur at one, two, three or more positions, or a combination of any of the mutated positions, using standard molecular biological techniques.

In certain embodiments, the present disclosure encompasses antibody fragments or antibodies comprising these fragments. The antibody fragment comprises a portion of the full length antibody, which generally is the antigen binding or variable region thereof. Examples of such antibody fragments include Fab, Fab', F(ab')2, Fd and Fv fragments; diabodies; linear antibodies, single-chain antibody molecules; and multispecific antibodies are antibodies formed from these antibody fragments.

In addition to the above described human, humanized and/or chimeric antibodies, the antibodies disclosed herein can also be further modified to comprise one or more of the following: at least one amino acid residue and/or polypeptide substitution, addition and/or deletion in the VL domain and/or VH domain and/or Fc region, and post translational modifications. Any combination of deletion, insertion, and substitution can be made to arrive at a final construct, provided that the final construct possesses desired characteristics.

Included in these modifications are antibody conjugates where an antibody has been covalently attached to a moiety. Moieties suitable for attachment to the antibodies include but are not limited to, proteins, peptides, drugs, labels, and cytotoxins. These changes to the antibodies may be made to alter or optimize antibody characteristics (e.g., biochemical, binding and/or functional) as is appropriate for detection, diagnosis, and/or treatment of *S. aureus* infection and related diseases or disorders. Methods for forming conjugates, making amino acid and/or polypeptide changes, and post-translational modifications are known in the art. Also included in these modifications are fusion proteins, i.e., the antibody, or a fragment thereof, fused to a heterologous protein, polypeptide, or peptide.

In certain embodiments, antibodies or fragments directed against *S. aureus* surface antigens or secreted toxins are produced to comprise an altered Fc region (also referred to herein as "variant Fc region") in which one or more alterations have been made in the Fc region in order to change functional and/or pharmacokinetic properties of the antibodies. Such alterations may result in altered effector function, reduced immunogenicity, and/or an increased serum half life. In certain embodiments, effector function of an antibody can be modified through changes in the Fc region, including but not limited to, amino acid substitutions, amino acid additions, amino acid deletions and changes in post translational modifications to Fc amino acids (e.g., glycosylation).

In some embodiments an Fc variant antibody is prepared that has altered binding properties for an Fc ligand (e.g., an Fc receptor such as C1q) relative to a native Fc antibody. Examples of binding properties include but are not limited to, binding specificity, equilibrium dissociation constant ($K_a$), dissociation and association rates ($k_{off}$ and $k_{on}$ respectively), binding affinity and/or avidity.

In certain embodiments, the antibodies disclosed herein are glycosylated in order to alter effector function of antibodies or to alter the affinity of the antibody for a target antigen. In some embodiments, the glycosylation pattern in the variable region of the present antibodies is modified. For example, an aglycosylated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid mutations can be made that result in elimination of one or more variable region framework glycosylation sites to thereby eliminate glycosylation at that site.

In certain embodiments, the antibodies disclosed herein are conjugated or covalently attached to another substance using methods known in the art. In some embodiments, the attached substance is a detectable label (also referred to herein as a reporter molecule) or a solid support. Suitable substances for attachment to antibodies include, but are not limited to, an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a virus, a fluorophore, a chromophore, a dye, a toxin, a hapten, an enzyme, an antibody, an antibody fragment, a radioisotope, solid matrixes, semi-solid matrixes and combinations thereof. Methods for conjugation or covalently attaching another substance to an antibody are known in the art.

I. Methods of Treatment Using *S. aureus* Surface Antigen or Secreted Toxin Antibodies or Fragments The antibodies or fragments disclosed herein can be administered individually, in combination with each other, or in combination with additional pharmaceutical agents such as antibiotics, for the prevention of *S. aureus* infections and related symptoms and conditions (e.g., to treat the hyperinflammation induced by alpha toxin). The antibodies and combinations of antibodies or fragments can be used to treat or prevent a wide range of conditions/diseases, including both chronic and acute conditions, such as, but not limited to, bacteremia, burns, cellulitis, dermonecrosis, eyelid infections, food poisoning, joint infections, neonatal conjunctivitis, osteomyelitis, pneumonia, skin infections, surgical wound infection, scalded skin syndrome, endocarditis, meningitis, abscess formation and toxic shock syndrome. Further detail regarding potential diseases/conditions suitable for *S. aureus* therapy are provided below.

In certain embodiments, at least one antibody disclosed herein can be administered in combination with at least one additional therapeutic agent (e.g., an antibiotic). Examples of antibiotics that can be administered in the combination include: penicillin, oxacillin, flucloxacillin, vancomycin and gentamicin. In certain embodiments, combination therapy using an antibiotic and at least one antibody or antigen binding fragment thereof disclosed herein enhances treatment efficacy by, for example, reducing *S. aureus* CFU concentration in a host tissue, reducing the ability of *S. aureus* to evade opsonophagocytosis, and/or reducing *S. aureus* virulence, as compared to antibody therapy alone.

Combinations therapy (e.g., treatment or prevention with more than one antibody) can provide benefit over individual therapy by providing multiple non-overlapping *S. aureus* therapeutic targets. For example, an antibody targeting a secreted toxin can neutralize the harmful effects of the toxin, such as the hyperinflammation induced by alpha toxin. At the same time, a co-administered antibody targeting a surface antigen (e.g., IsdH) can inhibit *S. aureus* colony growth and opsonophagocytic evasion, which are not altered by the antibody targeting the secreted toxin. Combination therapy can also ensure that therapy will be effective against a broader range of *S. aureus* strains or mutants, some of which may lack an antigenic target for a particular antibody.

In particular combination therapy can comprise one or more antibodies or antigen binding fragments thereof that specifically bind to a surface determinant, such as SdrC, SdrD, SdrE, ClfA, ClfB, IsdA, IsdB, IsdC, IsdE, IsdH, or PNAG and one or more antibodies or antigen binding fragments thereof that bind to a secreted toxin, such as alpha toxin (AT). In particular embodiments, combination therapy can comprise an antibody or antigen binding fragment thereof that specifically binds to IsdH and an antibody or antigen binding fragment thereof that specifically binds to AT; an antibody or antigen binding fragment thereof that specifically binds to ClfA and an antibody or antigen binding fragment thereof that specifically binds to AT; an antibody or antigen binding fragment thereof that specifically binds to IsdH and an antibody or antigen binding fragment thereof that specifically binds to AT; an antibody or antigen binding fragment thereof that specifically binds to ClfA and an antibody or antigen binding fragment thereof that specifically binds to IsdH; or an antibody or antigen binding fragment thereof that specifically binds to IsdH, an antibody or antigen binding fragment thereof that specifically binds to ClfA and an antibody or antigen binding fragment thereof that specifically binds to AT. In particular embodiments, the combination therapy can comprise an antibody or antigen binding fragment thereof that specifically binds to IsdH and an antibody or antigen binding fragment thereof that specifically binds to AT, where the anti-IsdH antibody or fragment thereof comprises the VH and/or VL, or a VH CDR1, VH CDR2, VH CDR3, VL CDR1, VL CDR2 and VLCDR3 of mAb 2F4, and where the anti-AT antibody or fragment thereof comprises the VH and/or VL, or a VH CDR1, VH CDR2, VH CDR3, VL CDR1, VL CDR2 and VLCDR3 of mAb LC10 or comprises SEQ ID NO: 130 and SEQ ID NO: 131.

In particular embodiments, the anti-AT antibodies or antigen binding fragments thereof can comprise a VH and/or VL, or a VH CDR1, VH CDR2, VH CDR3, VL CDR1, VL CDR2 and VLCDR3 of any of the antibodies listed in Table 7 or 10, the anti-IsdH or antigen binding fragments thereof can comprise a VH and/or VL, or a VH CDR1, VH CDR2, VH CDR3, VL CDR1, VL CDR2 and VLCDR3 of any of the antibodies listed in Table 12 and the anti-ClfA antibodies or antigen binding fragments thereof can comprise a VH and/or VL, or a VH CDR1, VH CDR2, VH CDR3, VL CDR1, VL CDR2 and VLCDR3 of any of the antibodies listed in Table 14.

In various embodiments, the disclosed antibodies, combinations of antibodies, and/or combinations of antibodies and antibiotics can be administered therapeutically to treat an *S. aureus* infection or as prophylaxis to prevent infection. For example, combination therapy can be administered prior to surgery to prevent *S. aureus* complication, or after surgery to treat an *S. aureus* infection acquired during surgery.

Pharmaceutical compositions for use in treating *S. aureus* infections or as prophylaxis are also provided herein. In several embodiments, a pharmaceutical composition comprises at least one antibody disclosed herein and a pharmaceutically acceptable carrier. The term "pharmaceutically acceptable carrier" means one or more non-toxic materials that do not interfere with the effectiveness or biological activity of the active ingredients. Such preparations may contain salts, buffering agents, preservatives, compatible carriers, and optionally other therapeutic agents. Such pharmaceutically acceptable preparations may also contain compatible solid or liquid fillers, diluents or encapsulating substances which are suitable for administration into a human. The term "carrier" denotes an organic or inorganic ingredient, natural or synthetic, with which the active ingredient is combined to facilitate pharmaceutical administration.

Therapeutic compositions of the present technology may be formulated for a particular dosage. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the selected dosage is suitable for intravenous, intramuscular, intranasal, oral, topical or subcutaneous delivery. The amount of active ingredient which can be combined with a carrier material to produce a single dosage form will vary depending upon the subject being treated, and the particular mode of administration.

Also disclosed herein is a pharmaceutical kit for therapeutic use in treating an *S. aureus* infection or as prophylaxis against such an infection. In some embodiments, the kit comprises one or more containers filled with a sterile therapeutic liquid formulation or lyophilized formulation comprising at least one antibody or antigen binding fragment thereof disclosed herein and a pharmaceutically-acceptable carrier. In some embodiments, the container filled with the liquid formulation is a pre-filled syringe. In other embodiments, the container filled with sterile lyophilized powder formulation is suitable for reconstitution and subsequent administration. In certain embodiments, the formulations comprise antibodies and antigen binding fragments thereof recombinantly fused or chemically conjugated to at least one other moiety, including but not limited to, a heterologous protein, a heterologous polypeptide, a heterologous peptide, a large molecule, a small molecule, a marker sequence, a diagnostic or detectable agent, a therapeutic moiety, a drug moiety, a radioactive metal ion, a second antibody, and a solid support. In certain embodiments, the formulations are formulated in single dose vials as sterile liquids. In some embodiments, the formulation is supplied in a pre-filled syringe.

J. Diseases Associated with *S. aureus* Infection

Antibodies and antigen binding fragments thereof, as disclosed herein, can be used for detecting, diagnosing, preventing and/or treating a disease associated with an *S. aureus* infection. The antibodies can also be used to alleviate and/or prevent one or more symptoms of a disease associated with an *S. aureus* infection.

Provided also herein is a method for preventing, treating or managing pneumonia in a subject, including: administering a composition that includes an isolated antibody or antigen-binding fragment thereof that immunospecifically binds to a *S. aureus* toxin or surface determinant, or a combination thereof, to a subject in need thereof in an amount effective for preventing, treating or managing the pneumonia.

As used herein, the terms "treat," "treating" or "treatment" refer to therapeutic treatment and prophylactic or preventative measures, wherein the object is to prevent or slow down (lessen) an undesired physiological change or disorder, such as the progression of the disease. Beneficial or desired clinical results include, but are not limited to, alleviation of symptoms, diminishment of extent of disease, stabilized (i.e., not worsening) state of disease, delay or slowing of disease progression, amelioration or palliation of the disease state. "Treatment" can also mean prolonging survival as compared to expected survival if not receiving treatment. Those in need of treatment include those already with the condition or disorder as well as those prone to have the condition or disorder or those in which the condition or disorder is to be prevented.

Provided in some embodiments is a method for preventing, treating or managing a skin infection condition in a subject that includes: administering a composition that includes an isolated antibody or antigen-binding fragment thereof that immunospecifically binds to a *S. aureus* toxin or surface determinant, or a combination thereof according to the present invention to a subject in need thereof in an amount effective for preventing, treating or managing the skin infection condition. In certain embodiments, the skin infection condition is dermonecrosis. In some embodiments, the skin infection condition includes a *S. aureus* infection of the skin. In certain embodiments, the method prevents the skin infection condition.

In some embodiments, provided is a method for preventing, treating or managing a *S. aureus* infection associated with dialysis treatment, high-risk surgery, pneumonia, ventilator-associated pneumonia (VAP), or reinfection after prior release from a hospital for previous treatment or surgery that includes administering a composition that includes an isolated antibody or antigen-binding fragment thereof that immunospecifically binds to a *S. aureus* toxin or surface determinant, or a combination thereof, to a subject in need thereof.

Also provided in some embodiments is a method for preventing, treating or managing a condition associated with *S. aureus* infection that includes administering a composition that includes an isolated antibody or antigen-binding fragment thereof that immunospecifically binds to a *S.*

*aureus* toxin or surface determinant to a subject in need thereof, in an amount effective to reduce cell lysis. In certain embodiments, the method prevents a condition associated with *S. aureus* infection. In some embodiments, the cell is an erythrocyte from the blood or the lung.

Provided herein are methods for preventing or reducing the severity of *S. aureus*-associated sepsis in a mammalian subject comprising administering to the subject an effective amount of an isolated an isolated antibody or antigen-binding fragment thereof that immunospecifically binds to a *S. aureus* toxin or surface determinant, or a combination thereof. Also provided are methods of reducing *S. aureus* bacterial load in the bloodstream or heart of a mammalian subject comprising administering to the subject an effective amount of an isolated antibody or antigen-binding fragment thereof that immunospecifically binds to a *S. aureus* toxin or surface determinant, or a combination thereof. Methods of reducing *S. aureus* bacterial agglutination and/or thromboembolic lesion formation in a mammalian subject comprising administering to the subject an effective amount of an isolated antibody or antigen-binding fragment thereof that immunospecifically binds to a *S. aureus* toxin or surface determinant, or a combination thereof, are also provided.

Methods of preventing *S. aureus*-associated sepsis in a mammalian subject suitably comprise administering an effective amount of an isolated antibody or antigen-binding fragment thereof that immunospecifically binds to a *S. aureus* toxin or surface determinant, or a combination thereof, to the subject prior to an infection event. As used herein, "infection event" refers to an event during which the subject is, or could be, exposed to *S. aureus* infection. Exemplary infection events include, but are not limited to, surgery on any part of the body, including head, mouth, hands, arms, legs, trunk, internal organs (e.g., heart, brain, bowels, kidneys, stomach, lungs, liver, spleen, pancreas, etc.), bones, skin. Surgery provides conditions, such as open surgical wounds and organs, which can readily be infected with *S. aureus*. Additional infection events include trauma to any part of the body that provides open wounds or otherwise access to the bloodstream via which *S. aureus* infection could enter the body. Additional infection events include blood transfusions, injections of medications or illegal or legal drugs, needle pricks, tattoo needles, insertion and maintenance of intravenous (IV) lines, insertion and maintenance of surgical drains, and sites of skin breakdown e.g., bedsores (decubitus ulcers).

In embodiments where the methods provide prevention of *S. aureus*-associated sepsis, the isolated antibody or antigen-binding fragment thereof that immunospecifically binds to a *S. aureus* toxin or surface determinant, or a combination thereof, is suitably administered at least 1 hour prior to an infection event. For example, at least 1 hour prior to surgery (the infection event). Suitably, the isolated antibody or antigen-binding fragment thereof that immunospecifically binds to a *S. aureus* toxin or surface determinant, or a combination thereof, is administered at least 6 hours, at least 12 hours, at least 18 hours, at least 24 hours, at least 30 hours, at least 36 hours, at least 42 hours, at least 48 hours, or longer, prior to the infection event. In embodiments, the isolated antibody or antigen-binding fragment thereof that immunospecifically binds to a *S. aureus* toxin or surface determinant, or a combination thereof, is suitably administered about 6 hours to about 36 hours, about 6 hours to about 36 hours, about 12 hours to about 36 hours, about 12 hours to about 24 hours, about 24 hours to about 36 hours, about 20 hours to about 30 hours, about 20 hours to about 28 hours, about 22 hours to about 26 hours, or about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, or about 30 hours, or about 31 hours, or about 32 hours, or about 33 hours, or about 34 hours, or about 35 hours, or about 36 hours, prior to the infection event.

As used herein "prevention" of *S. aureus*-associated sepsis refers to reducing the risk of a subject acquiring *S. aureus*-associated sepsis at the time of the infection event. Suitably, the risk of a subject acquiring *S. aureus*-associated sepsis is reduced by at least 30% as compared to a subject that has not been administered an isolated antibody or antigen-binding fragment thereof that immunospecifically binds to a *S. aureus* toxin or surface determinant, or a combination thereof, prior to the infection event. More suitably the risk is reduced by at least 40%, at least 50%, at least 60%, at least 70%, at least 80%, at least 90% or the risk is completely eliminated as compared to a subject that has not been administered an isolated antibody or antigen-binding fragment thereof that immunospecifically binds to a *S. aureus* toxin or surface determinant, or a combination thereof, prior to the infection event.

In methods for reducing the severity of *S. aureus*-associated sepsis in a mammalian subject, such methods suitably comprise administering an effective amount of an isolated antibody or antigen-binding fragment thereof that immunospecifically binds to a *S. aureus* toxin or surface determinant, or a combination thereof, thereof to a subject that is exhibiting symptoms of *S. aureus*-associated sepsis. Such symptoms can include, for example, chills, confusion or delirium, fever or low body temperature (hypothermia), light-headedness due to low blood pressure, rapid heartbeat, shaking, skin rash and warm skin.

As used herein "reducing the severity" as it is used with reference to sepsis refers to reducing the symptoms that a subject that has acquired *S. aureus*-associated sepsis is exhibiting. Suitably, the symptoms are reduced by at least 30% as compared to the symptoms that a subject that also has acquired *S. aureus*-associated sepsis is exhibiting, but the subject has not been administered an isolated antibody or antigen-binding fragment thereof that immunospecifically binds to a *S. aureus* toxin or surface determinant, or a combination thereof. More suitably the symptoms are is reduced by at least 40%, at least 50%, at least 60%, at least 70%, at least 80%, at least 90% or the symptoms are completely eliminated (i.e., the subject is cured of the infection and the sepsis) as compared to a subject that has not been administered an isolated antibody or antigen-binding fragment thereof that immunospecifically binds to a *S. aureus* toxin or surface determinant, or a combination thereof prior to the infection event.

Non-limiting examples of some common conditions caused by *S. aureus* infection include burns, cellulitis, dermonecrosis, eyelid infections, food poisoning, joint infections, pneumonia, skin infections, surgical wound infection, scalded skin syndrome and toxic shock syndrome. In addition, it is a frequent pathogen in foreign body infections, such as intravascular lines, pacemakers, artificial heart valves and joint implants. Some of the conditions or diseases caused by *S. aureus* are described further below. Some or all of the conditions and diseases described below may involve the direct action of secreted toxins as a component of infection or mediator of the condition or disease state, while some or all of the conditions may involve the indirect or secondary action of secreted toxins (e.g., as primary virulence factors that cause the main symptom or majority of symptoms associated with the condition, or as agents that act to further advance the disease through disruption of cellular function or cell lysis).

a) Burns

Burn wounds are often sterile initially. However, moderate and severe burns generally compromise physical and immune barriers to infection (e.g., blistering, cracking or peeling of the skin), causing a loss of fluid and electrolytes and result in local or general physiological dysfunction. Contact of the compromised skin with viable bacteria can result in mixed colonization at the injury site. Infection may be restricted to the non-viable debris on the burn surface ("eschar"), or the colonization may progress into full skin infection and invade viable tissue below the eschar. More severe infections may reach below the skin, enter into the lymphatic system and/or blood circulation, and develop into septicemia. *S. aureus* typically is found among the pathogens that colonize burn wound infections. *S. aureus* can destroy granulation tissue and produce severe septicemia.

b) Cellulitis

Cellulitis is an acute infection of the skin that often begins as a superficial infection that can spread below the cutaneous layer. Cellulitis is most commonly caused by a mixed infection of *S. aureus* in conjunction with *S. pyogenes*. Cellulitis can lead to systemic infection.

c) Dermonecrosis

Dermonecrosis is an infection of the skin and subcutaneous tissues, easily spreading across the fascial plane within the subcutaneous tissue. The condition causes the upper and/or lower layers of skin to become necrotic, and can spread to underlying and surrounding tissues.

d) Necrotizing Fasciitis

Necrotizing fasciitis is referred to as "flesh-eating disease" or "flesh eating bacteria syndrome." Necrotizing fasciitis can be caused by a polymicrobial infection (e.g., type I, caused by a mixed bacterial infection), or by a monomicrobial infection (e.g., type II, caused by a single pathogenic strain of bacteria). Many types of bacteria can cause necrotizing fasciitis, non-limiting examples of which include; Group A *streptococcus* (e.g., *Streptococcus pyogenes*), *Staphylococcus aureus, Vibrio vulnificus, Clostridium perfringens*, and *Bacteroides fragilis*. Individuals with depressed or compromised immune systems are more likely to suffer from dermonecrosis (e.g., necrotizing fasciitis).

Historically, Group A *streptococcus* was diagnosed as the cause of the majority of cases of Type II dermonecrotic infections. However, since 2001, methicillin-resistant *Staphylococcus aureus* (MRSA) has been observed with increasing frequency as the cause of monomicrobial necrotizing fasciitis. The infection begins locally, sometimes at a site of trauma, which may be severe (such as the result of surgery), minor, or even non-apparent. Patients usually complain of intense pain that may seem in excess given the external appearance of the skin. With progression of the disease, tissue becomes swollen, often within hours. Diarrhea and vomiting are also common symptoms.

Sign of inflammation may not be apparent in the early stages of infection, if the bacteria are deep within the tissue. If the bacteria are not deep, signs of inflammation, such as redness and swollen or hot skin, show quickly. Skin color may progress to violet, and blisters may form, with subsequent necrosis (e.g., death) of the subcutaneous tissues. Patients with necrotizing fasciitis typically have a fever and appear very ill. Mortality rates have been noted as high as 73 percent if left untreated.

e) Pneumonia

*S. aureus* has also been identified as a cause of Staphylococcal pneumonia. Staphylococcal pneumonia causes inflammation and swelling of the lung, which in turn causes fluid to collect in the lung. Fluid collecting in the lung can prevent oxygen from entering the bloodstream. Those with influenza are at risk for developing bacterial pneumonia. *Staphylococcus aureus* is the most common cause of bacterial pneumonia in those already suffering from influenza. Common symptoms of staphylococcal pneumonia include coughing, difficulty breathing, and fever. Additional symptoms include fatigue, yellow or bloody mucus, and chest pain that worsens with breathing. Methicillin resistant *S. aureus* (MRSA) is increasingly being diagnosed as the strain identified in staphylococcal pneumonia.

f) Surgical Wound Infections

Surgical wounds often penetrate far into the body. Infection of such wounds thus pose a grave risk to a patient, if the wound becomes infected. *S. aureus* is frequently a causative agent of infections in surgical wounds. *S. aureus* is unusually adept at invading surgical wounds, sutured wounds can be infected by far fewer *S. aureus* cells then are necessary to cause infection in normal skin. Invasion of surgical wounds can lead to severe *S. aureus* septicemia. Invasion of the blood stream by *S. aureus* can lead to seeding and infection of internal organs, particularly heart valves and bone, causing systemic diseases, such as endocarditis and osteomyelitis.

g) Scalded Skin Syndrome

*S. aureus* is likely a major causative agent of "scalded skin syndrome," also referred to as "staphylococcal scalded skin syndrome," "toxic epidermal necrosis," "localized bullous impetigo," "Ritter's disease" and "Lyell's disease." Scalded skin syndrome frequently occurs in older children, typically in outbreaks caused by flowering of *S. aureus* strains that produce epidermolytic exotoxins (e.g., exfoliatin A and B, sometimes referred to as scalded skin syndrome toxin), which cause detachment within the epidermal layer. One of the exotoxins is encoded by the bacterial chromosome and the other is encoded by a plasmid. The exotoxins are proteases that cleave desmoglein-1, which normally holds the granulosum and spinosum layers of the skin together.

The bacteria may initially infect only a minor lesion, however, the toxin destroys intercellular connections, spreads epidermal layers and allows the infection to penetrate the outer layer of the skin, producing the desquamation that typifies the disease. Shedding of the outer layer of skin generally reveals normal skin below, but fluid lost in the process can produce severe injury in young children if it is not treated properly.

h) Toxic Shock Syndrome

Toxic shock syndrome (TSS) is caused by strains of *S. aureus* that produce the so-called "toxic shock syndrome toxin." The disease can be caused by *S. aureus* infection at any site, but is often erroneously viewed exclusively as a disease solely of women who use tampons. The disease involves toxemia and septicemia, and can be fatal.

Symptoms of toxic shock syndrome vary depending on the underlying cause. TSS resulting from infection with the bacteria *Staphylococcus aureus* typically manifests in otherwise healthy individuals with high fever, accompanied by low blood pressure, malaise and confusion, which can rapidly progress to stupor, coma, and multi-organ failure. The characteristic rash, often seen early in the course of illness, resembles a sunburn, and can involve any region of the body, including the lips, mouth, eyes, palms and soles.

In patients who survive the initial onslaught of the infection, the rash desquamates, or peels off, after 10-14 days.

As noted above, due to the increase of multi-drug resistant strains of *S. aureus*, an increasing number of antibiotics commonly used to treat *S. aureus* infections, no longer control or eliminate infections of methicillin- and multidrug-resistant *Staphylococcus aureus*. Antibodies against *S. aureus* surface determinants and secreted toxins, as described herein, can help reduce the severity of infection and also may aid in clearing, preventing (prophylactically) or reducing pathogenic *S. aureus* from an infected host. The antibodies can also be used to detect *S. aureus* and, when in a patient sample, diagnose *S. aureus* infections.

K. Methods of Detecting *S. aureus* Using Antibodies or Fragments Directed Against *S. aureus* Surface Antigens or Secreted Toxins In various embodiments, the antibodies disclosed herein can be used individually or in combination to detect the presence of *S. aureus* in a sample.

In certain embodiments, the method comprises contacting a test sample with one of the isolated antibodies or fragments disclosed herein. The antibody or antigen binding fragment thereof then bind to an *S. aureus* surface antigen or secreted toxin to form an antigen-antibody complex. In further embodiments, the method comprises contacting the antigen-antibody complex with a detectable label, wherein the signal produced by the detectable label is directly correlated with the presence of *S. aureus* in the sample. For example, the detectable label can comprise one or more fluorescent markers that bind the antibody or antigen in the antibody-antigen complex, such that an increase in fluorescence correlates with an increased concentration of *S. aureus* or secreted toxin in a sample.

In other embodiments, the detectable label competes with the *S. aureus* surface antigen or secreted toxin for binding to the antibody or antigen binding fragment thereof, wherein the signal produced by the detectable label is indirectly correlated with the concentration of *S. aureus* or secreted toxin in the sample. For example, the detectable label can comprise one or more fluorescent markers that compete with the surface antigen or secreted toxin for antibody binding, such that a decrease in fluorescence correlates with an increased concentration of *S. aureus* or secreted toxin in a sample In certain embodiments, the detectable signal produced by the detectable label in the test sample is compared to the signal from at least one control sample having a known concentration of antigen and antibody. In embodiments using control samples, antibody-antigen complex is detected in the control and test samples using the detectable label, and any statistically significant difference in the detectable signal between the samples is indicative of the concentration, presence, or absence of *S. aureus* and/or secreted toxin in the test sample.

In other embodiments, a combination of antibodies is used to detect *S. aureus* in a sample. In various embodiments, the method comprises contacting a test sample with an isolated antibody or antigen binding fragment thereof directed against an *S. aureus* surface antigen and an isolated antibody or antigen binding fragment thereof directed against an *S. aureus* secreted toxin. The combination of antibodies or fragments then bind to an *S. aureus* surface antigen and a secreted toxin to form two antigen-antibody complexes. In further embodiments, the method comprises contacting the test sample containing the antigen-antibody complexes with at least one detectable label, wherein the signal produced by the detectable label(s) is directly correlated with the presence of *S. aureus* in the sample. For example, the detectable label(s) can comprise one or more fluorescent markers that bind the antibody or antigen in at least one of the antibody-antigen complexes, such that an increase in fluorescence correlates with an increased concentration of *S. aureus* and/or secreted toxin in a sample.

In other embodiments, the at least one detectable label competes with the *S. aureus* surface antigen and/or secreted toxin for binding to the combination of antibodies or fragments. The signal produced by the detectable label(s) is thus indirectly correlated with the concentration of *S. aureus* in the sample. For example, the detectable label(s) can comprise one or more fluorescent markers that compete with the surface antigen and/or secreted toxin for antibody binding, such that a decrease in fluorescence correlates with an increased concentration of *S. aureus* and/or secreted toxin in a sample.

In certain embodiments, the detectable signals produced by the detectable labels in the test sample are compared to the signal from at least one control sample having known concentrations of antigens and antibodies. In embodiments using control samples, antibody-antigen complexes are detected in the control and test samples using the detectable labels, and any statistically significant difference in the detectable signals between the samples is indicative of the concentration, presence, or absence of *S. aureus* and/or secreted toxin in the test sample.

In certain embodiments, the method of detection is used to detect the presence of *S. aureus* in a patient sample, and the method further comprises diagnosing a patient with an *S. aureus* infection. In some embodiments, the method is adapted for use in an automated or semi-automated system.

In certain embodiments, kits comprising at least one antibody or antigen binding fragment thereof disclosed herein are also provided that are useful for various research and diagnostic purposes. For example, the kits can be used to detect *S. aureus* in a sample, or to immunoprecipitate an *S. aureus* secreted toxin. For isolation and purification purposes, the kit may contain an antibody or antigen binding fragment thereof coupled to a bead (e.g., sepharose beads).

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

EXAMPLES

The following examples serve to illustrate, and in no way limit, the present disclosure.

Example 1—Materials and Methods

Materials and methods utilized for Example 2 to Example 9 are provided hereafter Neutralization of Hemolytic Activity Fifty microliters of each B cell hybridoma culture supernatant was mixed with recombinant alpha toxin-His (rAT-his, 0.1 µg/ml final concentration) in 96 well plates, followed by the addition of 50 µl of 5% rabbit red blood cells (RBC) in PBS. Control wells contained RBC and culture media alone with or without AT. Plates were incubated for 1 h at 37° C., and the intact cells pelleted by centrifugation. 50 µl of the supernatants were transferred to a new 96 well plate and the $A_{490}$ measured in a spectrophotometer. Neutralizing activity was calculated relative to lysis with RBC and rAT-his alone and calculated: % inhibition=100×[100−($A_{490}$ nAT+Ab)/($A_{490}$ nAT no Ab)].

Inhibition with the purified mAbs also was tested. Anti-AT mAbs were added to a 96-well plate at about 80 µg/mL in PBS and the samples serially diluted (twofold) in PBS to a final volume of 50 µL. A nonspecific IgG1 (R347) was included as an isotype control. Twenty five microliters of mAb dilutions were mixed with 25 µL of nAT (native alpha toxin) at about 0.1 µg/mL in 96 well round bottom plates, followed by the addition of 50 µL 5% RBC. Inhibition of hemolytic activity was calculated as above.

Neutralization of A549 Lysis

A549 cells were maintained in a 5% $CO_2$ 37° C. incubator in RMPI supplemented with non essential amino acid, glutamine and 10% fetal bovine serum. Cells were washed once with Hank's balanced media, and plated at $10^4$/well under 50 µl in RPMI, 5% FBS, and incubated at 37° C. with 5% $CO_2$ for 20 hr. Anti-AT mAbs were added to a 96-well plate at 80 µg/mL in RPMI and the samples serially diluted (two-fold) in RPMI. An irrelevant IgG1 (R347) was included as an isotype control. In a separate 96-well plate, 30 µl of the diluted antibodies were mixed with 30 µl of nAT (final concentration, 5 µg/ml). Fifty microliters from each well was transferred to the plate containing adherent A549 cells. Control wells of A549 cells with or without nAT were included. Plates were incubated 37° C. with 5% $CO_2$ for 3 h, centrifuged and 50 µl supernatant transferred to a new 96-well plate. Cell lysis was measured as the release of lactate dehydrogenase (LDH) using a Cytotox 96 non radioactive assay kit (Promega) following the manufacturer's protocol. Background LDH was subtracted from each well and the inhibition of LDH release calculated: % inhibition=100×[100−($A_{590}$ nAT+Ab)/($A_{590}$ nAT no Ab)].

Neutralization of THP-1 Lysis

THP-1 cells were maintained in a 5% $CO_2$ 37° C. incubator in RPMI medium (Invitrogen) supplemented with non essential amino acids (Invitrogen), 2 mM glutamine (Invitrogen) and 10% fetal bovine serum (Invitrogen). Anti-AT mAbs were added to a 96-well plate at 80 µg/ml in RPMI and the samples serially diluted (two-fold) in RPMI to a final volume of 50 µL. An irrelevant IgG1 (R347) was included as an isotype control. Twenty five microliters of the mAb dilutions were mixed with 25 µl native alpha toxin (nAT) at 1.5 µg/ml final, followed by the addition of 50 µl of RMPI washed THP-1 cells ($10^6$ cells/ml in RPMI with 10% FBS) in a 96-well plate. Control wells consisted in THP-1 cells with alone or with nAT. Plates were incubated in a 5% $CO_2$ 37° C. incubator for 3 h, centrifuged and 50 µl of the supernatant transferred to a new 96 well plate. Cell lysis was measured as the release of lactate dehydrogenase (LDH) using the Cytotox 96 non radioactive assay kit (Promega) following the manufacturer's instructions. Inhibition of LDH release was calculated as described above.

Murine Pneumonia Model

Twenty-four hours prior to infection groups of ten 7-9 wk-old C57BL/6J mice (Harlan) received 0.5 ml of mAb at the concentrations indicated via i.p injection. The animals were then anesthetized with isofluorane, held vertically and 0.05 ml of S. aureus bacterial suspension ($1\times10^8$ CFU to $3\times10^8$ CFU) in sterile PBS were inoculated into the left and right nostrils. Animals were placed into a cage in a supine position for recovery and were observed twice daily for the time course of study. Animal survival was monitored for a maximum of 6 days.

Alternatively, animals were euthanized by $CO_2$ inhalation 48 h after bacterial infection. A lung and kidney were removed into sterile PBS, homogenized, diluted and plated for bacterial enumeration. Statistical significance of mortality studies was determined using log-rank test. The significance of bacterial recovery from organs was calculated using analysis of variance and Dunnett's post-test.

Murine Model of Dermonecrosis

Groups of five 6-8 weeks old female BALB/c mice (Harlan) were shaved on their back and administered by intraperitoneal injection of 0.5 ml IgG at the concentration indicated on the graph. Twenty-four hours later, the mice were infected by subcutaneous injection of 50 µL of a bacterial suspension ($1\times10^8$ S. aureus). The animals were monitored twice daily for signs of infection and the size of the abscess measured at the same time daily. The area of the lesions was calculated using the formula A=L×W. Statistical significance was determined using analysis of variance and Dunnett's post-test.

Murine Model of Sepsis

Preparation of Bacteria Challenge Dose: S. aureus SF8300 (USA300) was provided by Binh Diep (University California San Francisco). Bacteria were cultured overnight at 37° C. in 50 mL of tryptic soy broth (TSB) shaking at 250 rpm. Ten mL from the overnight culture were added to 1 L of fresh TSB and the bacteria grown at 37° C. with shaking to an optical density at 600 nm (OD600) of 0.8. Bacteria were recovered by centrifugation at 8000 rpm for 15 min at 4° C. and washed in phosphate buffer saline (PBS). The bacteria was collected by centrifugation and resuspended in PBS with 10% glycerol to a final bacterial stock concentration of ~$2\times10^{10}$ cfu/mL.

Mouse Challenge and Survival: Groups of ten 8-9 week old female BALB/c mice were injected intra-peritoneally (IP) with LC10 at indicated concentrations or R347 (45 mg/kg) mAbs in 500 µL PBS. Animals were then challenged intravenously (IV) in the tail vein 24 h later with 200 µL of a bacterial suspension ($5\times10^7$ cfu diluted in PBS, pH 7.2, from frozen stock). Mice were monitored for survival for 14 days post challenge. Statistical analysis was assessed with a logrank test: R347 (control) versus LC10 (anti-AT Ab) immunized animals.

Bacterial Load in Heart: Infected mice were euthanized with CO2 14 h post infection. The heart was removed, homogenized in lysing matrix A tubes in 1 mL cold PBS, and plated on TSA plates for bacterial enumeration. The bacterial load in heart tissue was analyzed in pairwise comparison between R347 and LC10 mAbs with an unpaired two-tailed Student's t-test. Data were considered significant if $p<0.05$.\

Bacteria Load in Blood: Animals were euthanized with CO2 at 8, 24, 48, 72, and 144 h post infection. Blood was collected by cardiac puncture, and 100 µL was plated immediately on a TSB plate for cfu enumeration. Data were analyzed with an unpaired student t test. Values were considered statistically different between LC10 and R347 mAbs if $p<0.05$.

Receptor Binding Assay

Red blood cell ghosts were prepared by incubating 5 mL of washed and packed rabbit red blood cells (RBC) in 500 mL of lysis buffer (5 mM phosphate, 1 mM EDTA, pH 7.4) o/n at 4° C. with constant stirring. Tim ghosts were then removed by centrifugation at 15,000×g and washed 3× with lysis buffer. They were then washed in PBS and resuspended in a final volume of 3 mL.

To assess binding of nAT to cell membranes RBC ghosts were diluted to $OD_{600}$ approximately 0.2 in PBS and 50 µL were coated onto ½-well 96 well plates (Costar) and incubated overnight at 4° C. The liquid was then removed from the plates and the wells were blocked with 100 µL of 1% BSA in PBS, pH7.4 for 2 hr at 4° C. and washed 3× with PBS. A 20 molar excess of IgG was mixed with nAT at 3 µg/mL and 50 µL was added to the blocked plates. The plates were incubated at 4° C. for 2 hr and washed 3× with PBS. Biotin labeled rabbit anti-AT IgG was added to the wells at 1 mg/mL and incubated at 4° C. for 1 hr, washed 3× and incubated with streptavidin peroxidase conjugate (1:30,000, Jackson Immunoresearch). The wells were washed 3× and developed with Sure Blue Reserve (KPL, Inc.). The $A_{450}$ was read using a plate reader (Molecular Devices) and the % AT bound calculated. % AT bound=100×($A_{450}$–AT+IgG/$A_{450}$–AT alone).

Measurement of Kinetic Rate and Binding Constants ($K_D$)

Kinetic rate constants ($k_{on}$, $k_{off}$) for the binding of the anti-AT IgG antibodies to purified nAT were measured employing an IgG-capture assay format on a BIAcore 3000 instrument (BIAcore, Inc). Briefly, a rat anti-mouse-IgG was immobilized on a CM5 sensor chip according to manufacturer's instructions. The final surface density of the capture reagent on the sensor chip was approximately 2500 response units (RUs), as described herein. A reference flow cell surface was also prepared on this sensor chip using the identical immobilization protocol, and omitting nAT. Anti-AT IgG antibodies were prepared at 20 nM in instrument buffer (HBS-EP buffer containing 0.01 M HEPES, pH 7.4, 0.15 M NaCl, 3 mM EDTA and 0.005% P-20) along with two-fold serial dilutions of the nAT. nAT serial dilutions were made in the range of about 0.78 nM to about 50 nM, in instrument buffer.

A sequential approach was utilized for kinetic measurements. Each anti-AT IgG was first injected over the capture and reference surfaces at a flow rate of 50 µL/min. Once the binding of the captured IgG had stabilized, a single concentration of the nAT protein was injected over both surfaces, at a flow rate of 50 µL/min. The resultant binding response curves was used to determine the association phase data. Following the injection of the nAT, the flow was then switched back to instrument buffer for 10 minutes to permit the collection of dissociation phase data followed by a 1 minute pulse of 10 mM glycine, pH 1.5 to regenerate the IgG capture surface on the chip. Binding responses from duplicate injections of each concentration of nAT were recorded against all anti-AT IgGs.

Additionally, several buffer injections were interspersed throughout the injection series. Select buffer injections were used along with the reference cell responses to correct the raw data sets for injection artifacts and/or non-specific binding interactions commonly referred to as "double-referencing" (D. G. Myszka, Improving biosensor analysis. *J. Mol. Recognit.* 12 (1999), pp. 279-284). Fully corrected binding data was then globally fit to a 1:1 binding model (BIAevaluation 4.1 software, BIAcore, Inc, Uppsala, Sweden) that included a term to correct for mass transport-limited binding, should it be detected. These analyses determined the kinetic rate (on, off) constants, from which the apparent $K_D$ was then calculated as $k_{off}/k_{on}$.

Measurement of Cytokine Levels in *S. aureus* Infected Lungs

Seven to nine wk-old C57BL/6J mice were treated with 2A3.1 hu (fully human 2A3.1) or R347 (45 mg/kg) by intraperitoneal injection 24 h before intranasal infection with $1.5×10^8$ cfu USA300 (BAA-1556, ATCC). Four and twenty-four hours post infection the mice were euthanized and the lungs were flushed 3× with 1 ml of PBS. The bronchoalveolar lavage fluid (BAL) was stored at –70° C. Proinflammatory cytokines were quantified using the 7 pro-inflammatory II mouse cytokine kit (Mesoscale, Gaithersburg, Md.) according to manufacturer's instructions. Cytokine levels were expressed as pg/ml.

Dot Blot Assays

Overlapping peptides spanning amino acid 40 to 293 were chemically synthesized (New England Peptide). Synthesis of $AT_{1-50}$ was attempted but not successful. Alpha toxin (AT), AT peptides and AT fragments (1 µg) were spotted on nitrocellulose and blocked 10 min with Blocker Casein in PBS. The blots were then probed with 2 µg/mL of the individual IgG for 3 hr at room temperature. The blots were washed and incubated with an alkaline phosphatase conjugated goat anti-mouse or goat anti rabbit IgG (1:1000, Caltag Laboratories) for 1 hr and developed using BCIP/NBT membrane phosphatase substrate system (KPL, Inc).

Example 2—Target Selection and Validation

Thirteen surface antigens and four secreted toxins were selected for validation as antibody targets, based on their conservation across clinical isolates and/or published vaccine potential. Included in this group were alpha toxin and three soluble modulins (PSMs). Also included were 8 staphylococcal cell wall-anchored antigens/adhesins. Five of the selected targets have homologues in *S. aureus* and *S. epidermidis*. These targets are involved in nutrient acquisition, biofilm formation, and cell division. Antibodies against alpha toxin were targeted as a hypothesized method to reduce or neutralize toxin activities such as tissue damage and immune dysregulation. Also targeted were *S. aureus* surface determinants (IsdH, SdrC, ClfB, ClfA and IsdB), which are important for *S. aureus* colonization, immune evasion, and fitness. A potential approach considered for enhancing antibody therapy involved combining opsonic and toxin-neutralizing monoclonal antibodies.

Antibodies raised against the identified targets were assessed in both in vitro and in vivo assays for reduced virulence and/or reduced colonization and immune evasion. Target fitness was also validated via active/passive immunization in murine infection models.

Example 3—Identification of Anti-IsdH Antibodies

A primary target identified was the *S. aureus* Iron regulated surface determinant H (IsdH). IsdH contains a 7 amino acid loop between the B1b and B2β-sheets, and this 7 amino acid loop is conserved across several members of the iron regulated surface determinants family, including in IsdA and IsdB. Mutations in this 7 amino acid loop reduce the ability of *S. aureus* to bind haemoglobin by greater than 100 fold and also impair the ability of *S. aureus* to evade phagocytic killing. Visai et al., *J. Microbiology*, 155(3): 667-679 (2008).

Anti-IsdH monoclonal antibodies (mAB) were identified using VelocImmune Mice® (Regeneron Pharmaceuticals) and phage panning (Dyax or CAT libraries). 59 IgG antibodies were purified (29 from the Dyax libraries, 16 from the CAT libraries, and 14 from the VelocImmune mice).

Example 4—Anti-IsdH mAB Screening Cascade

Identified anti-IsdH mABs were evaluated by ELISA for whole cell *S. aureus* binding in vitro. Antibodies were also screened by ELISA for inhibition of *S. aureus* haptoglobin binding. Antibodies were then evaluated in an opsonophagocytic killing assay (OPK) (described below). Eleven anti-IsdH IgG antibodies were identified that were opsonic for 4 *S. aureus* isolates. Five anti-IsdH antibodies effectively bound *S. aureus* following in vivo passage in a mouse infection model (described below). These top five anti-IsdH mABs (3 from the Dyax libraries and 2 from the CAT libraries) were selected for scale-up of antibody production, affinity testing, and subsequent in vivo testing. In vivo testing included studies in a bacteremia model (described below). Antibody 2F4 significantly reduced CFUs in the bacteremia model. The five antibodies were then characterized and evaluated for use in combination therapy.

The opsonophagocytic killing (OPK) assay involved combining 10 μl of *S. aureus* ($10^6$ cells/ml), 10 μl of monoclonal antibody, and 60 μl of DMEM plus 0.1% gelatin. The solution was incubated for 30 minutes at 4° C. After 30 minutes, 10 μl of human promyelocytic leukemia (HL-60) cells at $10^7$ cells/ml were added, along with 10 μl of human sera pre-absorbed against *S. aureus*. At time $T_0$, 10 μl of solution was plated and then incubated at 37° C. with 1500 rpm of shaking for 60 minutes. At time $T_{60}$) the HL-60 cells were lysed with 1% saponin, replated, and CFU concentration determined. The percentage OPK was calculated as calculated as follows: $100\times(1-(T_{60}/T_0))$, where $T_{60}$ refers to the CFU concentration at the end of the assay (i.e., at 60 minutes) and $T_0$ refers to the CFU concentration at the beginning of the assay.

11 monoclonal anti-IsdH antibodies were identified that were sufficiently opsonic against 4 *S. aureus* isolates to merit further investigation. FIG. 1 illustrates that antibodies B11, 2F4, and A7 had an increased percentage OPK, as compared to control antibody R347, when tested in *S. aureus* strains Newman and USA300.

To determine whether the antigens targeted by the antibodies were expressed by *S. aureus* in vivo, antibody binding was assessed following in vivo passage in mouse. Mice were challenged intraperitoneally with approximately $5\times10^8$ CFU of *S. aureus*. After 1 to 6 hours, mice were ex-sanguinated and blood was pooled into ice cold citrate. Eukaryotic cells were lysed with 1% NP-40. Lysed cells were washed three times with phosphate buffered saline (PBS) and sonicated, followed by resuspension of *S. aureus* bacteria in buffer (approximately $0.5\text{-}10\times10^6$ CFU were recovered after lysis and resuspension). Anti-IsdH antibodies were administered to cell lysates, and antibody binding was evaluated by staining and FACs sorting.

Figure 2:
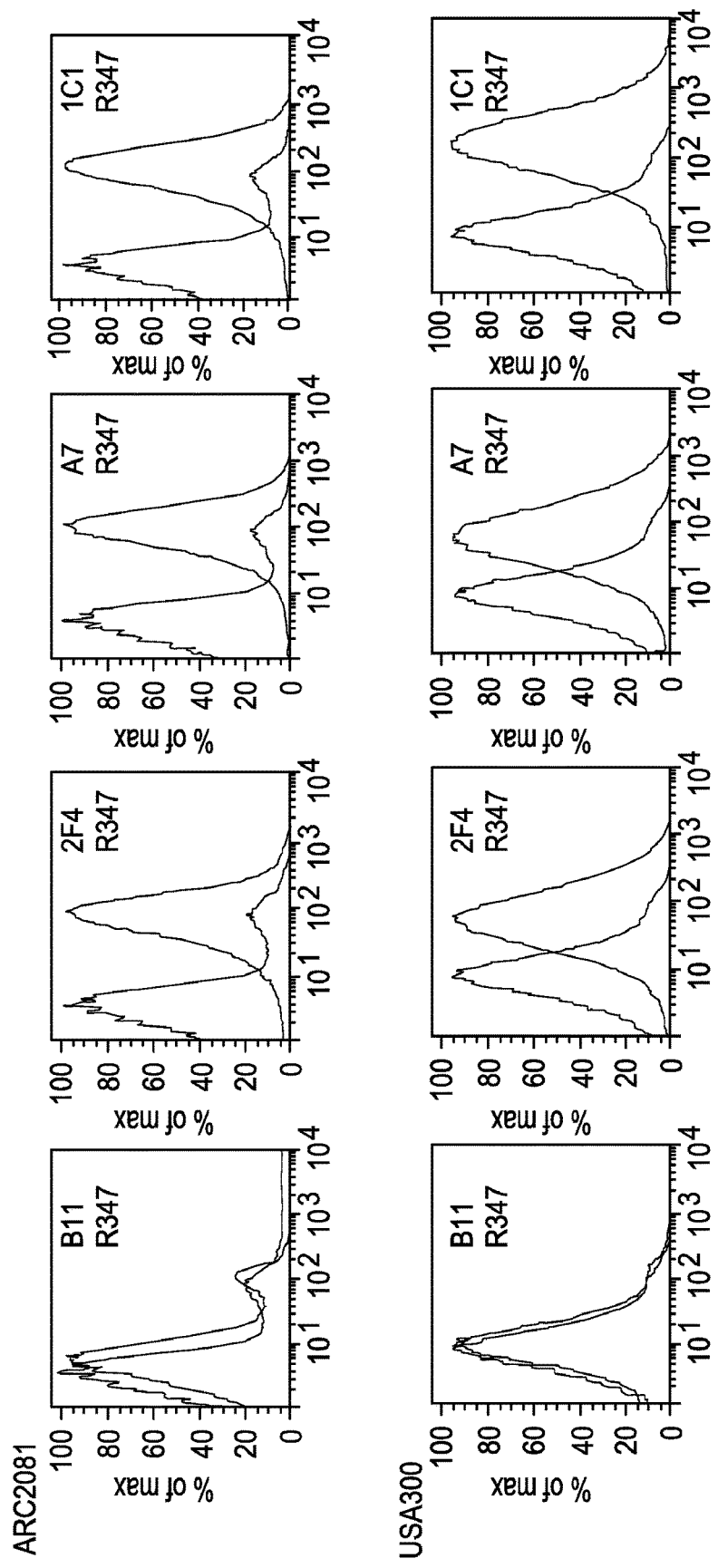
FIG. 2 shows binding of anti-IsdH antibodies B11, 2F4, A7, and 1C1, as compared to control antibody R347, with *S. aureus* strains ARC2081 and USA300.

Five of the eleven anti-IsdH mABs (designated 1C1, 2F4, A7, IsdH003, and IsdH0016) bound *S. aureus* following in vivo passage. FIG. 2 illustrates binding of antibodies B11, 2F4, A7, and 1C1, as compared to control antibody R347, in *S. aureus* strains ARC2081 and USA300. The figure shows that antibodies 2F4, A7, and 1C1 bind *S. aureus* ex vivo.

Figure 3A:
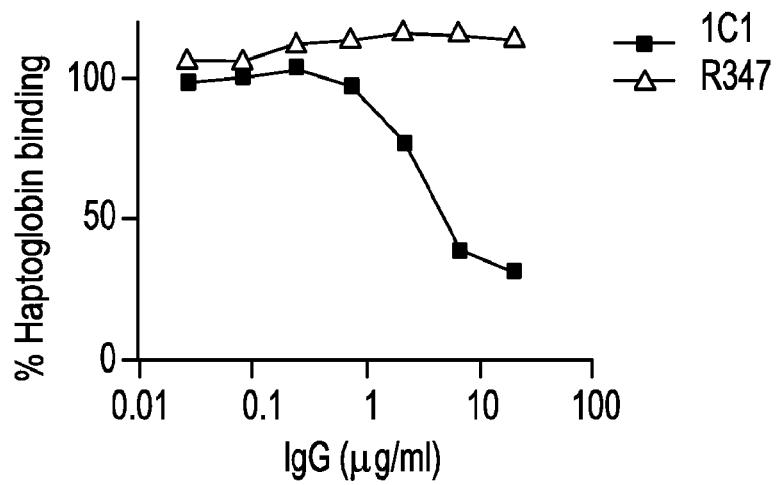
FIG. 3A is a plot of competitive binding between antibody 1C1 and haptoglobin (Hp) for binding to subunit Neat-1 on IsdH, as compared to competitive binding between control antibody R347 and Hp.
Figure 3B:
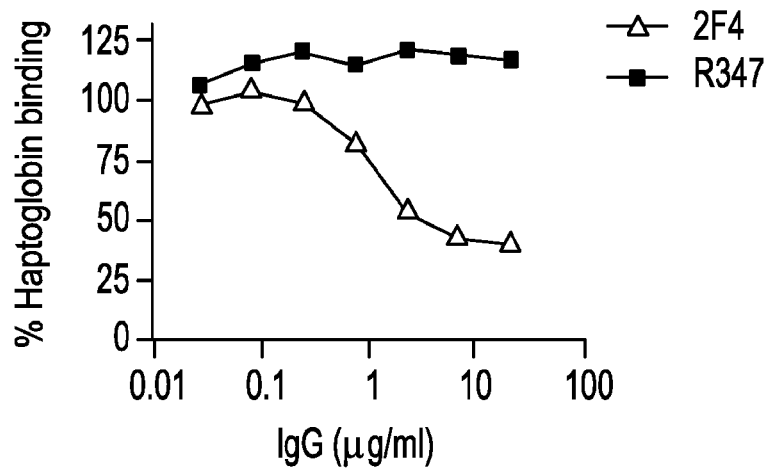
FIG. 3B is a plot of competitive binding between antibody 2F4 and Hp for binding to subunit Neat-2 on IsdH, as compared to competitive binding between control antibody R347 and Hp.
Figure 4B:
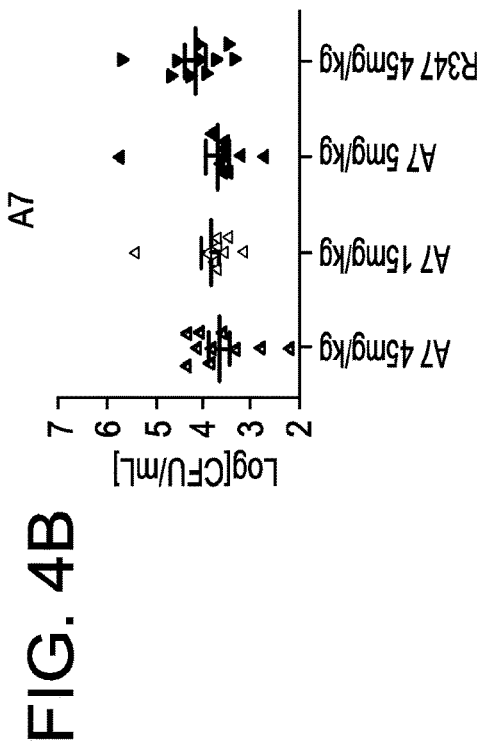
FIG. 4B shows the concentration of *S. aureus* CFU measured in a mouse bacteremia model in the presence of antibody A7. CFU concentration is reported as $\log_{10}[\text{CFU/ml}]$.
Figure 4D:
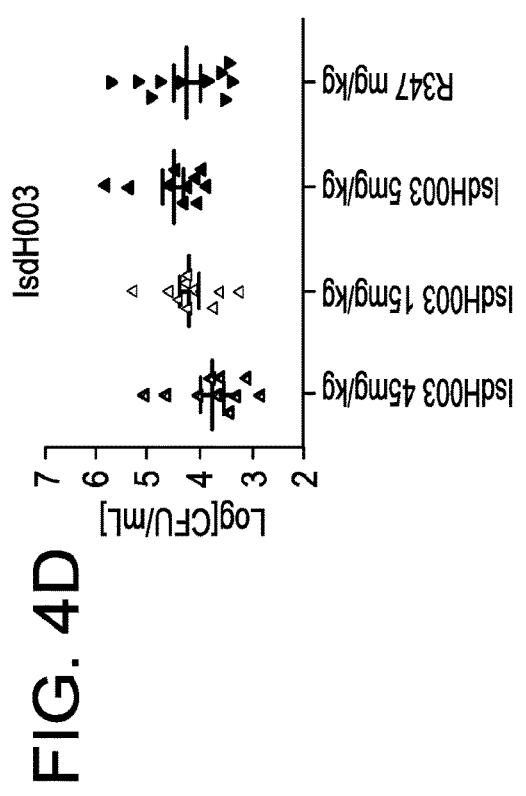
FIG. 4D shows the concentration of *S. aureus* CFU measured in a mouse bacteremia model in the presence of antibody IsdH003. CFU concentration is reported as log [CFU/ml].
Figure 4A:
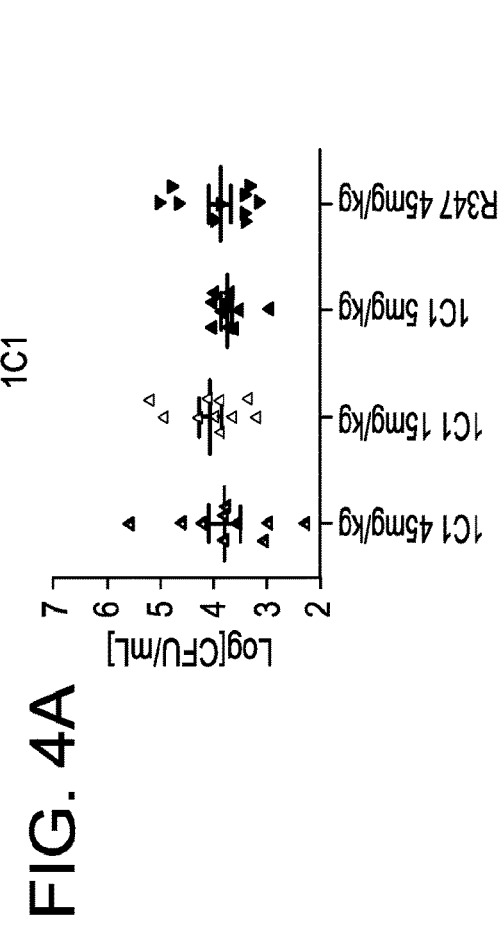
FIG. 4A shows the concentration of *S. aureus* colony forming units (CFU) measured in a mouse bacteremia model in the presence of antibody 1C1. CFU concentration is reported as $\log_{10}[\text{CFU/ml}]$.
Figure 4C:
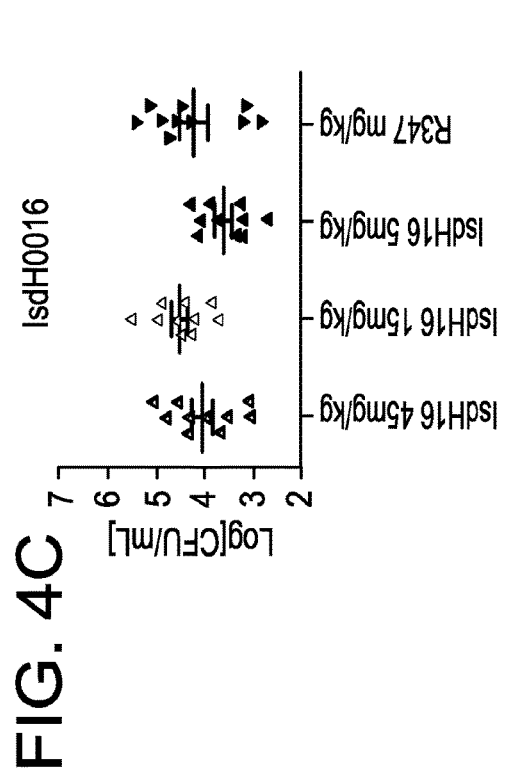
FIG. 4C shows the concentration of *S. aureus* CFU measured in a mouse bacteremia model in the presence of antibody IsdH0016. CFU concentration is reported as $\log_{10}[\text{CFU/ml}]$.

Two of the five anti-IsdH mABs (1C1 and 2F4) also competed with haptoglobin (Hp) for binding to IsdH, while the other three did not. FIG. 3 shows that antibody 1C1 competes with Hp for binding to subunit Neat-1 on IsdH. Increasing concentrations of 1C1 (in μg/ml) correlate with a reduction in Hp binding to IsdH, as compared to Hp binding in the presence of control antibody R347. Likewise, FIG. 3 shows that antibody 2F4 competes with Hp for binding to subunit Neat-2 on IsdH. Increasing concentrations of 2F4 (in μg/ml) correlate with a reduction in Hp binding to IsdH, as compared to Hp binding in the presence of control antibody R347.

Figure 5B:
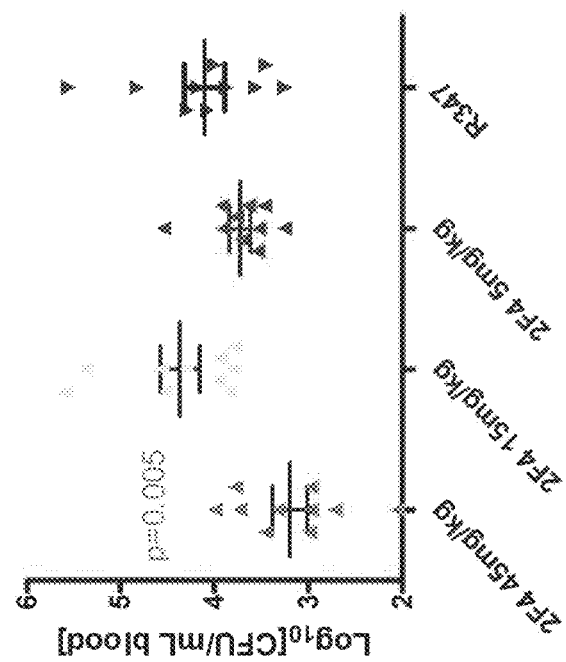
FIG. 5A and FIG. 5B show results from two exemplary assessments of antibody efficacy utilizing a mouse bacteremia model.
Figure 5A:
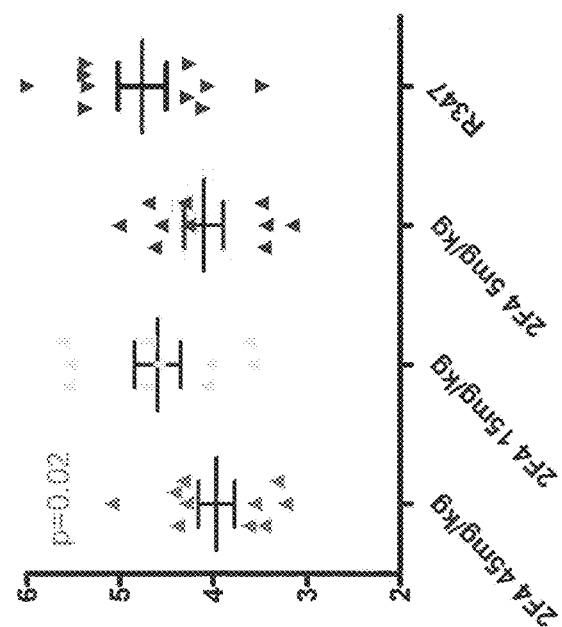
Figure 7A:
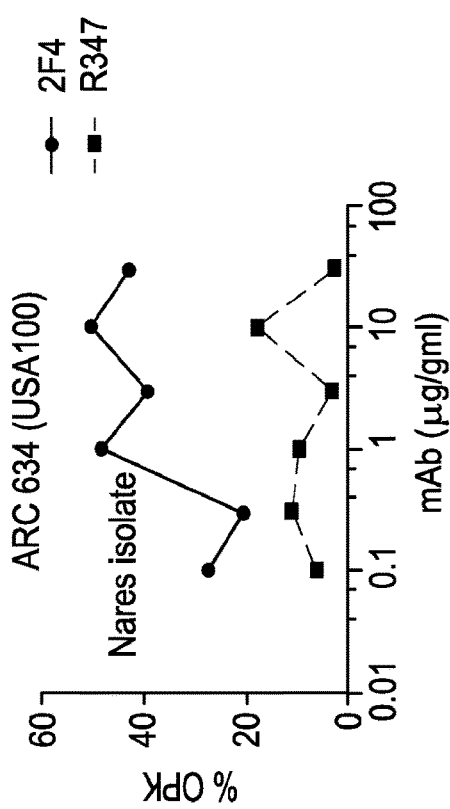
FIG. 7A shows the percentage OPK induced by antibody 2F4, as compared to percent OPK induced by control antibody R347, when tested with *S. aureus* strain Newman.
Figure 7B:
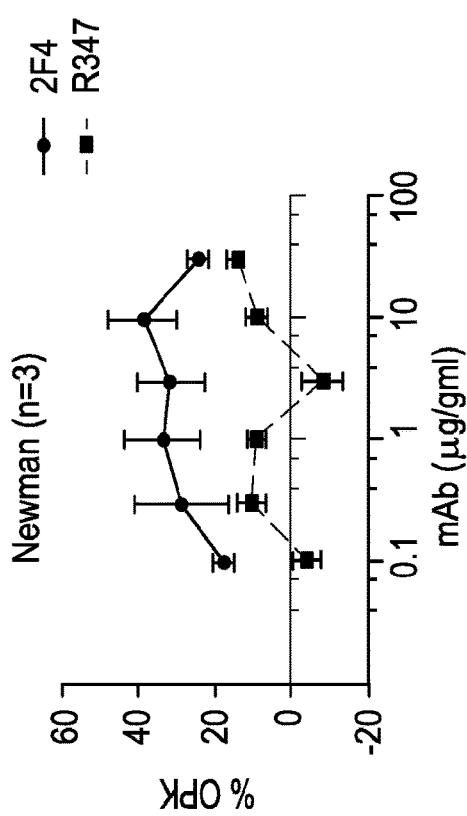
FIG. 7B shows the percentage OPK induced by antibody 2F4, as compared to percent OPK induced by control antibody R347, when tested with *S. aureus* strain ARC634.
Figure 7C:
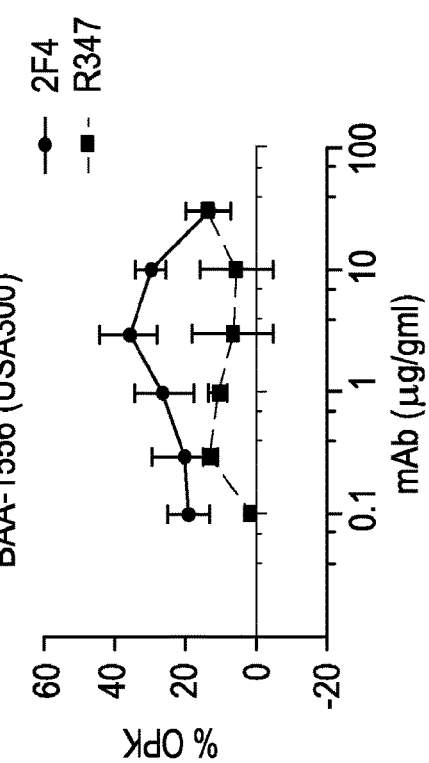
FIG. 7C shows the percentage OPK induced by antibody 2F4, as compared to percent OPK induced by control antibody R347, when tested with *S. aureus* strain ARC2081 (USA200).
Figure 7D:
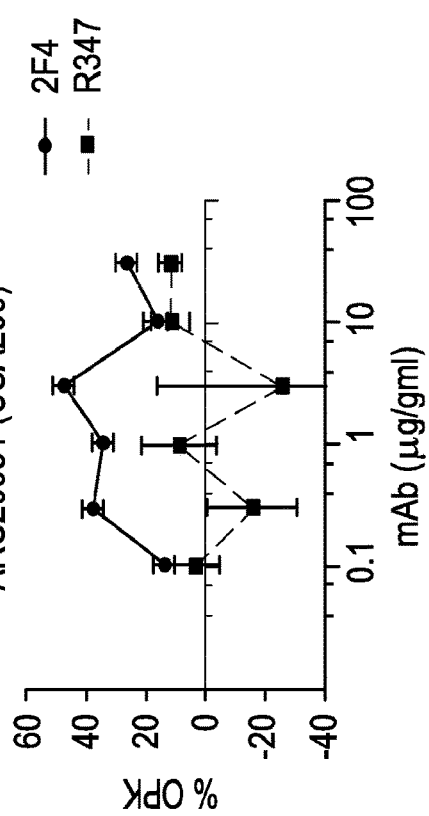
FIG. 7D shows the percentage OPK induced by antibody 2F4, as compared to percent OPK induced by control antibody R347, when tested with *S. aureus* strain BAA-1556 (USA300).

To assess whether antibodies 1C1, 2F4, A7, IsdH003, and IsdH0016 were effective when administered in vivo, a mouse bacteremia model was employed. Mice were injected intra-peritoneally with a monoclonal antibody at 45, 15 or 5 mg/kg, then allowed to recover overnight. The following day, mice were infected intraperitoneally with approximately $10^8$ CFU of *S. aureus* (Newman strain). Approximately 4 hours later, blood was collected and evaluated for CFU concentration, measured as log [CFU/ml]. FIG. 4 shows that antibodies 1C1, A7, IsdH003, and IsdH0016 did not reduce the CFU concentration in the bacteremia model. However, FIG. 5 shows that antibody 2F4 does reduce the CFU concentration in the murine bacteremia model.

Antibody 2F4 was further evaluated for ex vivo binding to various strains of *S. aureus*. The antibody bound to 23 of 25 isolates of *S. aureus* following in vivo passage and extraction in mouse. FIG. 6 illustrates 2F4 binding in strains ARC2379 (USA100), ARC2081 (USA200) and BAA-1556 (USA 300). The table below illustrates the results of binding experiments following in vivo passage of 25 *S. aureus* strains in mouse.

Binding of Antibody 2F4 Following In Vivo Passage of *S. aureus* Strains

|  | NRS 22 USA 600 | NRS 123 USA 400 | NRS 383 USA 200 | NRS 384 USA 300 | NRS 484 USA 1100 | ARC 797 USA 500 | ARC 1206 USA 700 | ARC2558 USA 400 |
|---|---|---|---|---|---|---|---|---|
| $T_0$ | neg. | neg. | neg. | neg. | neg. | +/− | +/− | +/− |
| 1 hr | + | + | + | + | + | +/− | + | + |
| 4 hr | + | + | + | + | + | +/− | + | + |

|  | UAMS-1 USA 200 | NEWMAN | BAA1556 USA 300 | NRS 261 MSSA | NRS 382 USA 100 | ARC2379 USA 100 | ARC 517 USA 600 | NRS385 USA500 |
|---|---|---|---|---|---|---|---|---|
| $T_0$ | neg. | neg. | neg. | neg. | +/− | +/− | neg. | +/− |
| 1 hr | neg. | + | + | + | + | + | + | neg. |
| 4 hr | neg. | + | + | + | neg. | + | + | + |

|  | NR5655 USA300 | 1056 USA300 | ARC2464 USA300 | ARC 516 USA 800 | NRS 234 MSSA | NRS 249 MRSA | ARC633 MSSA | ARC634 MRSA | ARC635 MRSA |
|---|---|---|---|---|---|---|---|---|---|
| $T_0$ | +/− | +/− | neg. | + | neg. | neg. | neg. | + | neg. |
| 1 hr | + | +/− | + | + | +/− | + | + | + | + |
| 4 hr | + | + | + | + | + | + | N/A | + | N/A |

Antibody 2F4 was also evaluated in OPK assays involving the *S. aureus* clinical isolates—Newman, ARC634 (USA100), ARC2081 (USA200), and BAA-1556 (USA300). FIG. 7 shows that 2F4 was opsonic for the major *S. aureus* clinical isolates.

Figure 8:
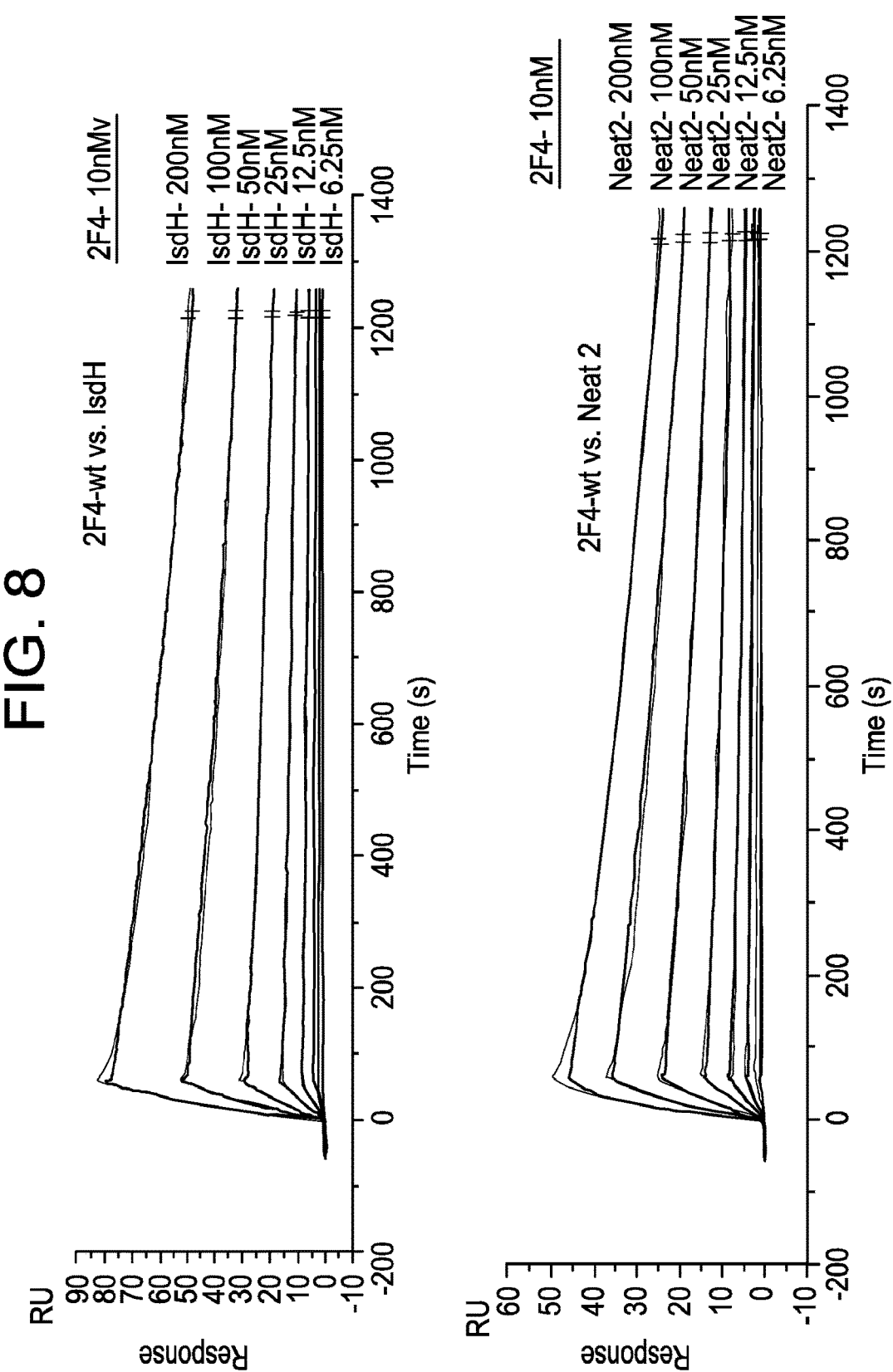
FIG. 8 shows evaluation of 2F4 for affinity to IsdH and to the Neat-2 subunit in a huIgGFc capture assay.

2F4 was subsequently evaluated for affinity to IsdH and to the Neat-2 subunit in a hu_IgGFc capture assay. The mean affinity, averaged across three experiments, revealed a $K_D$ for IsdH of 3.66 nM and a $K_D$ for Neat-2 of 2.57 nM. FIG. 8.

Example 5—Anti-IsdH & Anti-AT Antibody Combination Therapy

Alpha toxin and IsdH play different roles during pathogenesis following *S. aureus* infection. The former is a secreted toxin, while the latter is a surface protein important for colonization, immune evasion, and bacterial fitness. The two may be differentially expressed by *S. aureus* during infection. Combining monoclonal antibodies with different methods of action could potentially produce additive or synergistic effects, while reducing the risk that a strain will evade therapy.

Figure 9A:
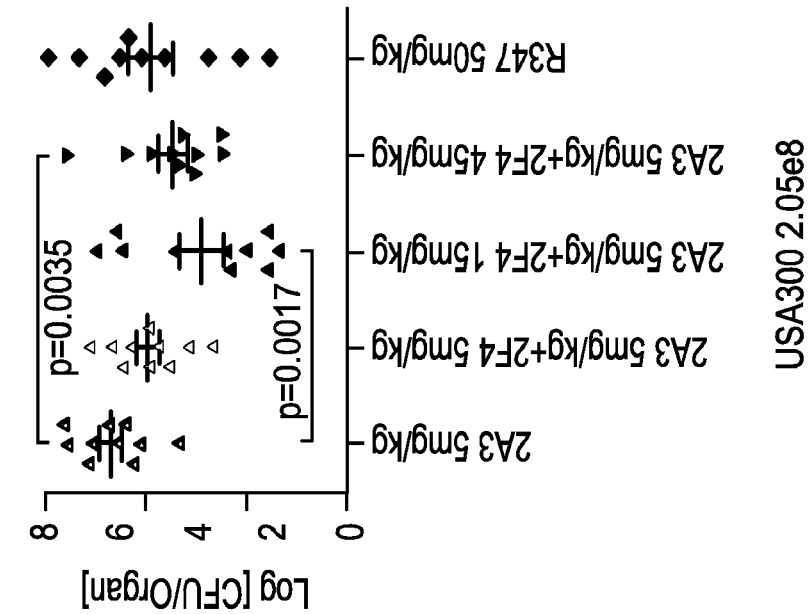
FIG. 9A shows the kidney CFU concentration of *S. aureus* strain USA300 (administered at an initial concentration of 2.05e8) measured in an organ burden model after treatment with 2F4 alone, 2A3 alone, or a combination of 2F4 and 2A3. CFU concentration is reported as $\log_{10}[\text{CFU/organ}]$.
Figure 9B:
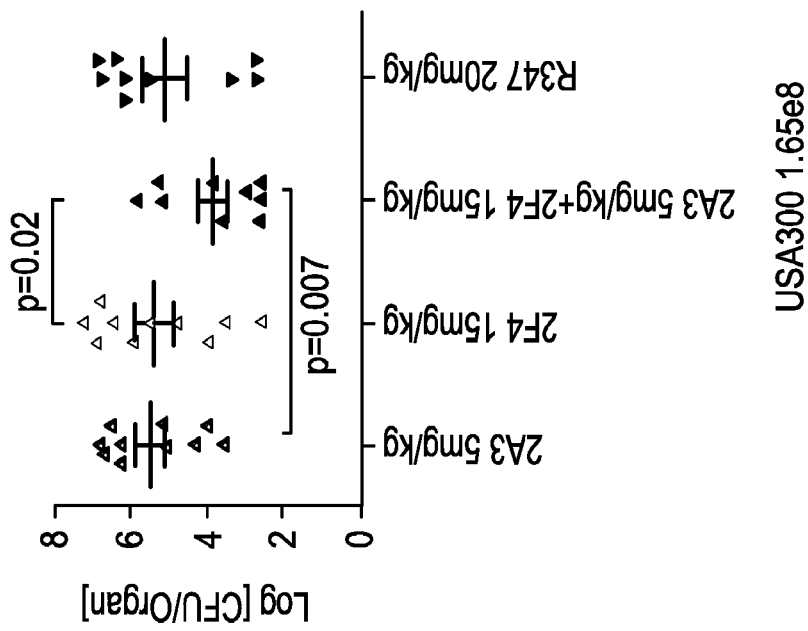
FIG. 9B shows the kidney CFU concentration of *S. aureus* strain USA300 (administered at an initial concentration of 2.05e8) measured in an organ burden model after treatment with 2F4 alone, 2A3 alone, or a combination of 2F4 and 2A3. CFU concentration is reported as $\log_{10}[\text{CFU/organ}]$.

2A3, an anti-alpha toxin antibody was evaluated for use in combination with 2F4, an anti-IsdH antibody. When administered in combination, antibodies 2A3 and 2F4 exhibited synergistic effects in the organ burden model. FIG. 9 shows that the kidney distribution of *S. aureus* strain USA300 was reduced in the presence of both antibodies, as compared to either antibody alone or to control antibody R347.

The results of these combination therapy experiments suggest that a combination approach to prophylaxis or treatment of *S. aureus* may be effective.

Example 6—Anti-ClfA mAbs Inhibit ClfA Binding

Anti-ClfA mAbs inhibit ClfA binding to immobilized fibrinogen in vitro. ClfA as a virulence factor has been reported to promote *S. aureus* binding to fibrinogen present in plasma. This results in bacteria agglutination in blood.

The ability of three anti-ClfA mAbs generated through B cell hybridoma technology to inhibit ClfA binding to immobilized fibrinogen was evaluated. The antibody R347 was used as a negative control. Each anti-ClfA mAb activity in this assay was calculated at an IC50, the concentration required to promote 50% binding inhibition. As shown in FIG. 10, together with the IC50 of each antibody, the anti-ClfA antibodies inhibit ClfA binding to immobilized fibrinogen.

Figure 11:
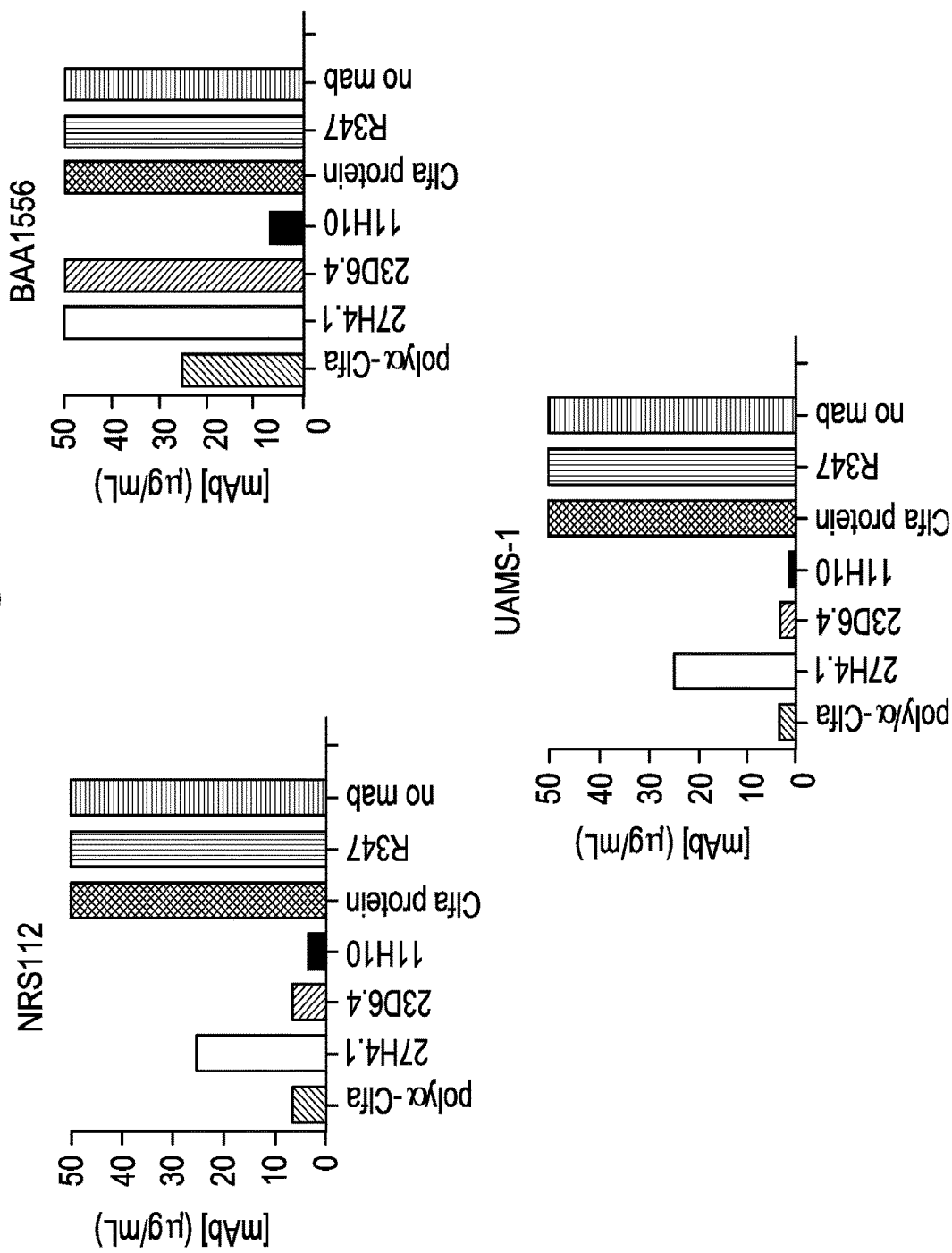
FIG. 11 shows that anti-ClfA antibodies inhibit *S. aureus* agglutination in human plasma. The ability of anti-ClfA antibodies 23D6, 27H4, 11H10 to inhibit agglutination of three different strains of *S. aureus* (NR S112, BAA 1556 and UAMS-1) as compared to control R347, no mAb and ClfA protein was tested. The anti-ClfA antibody 11H10 exhibited the largest strain coverage in this assay.
Figure 12:
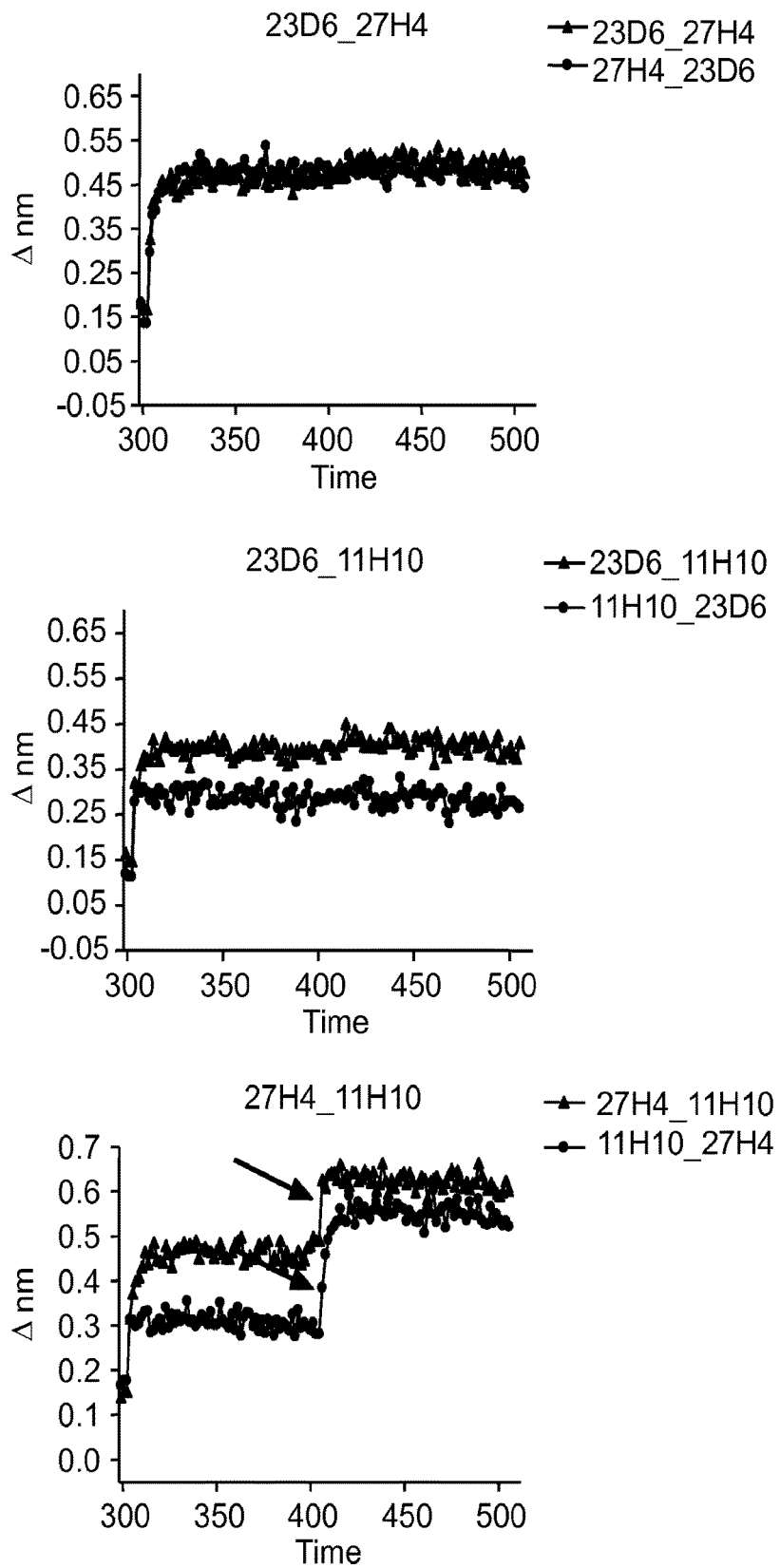
FIG. 12 shows that the anti-ClfA antibody 11H10 binds to a different epitope on ClfA as compared to the anti-ClfA antibodies 23D6 and 27H4.

Example 7—Anti-ClfA mAb11H10 Inhibits *S. Aureus* Agglutination in Human Plasma with Three Different Clinical Isolates To assess *S. aureus* agglutination in human plasma, bacteria was incubated with each anti-ClfA mAb, and bacteria clumping was examined visually after 3 min incubation at 37° C. For a more accurate comparison, mAb activities in this assay were compared at the minimum concentration required to inhibit agglutination. 11H10 was more efficient than 27H4 or 23D6 (FIG. 11). In addition, agglutination experiments were conducted with three different clinical isolates, and 11H10 exhibited inhibition against these three isolates as compared to the two other anti-ClfA mAbs covering one or two strains.

Example 8—Epitope Binding for 11H10

Given the differing characteristics of 11H10 as compared to 23D6 and 27H4 as discussed above, its binding characteristics were further explored. Epitope competition binding was run by Octet to assess if 11H10 bind a different epitope than 23D6 and 27H4. As seen in FIG. 12, 23D6 and 27H4 competed for binding to ClfA suggesting they may share a common region on ClfA for binding. However, there was no competition between 11H10 and 23D6 or 11H10 and 27H4 demonstrating that 11H10 epitope on ClfA is different than for 23D6 and 27H4.

Figure 13:
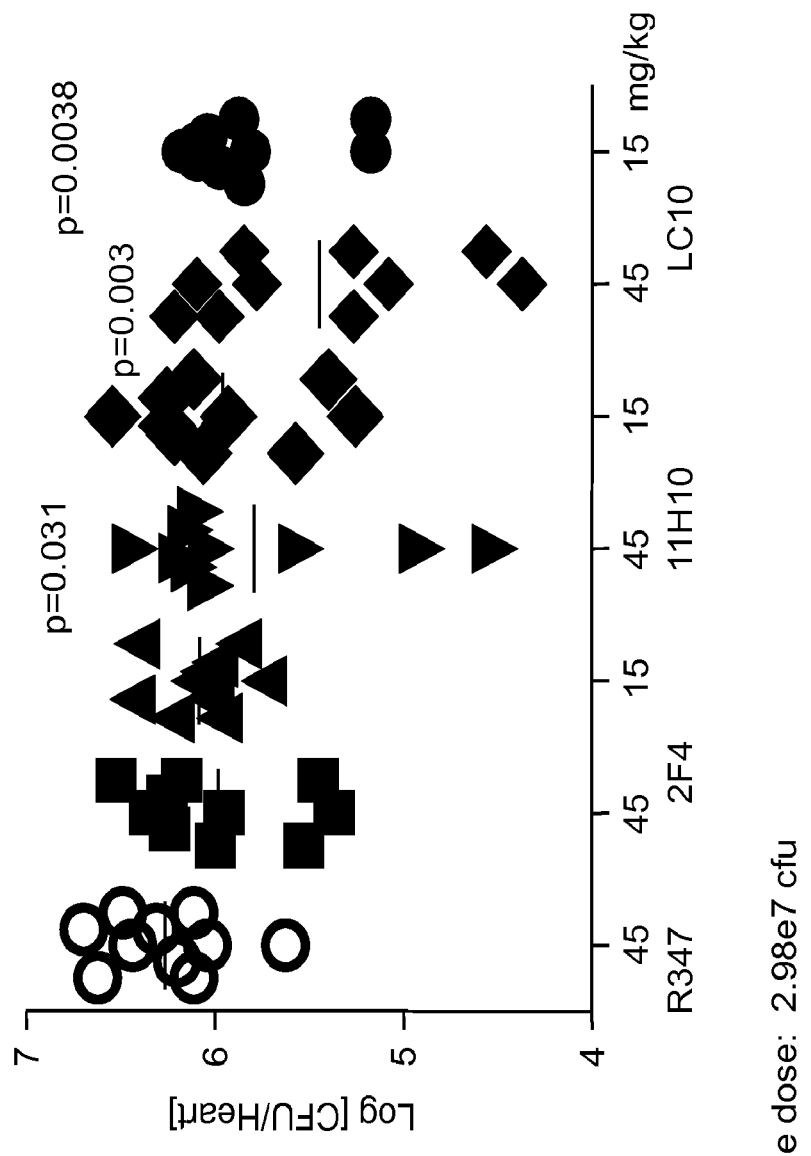
FIG. 13 demonstrates that the anti-ClfA antibody 11H10 and anti-AT antibody LC10 reduce bacteria load in the heart.

Example 9—Passive Immunization with Anti-ClfA mAb 11H10 Demonstrates Efficacy in a Lethal IV Challenge Model Bacteria Load in Heart To test whether staphylococcal agglutination occurred in vivo, mice were first challenged in tail vein with a USA300 isolate, and bacteria number were enumerated in the heart after 14 h infection. As shown in FIG. 13, prophylactic administration of the anti-ClfA mAb 11H10 intra-peritoneally (IP) at 45 mg/kg resulted in significant decrease of bacteria cfu in heart (p=0.031). This was dose dependent since 11H10 at 15 mg/kg only slightly reduced the bacteria load in the heart as compared to the negative control R347.

Survival

Figure 14:
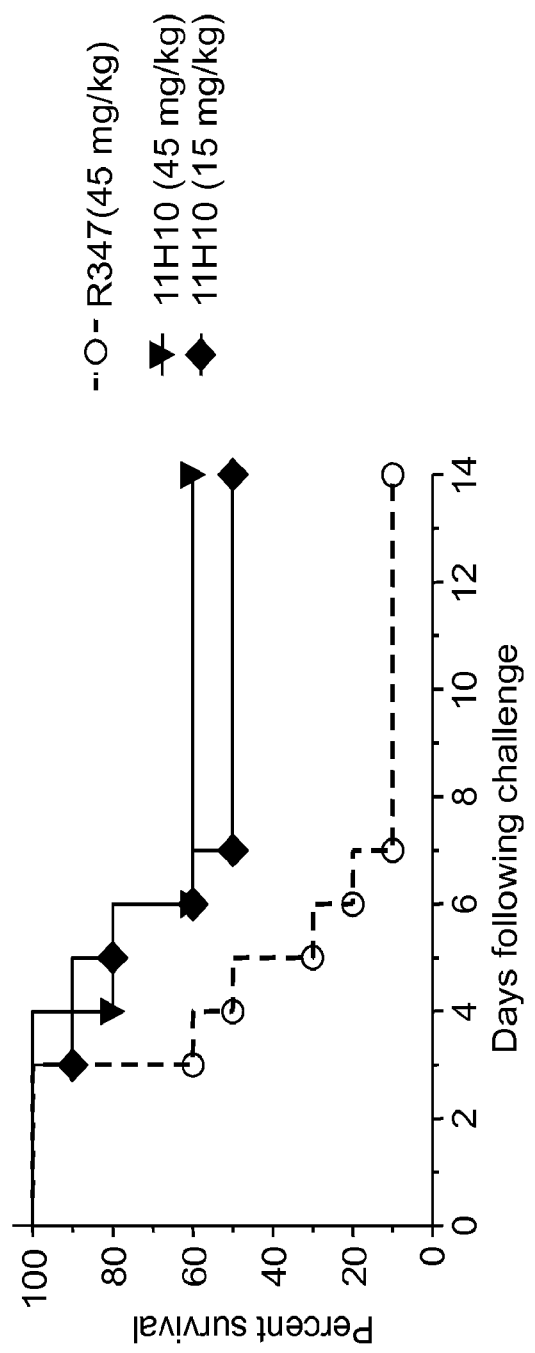
FIG. 14 shows the effect of the anti-ClfA antibody 11H10 in a murine sepsis model.

The USA300 challenge dose for IV challenge was determined to induce 20% survival after 2 weeks. The capacity of anti-ClfA mAb 11H10 to increase animal survival was investigated in this model. FIG. 14 shows that 11H10 injection resulted in significant increase of survival (p=0.0114 at 45 mg/kg, and p=0.0239 at 15 mg/kg) over 2 weeks post infection.

Example 10—Efficacy of Anti-ClfA mAB 11H10 and Anti-AT Ab LC10 Combination in a Lethal IV Challenge Model Six week old BALB/c mice female were passively immunized intraperitoneally (IP) with mAbs at indicated concentrations (diluted in 500 µl PBS), and intravenously (IV) challenged with an LD20 dose of bacteria in the tail vein (in 200 ul PBS) 24 h later. Survival was monitored until 14 days post infection.

Data were analyzed with a Log Rank (mantel-cox) test, and p value considered statistically significant if ≤0.05. To test whether staphylococcal agglutination occurred in vivo, mice were first challenged in the tail vein with a CA-MRSA USA300, HA-MRSA-100 or HA-MSSA USA200 isolate, and bacteria number were enumerated in the heart and kidney after 14 h infection.

Figure 15:
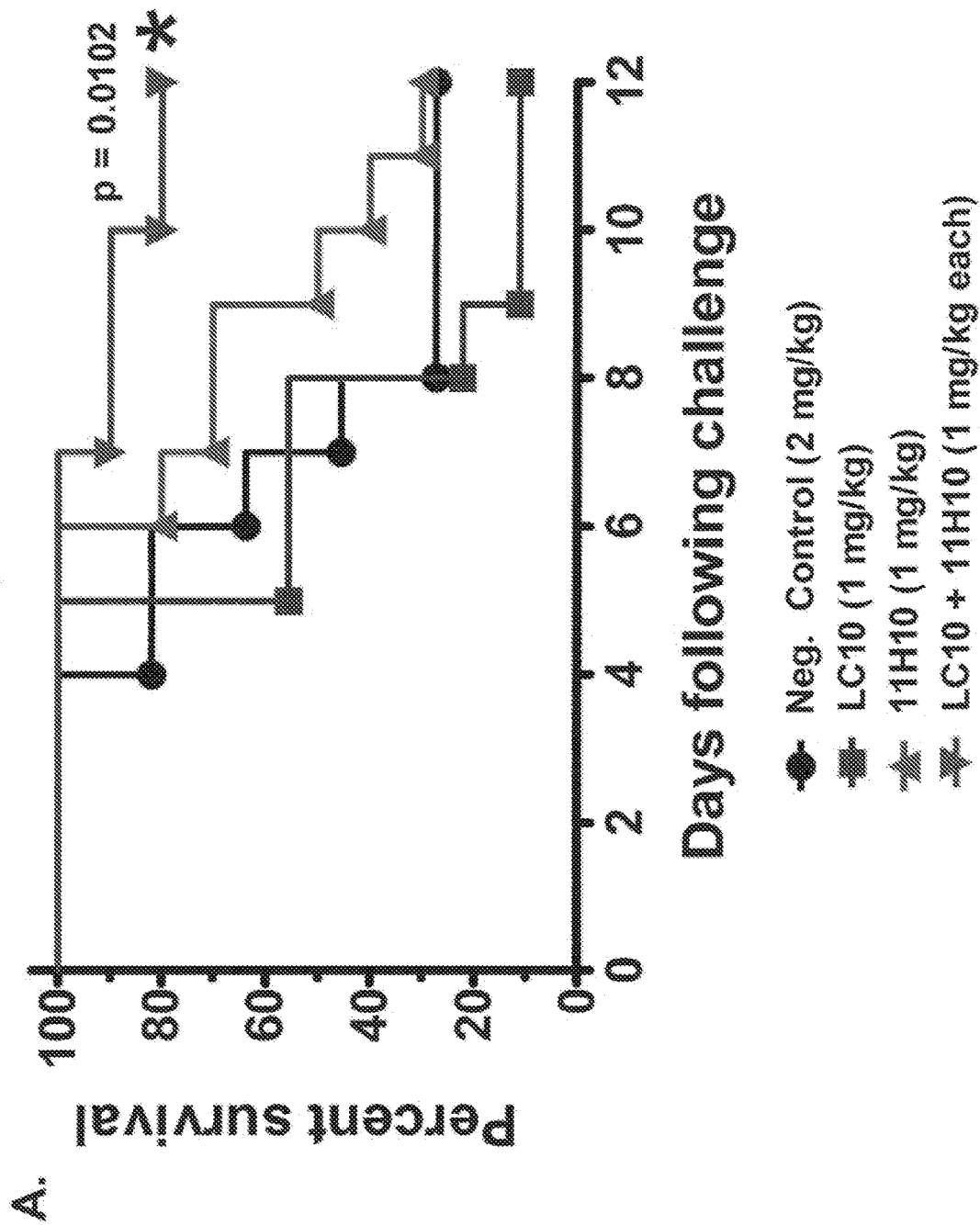
FIG. 15 shows the effect of the anti-ClfA antibody 11H10, the anti-AT antibody LC10 and the combination of anti-ClfA antibody 11H10 with the anti-AT antibody LC10 in a murine sepsis model (IV lethal challenge) with CA-MRSA USA300 challenge.

The efficacy of the combination of anti-ClfA mAB 11H10 and anti-AT Ab LC10 combination in a lethal IV challenge model was tested. As shown in FIG. 15, prophylactic administration of the anti-ClfA mAb 11H10, the anti-AT LC10 mAb, and the combination of both anti-ClfA mAb and anti-AT LC10 mAb resulted in a significant decrease of bacteria cfu in the heart (FIG. 15*b*) and the kidney (15*c*).

FIG. 15 also demonstrates the capacity of anti-ClfA mAb 11H10, anti-AT mAb LC10 and the combination of anti-ClfA mAb 11H10 and anti-At mAb LC10 to increase animal survival as investigated in the IV challenge model using a USA300 challenge dose. FIG. 15*a* shows that the combination of both resulted in significant increase in response with respect to survival over 2 weeks post infection as compared to control and as compared to either anti-ClfA mAb and anti-AT mAb alone.

Figure 17:
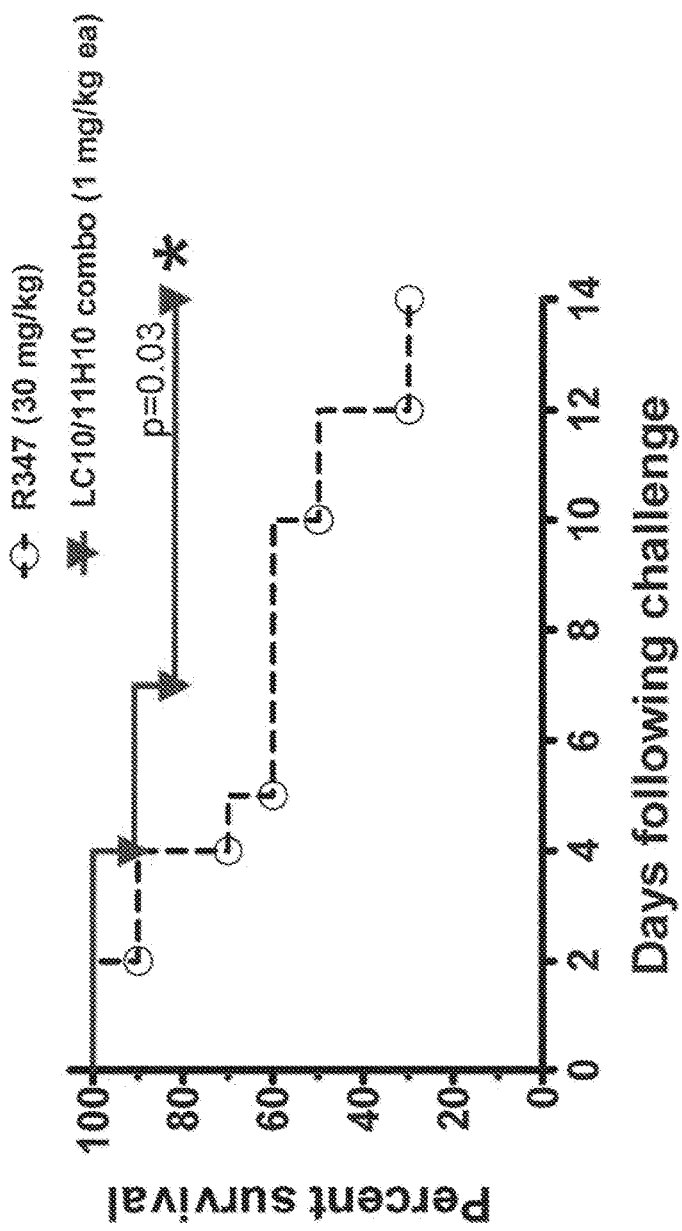
FIG. 17 shows the effect of the combination of anti-ClfA antibody 11H10 with the anti-AT antibody LC10 in a murine sepsis model (IV lethal challenge) with HA-MRSA USA200 challenge.

FIGS. 16 and 17 further demonstrate the capacity of the combination of anti-ClfA mAb 11H10 and anti-At mAb LC10 to increase animal survival as investigated in the IV challenge model using an HA-MRSA USA100 challenge dose (FIG. 16) and an HA-MSSA USA200 challenge dose (FIG. 17).

Example 11—Efficacy of Anti-IsdH mAb 2F4 and Anti-AT Ab LC10 Combination in a Lethal IV Challenge Model Experiments were performed as described above in Example 10.

Figure 18:
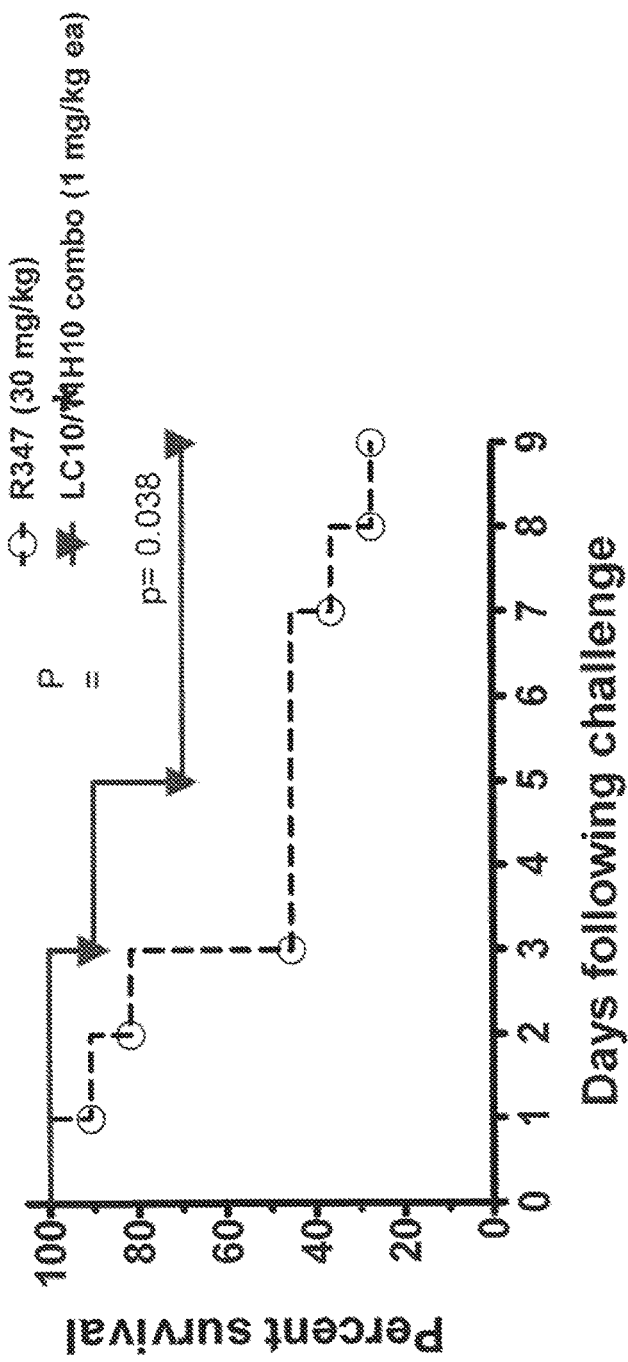
FIG. 18 shows the effect of the combination of anti-C1fA antibody 11H10 with the anti-AT antibody LC10 in a murine sepsis model (IV lethal challenge) with HA-MSSA USA200 challenge.

The efficacy of the combination of anti-IsdH mAb 2F4 and anti-AT Ab LC10 combination in a lethal IV challenge model was tested. As shown in FIG. 18, the combination of anti-IsdH mAb 2F4 and anti-At mAb LC10 increased animal survival as investigated in the IV challenge model using a HA-MRSA USA100 challenge dose. FIG. 18 shows that the combination resulted in significant increase in response with respect to survival over 6 days post infection as compared to the R347 control.

Tables of Sequences

TABLE 1

VL CDR sequences for mAbs 2A3.1, 10A7.5, 12B8.19 and 25E9.1

| SEQ ID NO: | Description | Sequence |
|---|---|---|
| SEQ ID NO: 1 | VL CDR1 | RASQSISSWLA |
| SEQ ID NO: 2 | VL CDR2 | KASSLES |
| SEQ ID NO: 3 | VL CDR3 | QQYNSYWT |

TABLE 2

VL CDR sequences for mAB 28F6.1

| SEQ ID NO: | Description | Sequence |
|---|---|---|
| SEQ ID NO: 4 | mAb 28F6.1 VL CDR1 | RASQGIRNDLG |
| SEQ ID NO: 5 | mAb 28F6.1 VL CDR2 | DASSLQS |
| SEQ ID NO: 6 | mAb 28F6.1 VL CDR3 | LQDYNYPWT |

TABLE 3

VH CDR sequences for mAb 2A3.1

| SEQ ID NO: | Description | Sequence |
|---|---|---|
| SEQ ID NO: 7 | VH CDR1 | SYDMH |
| SEQ ID NO: 8 | VH CDR2 | GIGTAGDTYYPGSVKG |
| SEQ ID NO: 9 | VH CDR3 | DNYSSTGGYYGMDV |

TABLE 4

VH CDR sequences for mAbs 10A7.5 and 12B8.19

| SEQ ID NO: | Description | Sequence |
|---|---|---|
| SEQ ID NO: 10 | VH CDR1 | RYDMH |
| SEQ ID NO: 11 | VH CDR2 | VIGTDGDTYYPGSVKG |
| SEQ ID NO: 12 | VH CDR3 | DRYSSSNHYNGMDV |

TABLE 5

VH CDR sequences for mAb 28F6.1

| SEQ ID NO: | Description | Sequence |
|---|---|---|
| SEQ ID NO: 13 | mAb 28F6.1 VH CDR1 | SYAMT |
| SEQ ID NO: 14 | mAb 28F6.1 VH CDR2 | VISGSGGSTYYADSVKG |
| SEQ ID NO: 15 | mAb 28F6.1 VH CDR3 | DGRQVEDYYYYGMDV |

TABLE 6

VH CDR sequences for mAb 25E9.1

| SEQ ID NO: | Description | Sequence |
|---|---|---|
| SEQ ID NO: 7 | mAb 25E9.1 VH CDR1 | SYDMH |
| SEQ ID NO: 17 | mAb 25E9.1 VH CDR2 | VIDTAGDTYYPGSVKG |
| SEQ ID NO: 18 | mAb 25E9.1 VH CDR3 | DRYSGNFHYNGMDV |

TABLE 7

VL and VH amino acid sequences for anti-alpha toxin mAbs

| Description | VH or VL sequence (with CDRs in bold) | CDR1 | CDR2 | CDR3 |
|---|---|---|---|---|
| mAb 2A3.1 VL | DIQMTQSPSTLSASVGDRVTIT CRASQSISSWLAWYQQKPGK APKLLIYKASSLESGVPSRFSG SGSGTEFTLTISSLQPDDFATY YCQQYNSYWTFGQGTKVEIK (SEQ ID NO: 19) | RASQSISS WLA (SEQ ID NO: 1) | KASSLES (SEQ ID NO: 2) | QQYNSYW T (SEQ ID NO: 3) |
| mAb 2A3.1 VH | EVQLVESGGGLVQPGGSLRLS CAASGFTFSSYDMHWVRQAT GKGLEWVSGIGTAGDTYYPGS | SYDMH (SEQ ID NO: 7) | GIGTAGDT YYPGSVKG (SEQ ID | DNYSSTG GYYGMDV (SEQ ID |

TABLE 7-continued

VL and VH amino acid sequences for anti-alpha toxin mAbs

| Description | VH or VL sequence (with CDRs in bold) | CDR1 | CDR2 | CDR3 |
|---|---|---|---|---|
| | VKGRFTISRENAKNSLYLQLNS LRAGDTAVYFCARDNYSSTGG YYGMDVWGQGTTVTVSS (SEQ ID NO: 20) | | NO: 8) | NO: 9) |
| mAb 10A7.5 VL | DIQMTQSPSTLSASVGDRVTIT CRASQSISSWLAWYQQKPGK APKLLIYKASSLESGVPSRFSG SGSGTEFTLTISSLQPDDFATY YCQQYNSYWTFGQGTKVEIK (SEQ ID NO: 21) | RASQSISS WLA (SEQ ID NO: 1) | KASSLES (SEQ ID NO: 2) | QQYNSYW T (SEQ ID NO: 3) |
| mAb 10A7.5 VH | EVQLVESGGGLVQPGGSLRLS CAASGFTFSRYDMHWVRQAT GKGLEWVSVIGTDGDTYYPGS VKGRFIISRENAKNSLYLEMNS LRAGDTAVYYCARDRYSSSNH YNGMDVWGQGTTVTVSS (SEQ ID NO: 22) | RYDMH (SEQ ID NO: 10) | VIGTDGDT YYPGSVKG (SEQ ID NO: 11) | DRYSSSNH YNGMDV (SEQ ID NO: 12) |
| mAb 12B8.19 VL | DIQMTQSPSTLSASVGDRVTIT CRASQSISSWLAWYQQKPGK APKVLIYKASSLESGVPSRFSG SGSGTEFTLTISSLQPDDFATY YCQQYNSYWTFGQGTKVEIK (SEQ ID NO: 23) | RASQSISS WLA (SEQ ID NO: 1) | KASSLES (SEQ ID NO: 2) | QQYNSYW T (SEQ ID NO: 3) |
| mAb 12B8.19 VH | EVQLVESGGGLVQPGGSLRLS CAASGFTFSRYDMHWVRQAT GKGLEWVSVIGTDGDTYYPGS VKGRFIISRENAKNSLYLEMNS LRAGDTAVYYCARDRYSSSNH YNGMDVWGQGTTVTVSS (SEQ ID NO: 24) | RYDMH (SEQ ID NO: 10) | VIGTDGDT YYPGSVKG (SEQ ID NO: 11) | DRYSSSNH YNGMDV (SEQ ID NO: 12) |
| mAb 28F6.1 VL | AIQMTQSPSSLSASVGDRVTIT CRASQGIRNDLGWYQQKPGK APKLLIYDASSLQSGVPSRFSG SGSGTDFTLTISSLQPEDFATY YCLQDYNYPWTFGQGTKVEIK (SEQ ID NO: 25) | RASQGIRN DLG (SEQ ID NO: 4) | DASSLQS (SEQ ID NO: 5) | LQDYNYP WT (SEQ ID NO: 6) |
| mAb 28F6.1 VH | EVQLLESGGGLVQPGGSLRLS CAASGFTFSSYAMTWVRQAP GKGLEWVSVISGSGGSTYYAD SVKGRFTVSRDNSKNTLYLQM NSLRAEDTAVYYCAKDGRQVE DYYYYYGMDVWGQGTTVTVS S (SEQ ID NO: 26) | SYAMT (SEQ ID NO: 13) | VISGSGGS TYYADSVK G (SEQ ID NO: 14) | DGRQVED YYYYYGM DV (SEQ ID NO: 15) |
| mAb 25E9.1 VL | DIQMTQSPSTLSASVGDRVTIT CRASQSISSWLAWYQQKPGK APKLLIYKASSLESGVPSRFSG SGSGTEFTLTISSLQPDDFATY YCQQYNSYWTFGQGTKVEIK (SEQ ID NO: 27) | RASQSISS WLA (SEQ ID NO: 1) | KASSLES (SEQ ID NO: 2) | QQYNSYW T (SEQ ID NO: 3) |
| mAb 25E9.1 VH | EVQLVESGGGLVQPGGSLRLS CTASGFTFSSYDMHWVRQAT GKGLEWVSVIDTAGDTYYPGS VKGRFTISRENAKNSLYLQMN SLRAGDTAVYYCVRDRYSGNF HYNGMDVWGQGTTVTVSS (SEQ ID NO: 28) | SYDMH (SEQ ID NO: 7) | SVIDTAGD TYYPGSVK G (SEQ ID NO: 17) | DRYSGNF HYNGMDV (SEQ ID NO: 18) |
| mAb QD20 VH | EVQLVESGGGLVQPGGSLRLS CAASGFTFSSYDMHWVRQAT GKGLEWVSGIGTAGDTYYPGS VKGRFTISRENAKNSLYLQMN SLRAGDTAVYYCARDRYSPTG HYMGMDVWGQGTTVTVSS (SEQ ID NO: 41) | SYDMH (SEQ ID NO: 7) | GIGTAGDT YYPGSVKG (SEQ ID NO: 8) | DRYSPTGH YMGMDV (SEQ ID NO: 16) |

TABLE 7-continued

VL and VH amino acid sequences for anti-alpha toxin mAbs

| Description | VH or VL sequence (with CDRs in bold) | CDR1 | CDR2 | CDR3 |
|---|---|---|---|---|
| mAb QD20 VL | DIQMTQSPSTLSASVGDRVTITCRASQSISSWLAWYQQKPGK APKLLIYKASSLESGVPSRFSG SGSGTEFTLTISSLQPDDFATY YCQQYDTYWTFGQGTKVEIK (SEQ ID NO: 42) | RASQSISS WLA (SEQ ID NO: 1) | KASSLES (SEQ ID NO: 2) | QQYDTYW T (SEQ ID NO: 64) |
| mAb QD33 VH | EVQLVESGGGLVQPGGSLRLS CAASGFTFSSYDMHWVRQAT GKGLEWVSGIGTAGDTYYPGS VKGRFTISRENAKNSLYLQMN SLRAGDTAVYYCARDRYSRTG HYMGMDVWGQGTTVTVSS (SEQ ID NO: 43) | SYDMH (SEQ ID NO: 7) | GIGTAGDT YYPGSVKG (SEQ ID NO: 8) | DRYSRTG HYMGMDV (SEQ ID NO: 65) |
| mAb QD33 VL | DIQMTQSPSTLSASVGDRVTITCRASQSISSWLAWYQQKPGK APKLLIYKASSLESGVPSRFSG SGSGTEFTLTISSLQPDDFATY YCQQYDTYWTFGQGTKVEIK (SEQ ID NO: 44) | RASQSISS WLA (SEQ ID NO: 1) | KASSLES (SEQ ID NO: 2) | QQYDTYW T (SEQ ID NO: 64) |
| mAb QD37 VH | EVQLVESGGGLVQPGGSLRLS CAASGFTFSSYDMHWVRQAT GKGLEWVSGIGTAGDTYYPGS VKGRFTISRENAKNSLYLQMN SLRAGDTAVYYCARDRYSRTG HYMGMSLWGQGTTVTVSS (SEQ ID NO: 45) | SYDMH (SEQ ID NO: 7) | GIGTAGDT YYPGSVKG (SEQ ID NO: 8) | DRYSRTG HYMGMSL (SEQ ID NO: 66) |
| mAb QD37 VL | DIQMTQSPSTLSASVGDRVTITCRASQSISSWLAWYQQKPGK APKLLIYKASSLESGVPSRFSG SGSGTEFTLTISSLQPDDFATY YCQQYDTYWTFGQGTKVEIK (SEQ ID NO: 46) | RASQSISS WLA (SEQ ID NO: 1) | KASSLES (SEQ ID NO: 2) | QQYDTYW T (SEQ ID NO: 64) |
| mAb QD3 VH | EVQLVESGGGLVQPGGSLRLS CAASGFTFSSYDMHWVRQAT GKGLEWVSGIGTAGDTYYPGS VKGRFTISRENAKNSLYLQMN SLRAGDTAVYYCARDNYSRTG HYMGMDVWGQGTTVTVSS (SEQ ID NO: 47) | SYDMH (SEQ ID NO: 7) | GIGTAGDT YYPGSVKG (SEQ ID NO: 8) | DNYSRTG HYMGMDV (SEQ ID NO: 67) |
| mAb QD3 VL | DIQMTQSPSTLSASVGDRVTITCRASQSISSWLAWYQQKPGK APKLLIYKASSLESGVPSRFSG SGSGTEFTLTISSLQPDDFATY YCKQYADYWTFGQGTKVEIK (SEQ ID NO: 48) | RASQSISS WLA (SEQ ID NO: 1) | KASSLES (SEQ ID NO: 2) | KQYADYW T (SEQ ID NO: 68) |
| mAb QD4 VH | EVQLVESGGGLVQPGGSLRLS CAASGFTFSSYDMHWVRQAT GKGLEWVSGIGTAGDTYYPGS VKGRFTISRENAKNSLYLQMN SLRAGDTAVYYCARDNYSRTG HYMGMDVWGQGTTVTVSS (SEQ ID NO: 49) | SYDMH (SEQ ID NO: 7) | GIGTAGDT YYPGSVKG (SEQ ID NO: 8) | DNYSRTG HYMGMDV (SEQ ID NO: 67) |
| mAb QD4 VL | DIQMTQSPSTLSASVGDRVTITCRASQSISSWLAWYQQKPGK APKLLIYKASSLESGVPSRFSG SGSGTEFTLTISSLQPDDFATY YCQQYDTYWTFGQGTKVEIK (SEQ ID NO: 50) | RASQSISS WLA (SEQ ID NO: 1) | KASSLES (SEQ ID NO: 2) | QQYDTYW T (SEQ ID NO: 64) |
| mAb QD23 VH | EVQLVESGGGLVQPGGSLRLS CAASGFTFSSYDMHWVRQAT GKGLEWVSGIGTAGDTYYPGS VKGRFTISRENAKNSLYLQMN SLRAGDTAVYYCARDRYSPTG HYMGMSLWGQGTTVTVSS (SEQ ID NO: 51) | SYDMH (SEQ ID NO: 7) | GIGTAGDT YYPGSVKG (SEQ ID NO: 8) | DRYSPTGH YMGMSL (SEQ ID NO: 78) |

TABLE 7-continued

VL and VH amino acid sequences for anti-alpha toxin mAbs

| Description | VH or VL sequence (with CDRs in bold) | CDR1 | CDR2 | CDR3 |
|---|---|---|---|---|
| mAb QD23 VL | DIQMTQSPSTLSASVGDRVTITCRASQSISSWLAWYQQKPGK APKLLIYKASSLESGVPSRFSG SGSGTEFTLTISSLQPDDFATY YCQQYDTYWTFGQGTKVEIK (SEQ ID NO: 52) | RASQSISS WLA (SEQ ID NO: 1) | KASSLES (SEQ ID NO: 2) | QQYDTYW T (SEQ ID NO: 64) |
| mAb QD32 VH | EVQLVESGGGLVQPGGSLRLS CAASGFTFSSYDMHWVRQAT GKGLEWVSGIGTAGDTYYPGS VKGRFTISRENAKNSLYLQMN SLRAGDTAVYYCARDRYSRTG HYMGMDVWGQGTTVTVSS (SEQ ID NO: 53) | SYDMH (SEQ ID NO: 7) | GIGTAGDT YYPGSVKG (SEQ ID NO: 8) | DRYSRTG HYMGMDV (SEQ ID NO: 65) |
| mAb QD32 VL | DIQMTQSPSTLSASVGDRVTITCRASQSISSWLAWYQQKPGK APKLLIYKASSLESGVPSRFSG SGSGTEFTLTISSLQPDDFATY YCKQYADYWTFGQGTKVEIK (SEQ ID NO: 54) | RASQSISS WLA (SEQ ID NO: 1) | KASSLES (SEQ ID NO: 2) | KQYADYW T (SEQ ID NO: 68) |
| mAb 2A3GL VH | EVQLVESGGGLVQPGGSLRLS CAASGFTFSSYDMHWVRQAT GKGLEWVSGIGTAGDTYYPGS VKGRFTISRENAKNSLYLQMN SLRAGDTAVYYCARDNYSSTG GYYGMDVWGQGTTVTVSS (SEQ ID NO: 55) | SYDMH (SEQ ID NO: 7) | GIGTAGDT YYPGSVKG (SEQ ID NO: 8) | DNYSSTG GYYGMDV (SEQ ID NO: 9) |
| mAb 2A3GL VL | DIQMTQSPSTLSASVGDRVTITCRASQSISSWLAWYQQKPGK APKLLIYKASSLESGVPSRFSG SGSGTEFTLTISSLQPDDFATY YCQQYNSYWTFGQGTKVEIK (SEQ ID NO: 56) | RASQSISS WLA (SEQ ID NO: 1) | KASSLES (SEQ ID NO: 2) | QQYNSYW T (SEQ ID NO: 3) |
| mAb LC10 VH | EVQLVESGGGLVQPGGSLRLS CAASGFTFSSHDMHWVRQAT GKGLEWVSGIGTAGDTYYPDS VKGRFTISRENAKNSLYLQMN SLRAGDTAVYYCARDRYSPTG HYYGMDVWGQGTTVTVSS (SEQ ID NO: 57) | SHDMH (SEQ ID NO: 69) | GIGTAGDT YYPDSVKG (SEQ ID NO: 70) | DRYSPTGH YYGMDV (SEQ ID NO: 71) |
| mAb LC10 VL | DIQMTQSPSTLSASVGDRVTITCRASQSISSWLAWYQQKPGK APKLLIYKASSLESGVPSRFSG SGSGTEFTLTISSLQPDDFATY YCKQYADYWTFGQGTKVEIK (SEQ ID NO: 58) | RASQSISS WLA (SEQ ID NO: 1) | KASSLES (SEQ ID NO: 2) | KQYADYW T (SEQ ID NO: 68) |
| mAb TVES VH | EVQLVESGGGLVQPGGSLRLS CAASGFTFSSYDMHWVRQAT GKGLEWVSGIGTAGDTYYPGS VKGRFTISRENAKNSLYLQMN SLRAGDTAVYYCARDNYSPTG GYYGMDVWGQGTTVTVSS (SEQ ID NO: 59) | SYDMH (SEQ ID NO: 7) | GIGTAGDT YYPGSVKG (SEQ ID NO: 8) | DNYSPTG GYYGMDV (SEQ ID NO: 72) |
| mAb TVES VL | DIQMTQSPSTLSASVGDRVTITCRASQSISSWLAWYQQKPGK APKLLIYKASSLKSGVPSRFSG SGSGTEFTLTISSLQPDDFATY YCQQYESYWTFGQGTKVEIK (SEQ ID NO: 60) | RASQSISS WLA (SEQ ID NO: 1) | KASSLKS (SEQ ID NO: 73) | QQYESYW T (SEQ ID NO: 74) |
| mAb 3H7KAD VH | EVQLVESGGGLVQPGGSLRLS CAASGFTFSSHDMHWVRQAT GKGLEWVSGIGTRGDTYYPDS VKGRFTISRENAKNSLYLQMN SLRAGDTAVYYCARDRYSPTG HYYGMDVWGQGTTVTVSS (SEQ ID NO: 61) | SHDMH (SEQ ID NO: 69) | GIGTRGDT YYPDSVKG (SEQ ID NO: 75) | DRYSPTGH YYGMDV (SEQ ID NO: 71) |

TABLE 7-continued

VL and VH amino acid sequences for anti-alpha toxin mAbs

| Description | VH or VL sequence (with CDRs in bold) | CDR1 | CDR2 | CDR3 |
|---|---|---|---|---|
| mAb 3H7KAD VL | DIQMTQSPSTLSASVGDRVTIT CRASQSISSWLAWYQQKPGK APKLLIYKASSLESGVPSRFSG SGSGTEFTLTISSLQPDDFATY YCKQYADYWTFGQGTKVEIK (SEQ ID NO: 58) | RASQSISS WLA (SEQ ID NO: 1) | KASSLES (SEQ ID NO: 2) | KQYADYW T (SEQ ID NO: 68) |
| mAb LC9 VH | EVQLVESGGGLVQPGGSLRLS CAASGFTFSSHDMHWVRQAT GKGLEWVSGIGTRGDTYYPDS VKGRFTISRENAKNSLYLQMN SLRAGDTAVYYCARDKYSPTG HYYGMDVWGQGTTVTVSS (SEQ ID NO: 62) | SHDMH (SEQ ID NO: 69) | GIGTRGDT YYPDSVKG (SEQ ID NO: 75) | DKYSPTGH YYGMDV (SEQ ID NO: 76) |
| mAb LC9 VL | DIQMTQSPSTLSASVGDRVTIT CRASQSISSWLAWYQQKPGK APKLLIYKASSLESGVPSRFSG SGSGTEFTLTISSLQPDDFATY YCKQYADYWTFGQGTKVEIK (SEQ ID NO: 58) | RASQSISS WLA (SEQ ID NO: 1) | KASSLES (SEQ ID NO: 2) | KQYADYW T (SEQ ID NO: 68) |
| mAb LC4 VH | EVQLVESGGGLVQPGGSLRLS CAASGFTFSSHDMHWVRQAT GKGLEWVSGIGTRGDTYYPDS VKGRFTISRENAKNSLYLQMN SLRAGDTAVYYCARDKYSPTG HYYGMDVWGQGTTVTVSS (SEQ ID NO: 62) | SHDMH (SEQ ID NO: 69) | GIGTRGDT YYPDSVKG (SEQ ID NO: 75) | DKYSPTGH YYGMDV (SEQ ID NO: 76) |
| mAb LC4 VL | DIQMTQSPSTLSASVGDRVTIT CRASQSISSWLAWYQQKPGK APKLLIYKASSLVKGVPSRFSG SGSGTEFTLTISSLQPDDFATY YCQQYESYWTFGQGTKVEIK (SEQ ID NO: 63) | RASQSISS WLA (SEQ ID NO: 1) | KASSLVK (SEQ ID NO: 77) | QQYESYW T (SEQ ID NO: 74) |
| mAb LC5 VH | EVQLVESGGGLVQPGGSLRLS CAASGFTFSSHDMHWVRQAT GKGLEWVSGIGTAGDTYYPDS VKGRFTISRENAKNSLYLQMN SLRAGDTAVYYCARDRYSPTG HYYGMDVWGQGTTVTVSS (SEQ ID NO: 79) | SHDMH (SEQ ID NO: 69) | GIGTAGDT YYPDSVKG (SEQ ID NO: 70) | DRYSPTGH YYGMDV (SEQ ID NO: 71) |
| mAb LC5 VL | DIQMTQSPSTLSASVGDRVTIT CRASQSISSWLAWYQQKPGK APKLLIYKASSLVKGVPSRFSG SGSGTEFTLTISSLQPDDFATY YCQQYESYWTFGQGTKVEIK (SEQ ID NO: 63) | RASQSISS WLA (SEQ ID NO: 1) | KASSLVK (SEQ ID NO: 77) | QQYESYW T (SEQ ID NO: 74) |

TABLE 8

VL and VH nucleotide sequences for anti-alpha toxin mAbs

| SEQ ID NO: | Description | Sequence |
|---|---|---|
| SEQ ID NO: 29 | mAb 2A3.1 VL nucleotide sequence | GACATCCAGATGACCCAGTCTCCTTCCA CCCTGTCTGCATCTGTAGGAGACAGAGT CACCATCACTTGCCGGGCCAGTCAGAGT ATTAGTAGCTGGTTGGCCTGGTATCAGC AGAAACCAGGGAAAGCCCCTAAACTCCT GATCTATAAGGCGTCTAGTTTAGAAAGTG GGGTCCCATCAAGGTTCAGCGGCAGTGG ATCTGGGACAGAATTCACTCTCACCATCA GCAGCCTGCAGCCTGATGATTTTGCAAC TTATTACTGCCAACAGTATAATAGTTATTG GACGTTCGGCCAAGGGACCAAGGTGGA AATCAAA |

TABLE 8-continued

VL and VH nucleotide sequences for anti-alpha toxin mAbs

| SEQ ID NO: | Description | Sequence |
| --- | --- | --- |
| SEQ ID NO: 30 | mAb 2A3.1 VH nucleotide sequence | GAGGTGCAGCTGGTGGAGTCTGGGGGA GGCTTGGTACAGCCTGGGGGGTCCCTG AGACTCTCCTGTGCAGCCTCTGGATTCA CCTTCAGTAGCTACGACATGCACTGGGT CCGCCAAGCTACAGGAAAAGGTCTGGAG TGGGTCTCAGGTATTGGCACTGCTGGTG ACACATATTATCCAGGCTCCGTGAAGGG CCGATTCACCATCTCCAGAGAAAATGCC AAGAACTCCTTGTATCTTCAATTGAACAG CCTGAGAGCCGGGGACACGGCTGTGTA CTTCTGTGCAAGAGACAATTATAGCAGCA CCGGGGGGTACTACGGTATGGACGTCTG GGGCCAAGGGACCACGGTCACCGTCTC CTCA |
| SEQ ID NO: 31 | mAb 10A7.5 VL nucleotide sequence | GACATCCAGATGACCCAGTCTCCTTCCA CCCTGTCTGCATCTGTAGGAGACAGAGT CACCATCACTTGCCGGGCCAGTCAGAGT ATTAGTAGCTGGTTGGCCTGGTATCAGC AGAAACCAGGGAAAGCCCCTAAACTCCT GATCTATAAGGCGTCTAGTTTAGAAAGTG GGGTCCCATCAAGGTTCAGCGGCAGTGG ATCTGGGACAGAATTCACTCTCACCATCA GCAGCCTGCAGCCTGATGATTTTGCAAC TTATTACTGCCAACAGTATAATAGTTATTG GACGTTCGGCCAAGGGACCAAGGTGGA AATCAAA |
| SEQ ID NO: 32 | mAb 10A7.5 VH nucleotide sequence | GAGGTGCAGCTGGTGGAGTCTGGGGGA GGCTTGGTACAGCCTGGGGGGTCCCTG AGACTCTCCTGTGCAGCCTCTGGATTCA CCTTCAGTAGGTACGACATGCACTGGGT CCGCCAAGCTACAGGAAAAGGTCTGGAG TGGGTCTCAGTTATTGGTACTGATGGTGA CACATACTATCCAGGCTCCGTGAAGGGC CGATTCATCATCTCCAGAGAAAATGCCAA GAACTCCTTGTATCTTGAAATGAACAGCC TGAGAGCCGGGGACACGGCTGTGTATTA CTGTGCAAGAGATCGGTATAGCAGCTCG AACCACTACAACGGTATGGACGTCTGGG GCCAAGGGACCACGGTCACCGTCTCCTC A |
| SEQ ID NO: 33 | mAb 12B8.19 VL nucleotide sequence | GACATCCAGATGACCCAGTCTCCTTCCA CCCTGTCTGCATCTGTAGGAGACAGAGT CACCATCACTTGCCGGGCCAGTCAGAGT ATTAGTAGCTGGTTGGCCTGGTATCAGC AGAAACCAGGGAAAGCCCCTAAGGTCCT GATCTATAAGGCGTCTAGTTTAGAAAGTG GGGTCCCATCAAGGTTCAGCGGCAGTGG ATCTGGGACAGAATTCACTCTCACCATCA GCAGCCTGCAGCCTGATGATTTTGCAAC TTATTACTGCCAACAGTATAATAGTTATTG GACGTTCGGCCAAGGGACCAAGGTGGA AATCAAA |
| SEQ ID NO: 34 | mAb 12B8.19 VH nucleotide sequence | GAGGTGCAGCTGGTGGAGTCTGGGGGA GGCTTGGTACAGCCTGGGGGGTCCCTG AGACTCTCCTGTGCAGCCTCTGGATTCA CCTTCAGTAGGTACGACATGCACTGGGT CCGCCAAGCTACAGGAAAAGGTCTGGAG TGGGTCTCAGTTATTGGTACTGATGGTGA CACATACTATCCAGGCTCCGTGAAGGGC CGATTCATCATCTCCAGAGAAAATGCCAA GAACTCCTTGTATCTTGAAATGAACAGCC TGAGAGCCGGGGACACGGCTGTGTATTA CTGTGCAAGAGATCGGTATAGCAGCTCG AACCACTACAACGGTATGGACGTCTGGG GCCAAGGGACCACGGTCACCGTCTCCTC A |
| SEQ ID NO: 35 | mAb 28F6.1 VL nucleotide sequence | GCCATCCAGATGACCCAGTCTCCATCCT CCCTGTCTGCATCTGTAGGAGACAGAGT CACCATCACTTGCCGGGCAAGTCAGGGC ATTAGAAATGATTTAGGCTGGTATCAGCA GAAACCAGGGAAAGCCCCTAAGCTCCTG |

TABLE 8-continued

VL and VH nucleotide sequences for anti-alpha toxin mAbs

| SEQ ID NO: | Description | Sequence |
|---|---|---|
| | | ATCTATGATGCATCCAGTTTACAAAGTGG GGTCCCATCAAGGTTCAGCGGCAGTGGA TCTGGCACAGATTTCACTCTCACCATCAG CAGCCTGCAGCCTGAAGATTTTGCAACTT ATTACTGTCTACAAGATTACAATTACCCG TGGACGTTCGGCCAAGGGACCAAGGTG GAAATCAAA |
| SEQ ID NO: 36 | mAb 28F6.1 VH nucleotide sequence | GAGGTGCAGCTGTTGGAGTCTGGGGGA GGCTTGGTACAGCCTGGGGGGTCCCTG AGACTCTCCTGTGCAGCCTCTGGATTCA CCTTTAGCAGCTATGCCATGACCTGGGT CCGCCAGGCTCCAGGGAAGGGGCTGGA ATGGGTCTCAGTTATTAGTGGTAGTGGT GGTAGCACATACTACGCAGACTCCGTGA AGGGCCGGTTCACCGTCTCCAGAGACAA TTCCAAGAACACGCTGTATCTGCAAATGA ACAGCCTGAGAGCCGAGGACACGGCCG TATATTACTGTGCGAAAGATGGGAGGCA GGTCGAGGATTACTACTACTACACGGTA TGGACGTCTGGGGCCAAGGGACCACGG TCACCGTCTCCTCA |
| SEQ ID NO: 37 | mAb 25E9.1 VL nucleotide sequence | GACATCCAGATGACCCAGTCTCCTTCCA CCCTGTCTGCATCTGTAGGAGACAGAGT CACCATCACTTGCCGGGCCAGTCAGAGT ATTAGTAGCTGGTTGGCCTGGTATCAGC AGAAACCAGGGAAAGCCCCTAAGCTCCT GATCTATAAGGCGTCTAGTTTAGAAAGTG GGGTCCCATCAAGGTTCAGCGGCAGTGG ATCTGGGACAGAATTCACTCTCACCATCA GCAGCCTGCAGCCTGATGATTTTGCAAC TTATTACTGCCAACAGTATAATAGTTATTG GACGTTCGGCCAAGGGACCAAGGTGGA AATCAAA |
| SEQ ID NO: 38 | mAb 25E9.1 VH nucleotide sequence | GAGGTGCAGCTGGTGGAGTCTGGGGGA GGCTTGGTACAGCCTGGGGGGTCCCTG AGACTCTCCTGTACAGCCTCTGGATTCAC CTTCAGTAGTTACGACATGCACTGGGTC CGCCAAGCTACAGGAAAAGGTCTGGAGT GGGTCTCAGTTATTGATACTGCTGGTGA CACATACTATCCAGGCTCCGTGAAGGGC CGATTCACCATCTCCAGAGAAAATGCCAA GAACTCCTTGTATCTTCAAATGAACAGCC TGAGAGCCGGGGACACGGCTGTGTATTA CTGTGTAAGAGATAGGTATAGTGGGAAC TTCCACTACAACGGTATGGACGTCTGGG GCCAAGGGACCACGGTCACCGTCTCCTC A |

TABLE 9

Alpha Toxin VL and VH CDR summary table

| Description | SEQ ID NOs |
|---|---|
| VL CDR 1 | 1, 4 |
| VL CDR 2 | 2, 5, 73, 77 |
| VL CDR 3 | 3, 6, 64, 68, 74 |
| VH CDR 1 | 7, 10, 13, 69 |

TABLE 9-continued

Alpha Toxin VL and VH CDR summary table

| Description | SEQ ID NOs |
|---|---|
| VH CDR 2 | 8, 11, 14, 17, 70, 75 |
| VH CDR 3 | 9, 12, 15, 18, 16, 65, 66, 67, 71, 72, 76, 78 |

TABLE 10

VL and VH amino acid sequences for anti-alpha toxin mAbs having Fc variant region

| SEQ ID NO: | Description | Sequence |
|---|---|---|
| SEQ ID NO: 130 | LC 10-VH- IgG1-YTE | EVQLVESGGGLVQPGGSLRLSCAASG FTFSSHDMHWVRQATGKGLEWVSGIG TAGDTYYPDSVKGRFTISRENAKNSLY |

TABLE 10-continued

VL and VH amino acid sequences for anti-alpha toxin mAbs having Fc variant region

| SEQ ID NO: | Description | Sequence |
|---|---|---|
| | | LQMNSLRAGDTAVYYCARDRYSPTGH YYGMDVWGQGTTVTVSS- ASTKGPSVFPLAPSSKSTSGGTAALGC LVKDYFPEPVTVSWNSGALTSGVHTFP AVLQSSGLYSLSSVVTVPSSSLGTQTYI CNVNHKPSNTKVDKRVEPKSCDKTHT CPPCPAPELLGGPSVFLFPPKPKDTLYI TREPEVTCVVVDVSHEDPEVKFNWYV DGVEVHNAKTKPREEQYNSTYRVVSVL TVLHQDWLNGKEYKCKVSNKALPAPIE KTISKAKGQPREPQVYTLPPSREEMTK NQVSLTCLVKGFYPSDIAVEWESNGQP ENNYKTTPPVLDSDGSFFLYSKLTVDK SRWQQGNVFSCSVMHEALHNHYTQK SLSLSPGK |
| SEQ ID NO: 131 | LC10 VL-Kappa | DIQMTQSPSTLSASVGDRVTITCRASQ SISSWLAWYQQKPGKAPKLLIYKASSLE SGVPSRFSGSGSGTEFTLTISSLQPDD FATYYCKQYADYWTFGQGTKVEIK- RTVAAPSVFIFPPSDEQLKSGTASVVCL LNNFYPREAKVQWKVDNALQSGNSQE SVTEQDSKDSTYSLSSTLTLSKADYEK HKVYACEVTHQGLSSPVTKSFNRGE |

TABLE 11

Alpha Toxin Amino Acid Sequences

| *Staphylococcus aureus* alpha toxin | adsdiniktgttdigsnttvktgdlvtydkengmhkkvfysfiddknhnkkllvirtkgtiagqyrvyseega nksglawpsafkvqlqlpdnevaqisdyyprnsidtkeymstltygfngnvtgddtgkiggliganvsigh tlkyvqpdfktilesptdkkvgwkvifnnmvnqnwgpydrdswnpvygnqlfmktrngsmkaadnfld pnkassllssgfspdfatvitmdrkaskqqtnidviyervrddyqlhwtstnwkgtntkdkwtdrsseryki dwekeemtn (SEQ ID NO: 39) |
|---|---|
| *S. aureus* alpha toxin H35L mutant | adsdiniktgttdigsnttvktgdlvtydkengmlkkvfysfiddknhnkkllvirtkgtiagqyrvyseegan ksglawpsafkvqlqlpdnevaqisdyyprnsidtkeymstltygfngnvtgddtgkiggliganvsightl kyvqpdfktilesptdkkvgwkvifnnmvnqnwgpydrdswnpvygnqlfmktrngsmkaadnfldp nkassllssgfspdfatvitmdrkaskqqtnidviyervrddyqlhwtstnwkgtntkdkwtdrsserykid wekeemtn (SEQ ID NO: 40) |

TABLE 12

Representative Amino Acid Sequences for Antibodies that Specifically Bind to *S. aureus* surface antigen IsdH

| Description | VH or VL sequence (with CDRs in bold) | CDR1 | CDR2 | CDR3 |
|---|---|---|---|---|
| mAb 2F4 VH | EVQLLESGGGLVQPGGSLRLS CAASGFTFSPYMMQWVRQAP GKGLEWVSSIWPSGGKTYYA DSVKGRFTISRDNSKNTLY LQMNSLRAEDTAVYYCARVRR GGATDYWGQGTLVTVSS (SEQ ID NO: 80) | PYMMQ (SEQ ID NO: 90) | SIWPSGGK TYYADSVK G (SEQ ID NO: 91) | VRRGGAT DY (SEQ ID NO: 92) |
| mAb 2F4 VL | DIQMTQSPATLSVSPGERATL SCRASQSVSSNLGWYQQKPG QAPRLLIYGASTRATGIPTRFS GSGSGTEFTLTISSLQS EDFATYYCQQYQNWPLLTFG GGTKVEIK (SEQ ID NO: 81) | RASQSVSS NLG (SEQ ID NO: 93) | GASTRAT (SEQ ID NO: 94) | QQYQNWP LLT (SEQ ID NO: 95) |
| mAb A7 VH | EVQLLESGGGLVQPGGSLRLS CAASGFTFSNYYMWWVRQAP GKGLEWVSVIGPSGGPTQYA | NYYMW (SEQ ID NO: 96) | VIGPSGGP TQYADSVK G (SEQ ID NO: 97) | WGGRYSV FET (SEQ ID NO: 98) |

TABLE 12-continued

Representative Amino Acid Sequences for Antibodies that Specifically Bind to *S. aureus* surface antigen IsdH

| Description | VH or VL sequence (with CDRs in bold) | CDR1 | CDR2 | CDR3 |
|---|---|---|---|---|
| | DSVKGRFTISRDNSKNTLY LQMNSLRAEDTAVYYCARWG GRYSVFETWGQGTMVTVSS (SEQ ID NO: 82) | | NO: 97) | |
| mAb A7 VL | DIQMTQSPATLSVSPGGRATL SCRASQSVRKNVAWYQQKPG QPPRLLIYGASTRATGVPARF SGSGSGTEFTLTISRMQP EDFVVYHCQQYSSWPAFGQG TMVEIN (SEQ ID NO: 83) | RASQSVR KNVA (SEQ ID NO: 99) | GASTRAT (SEQ ID NO: 100) | QQYSSWP AF (SEQ ID NO: 101) |
| mAb 1C1 VH | EVQLLESGGGLVQPGGSLRLS CAASGFTFSRYFMGWVRQAP GKGLEWVSSIYSSGGYTSYAD SVKGRFTISRDNSKNTLY LQMNSLRAEDTAVYYCARRW RDGTFDYWGQGTLVTVSS (SEQ ID NO: 84) | RYFMG (SEQ ID NO: 102) | SIYSSGGY TSYADSVK G (SEQ ID NO: 103) | RWRDGTF DY (SEQ ID NO: 104) |
| mAb 1C1 VL | DIQMTQSPSSLSASIGDRVTIS CRASQSVREYLNWYQQKPGK APKLLIFAASSLQSGVPSRFSG SGSGTDFTLTISSLQP EDFATYYCQQSYSTRFTFGPG TKVDIK (SEQ ID NO: 85) | RASQSVR EYLN (SEQ ID NO: 105) | AASSLQS (SEQ ID NO: 106) | QQSYSTRF T (SEQ ID NO: 107) |
| IsdH0003 VH | QVQLQQSGAEVKKPGSSVKV SCKASGGTFSSYPISWVRQAP GQGLEWMGKIIPIFGTTNYAQ KFQGRVTITADESTSTAY MELSSLRSEDTAIYYCASPNRP YNIGWHYYFDYWGKGTLVTVS S (SEQ ID NO: 86) | SYPIS (SEQ ID NO: 108) | KIIPIFGTTN YAQKFQG (SEQ ID NO: 109) | PNRPYNIG WHYYFDY (SEQ ID NO: 110) |
| IsdH0003 VL | QSVLTQPASVSGSPGQSITISC TGTSSDVGGYNYVSWYQQHP GKAPKLMIYEGSKRPSGVSNR FSGSRSGNTASLTISGL QAEDEADYYCSSYTTRSTRVF GGGTKLTVL (SEQ ID NO: 87) | TGTSSDVG GYNYVS (SEQ ID NO: 111) | EGSKRPS (SEQ ID NO: 112) | SSYTTRST RV (SEQ ID NO: 113) |
| IsdH0016 VH | EVQLLESGGGLVQPGGSLRLS CAASGFTFSSYAMSWVRQAP GKGLEWVSAISGSGGSTYYAD SVKGRFTISRDNSKNTLY LQMNSLRAEDTAVYYCARDQ DEGRANNWWIPPGGRWGQG TMVTVSS (SEQ ID NO: 88) | SYAMS (SEQ ID NO: 114) | AISGSGGS TYYADSVK G (SEQ ID NO: 115) | DQDEGRA NNWWIPP GGR (SEQ ID NO: 116) |
| IsdH0016 VL | SSELTQDPTLSVALGQTVRITC QGDSLRRSFASWYQKKPGQA PVLLIYGQNKRPAGIPDRFSGS RSGNSASLTITGAQ AEDEADYYCNSRDARLNPYIL FGGGTKLTVL (SEQ ID NO: 89) | QGDSLRR SFAS (SEQ ID NO: 117) | GQNKRPA (SEQ ID NO: 118) | NSRDARL NPYIL (SEQ ID NO: 119) |

TABLE 13 nucleotide sequences encoding VH and VL amino acid sequences for mAbs directed against *S. aureus* surface antigen IsdH and ClfA

| SEQ ID NO: | Description | Sequence |
|---|---|---|
| SEQ ID NO: 120 | mAb 2F4 VH nucleotide sequence | GAAGTTCAATTGTTAGAGTCTGGTGG CGGTCTTGTTCAGCCTGGTGGTTCTT TACGTCTTTCTTGCGCTGCTTCCGGA TTCACTTTCTCTCCTTACATGATGCAG TGGGTTCGCCAAGCTCCTGGTAAAGG TTTTGGAGTGGGTTTCTTCTATCTGGC CTTCTGGTGGCAAGACTTATTATGCT GACTCCGTTAAAGGTCGCTTCACTAT CTCTAGAGACAACTCTAAGAATACTCT CTACTTGCAGATGAACAGCTTAAGGG CTGAGGACACGGCCGTGTATTACTGT GCGAGAGTGCGGAGGGGGGAGCT ACTGACTACTGGGGCCAGGGAACCC TGGTCACCGTCTCAAGC |
| SEQ ID NO: 121 | mAb 2F4 VL nucleotide sequence | GACATCCAGATGACCCAGTCTCCAGC CACCCTGTCTGTGTCTCCAGGGGAAA GAGCCACCCTCTCCTGCAGGGCCAG TCAGAGTGTTAGCAGCAACTTAGGCT GGTACCAGCAGAAACCTGGCCAGGC TCCCAGGCTCCTCATCTATGGTGCAT CCACCAGGGCCACTGGTATCCCAAC CAGGTTCAGTGGCAGTGGGTCTGGG ACAGAGTTCACTCTCACCATCAGCAG CCTGCAGTCTGAAGATTTTGCAACTT ATTACTGTCAGCAGTATCAGAACTGG CCCTTGCTCACTTTCGGCGGAGGGA CCAAGGTGGAAATCAAA |
| SEQ ID NO: 122 | mAb A7 VH nucleotide sequence | GAAGTTCAATTGTTAGAGTCTGGTGG CGGTCTTGTTCAGCCTGGTGGTTCTT TACGTCTTTCTTGCGCTGCTTCCGGA TTCACTTTCTCTAATTACTATATGTGG TGGGTTCGCCAAGCTCCTGGTAAAGG TTTTGGAGTGGGTTTCTGTTATCGGTC CTTCTGGTGGCCCTACTCAGTATGCT GACTCCGTTAAAGGTCGCTTCACTAT CTCTAGAGACAACTCTAAGAATACTCT CTACTTGCAGATGAACAGCTTAAGGG CTGAGGACACGGCCGTGTATTACTGT GCGAGATGGGTGGGAGGTACTCTG TATTTGAAACCTGGGGCCAAGGGACA ATGGTCACCGTCTCAAGC |
| SEQ ID NO: 123 | mAb A7 VL nucleotide sequence | GACATCCAGATGACCCAGTCTCCAGC CACTCTGTCTGTGTCTCCAGGGGGAA GAGCCACCCTCTCCTGCAGGGCCAG TCAGAGTGTTAGAAAAAACGTAGCCT GGTATCAGCAGAAACCTGGCCAGCCT CCCAGGCTCCTCATCTATGGTGCATC CACCAGGGCCACTGGTGTCCCAGCC AGGTTCAGTGGCAGTGGGTCTGGGA CAGAGTTCACTCTCACCATCAGCAGG ATGCAGCCTGAAGATTTTGTAGTTTAT CACTGTCAGCAGTATAGTAGCTGGCC GGCGTTCGGCCAGGGGACCATGGTG GAAATCAAC |
| SEQ ID NO: 124 | mAb 1C1 VH nucleotide sequence | GAAGTTCAATTGTTAGAGTCTGGTGG CGGTCTTGTTCAGCCTGGTGGTTCTT TACGTCTTTCTTGCGCTGCTTCCGGA TTCACTTTCTCTCGTTACTTTATGGGT TGGGTTCGCCAAGCTCCTGGTAAAGG TTTTGGAGTGGGTTTCTTCTATCTATTC TTCTGGTGGCTATACTTCTTATGCTGA CTCCGTTAAAGGTCGCTTCACTATCT CTAGAGACAACTCTAAGAATACTCTCT ACTTGCAGATGAACAGCTTAAGGGCT GAGGACACGGCCGTGTATTACTGTGC GAGACGGTGGCGAGATGGCACCTTT GACTACTGGGGCCAGGGAACCCTGG TCACCGTCTCAAGC |
| SEQ ID NO: 125 | mAb 1C1 VL nucleotide sequence | GACATCCAGATGACCCAGTCTCCATC CTCCCTGTCTGCATCTATTGGAGACA |

TABLE 13-continued nucleotide sequences encoding VH and VL amino acid sequences for mAbs directed against *S. aureus* surface antigen IsdH and ClfA

| SEQ ID NO: | Description | Sequence |
|---|---|---|
| | | GAGTCACCATCTCTTGCCGGGCAAGT CAGAGCGTTAGAGAGTATCTAAATTG GTATCAACAAAAACCAGGGAAAGCCC CTAAACTCCTGATCTTTGCTGCATCCA GTTTGCAGAGTGGGGTCCCATCAAGA TTCAGTGGCAGTGGATCTGGGACAGA TTTCACTCTCACCATCAGCAGTCTGC AACCTGAAGATTTTGCAACTTATTACT GTCAACAGAGTTACAGTACCCGATTC ACTTTCGGCCCTGGGACCAAAGTGGA CATCAAA |
| SEQ ID NO: 126 | mAb IsdH0003 VH nucleotide sequence | CAGGTACAGCTGCAGCAGTCAGGGG CTGAGGTGAAGAAGCCTGGGTCCTC GGTGAAGGTCTCCTGCAAGGCTTCTG GAGG CACCTTCAGCAGCTATCCTATCAGCT GGGTGCGACAGGCCCCTGGACAAGG GCTTGAGTGGATGGGAAAGATCATCC CTA TCTTTGGTACAACAAACTACGCGCAG AAGTTCCAGGGCAGAGTCACGATTAC CGCGGACGAATCCACGAGCACTGCC TAC ATGGAACTGAGCAGCCTGAGATCTGA GGACACGGCCATATATTACTGTGCGA GCCCCAATCGACCCTATAACATTGGC TG GCACTACTACTTTGACTACTGGGGCA AAGGAACCCTGGTCACCGTCTCCTCA |
| SEQ ID NO: 127 | mAb IsdH0003 VL nucleotide sequence | CAGTCTGTGCTGACTCAGCCTGCCTC CGTGTCTGGGTCTCCTGGACAGTCGA TCACCATCTCCTGCACTGGAACCAGC AGTGACGTTGGTGGTTATAACTATGT CTCCTGGTACCAACAACACCCAGGCA AAGCCCCCAAACTCATGATTTATGAG GGCAGTAAGCGGCCCTCAGGGGTTT CTAATCGCTTCTCTGGCTCCAGGTCT GGCAACACGGCCTCCCTGACAATCTC TGGGCTCCAGGCTGAGGACGAGGCT GATTATTACTGCAGCTCATATACAACC AGGAGCACTCGAGTCTTCGGCGGAG GGACCAAGCTGACCGTCCTA |
| SEQ ID NO: 128 | mAb IsdH0016 VH nucleotide sequence | GAGGTGCAGCTGTTGGAGTCTGGGG GAGGCTTGGTACAGCCTGGGGGGTC CCTGAGACTCTCCTGTGCAGCCTCTG GATTCACCTTTAGCAGCTATGCCATG AGCTGGGTCCGCCAGGCTCCAGGGA AGGGGCTGGAGTGGGTCTCAGCTAT TAGTGGTAGTGGTGGTAGCACATACT ACGCAGACTCCGTGAAGGGCCGGTT CACCATCTCCAGAGACAATTCCAAGA ACACGCTGTATCTGCAAATGAACAGC CTGAGAGCCGAGGACACGGCCGTGT ATTACTGTGCAAGAGATCAGGACGAA GGTAGAGCGAACAACTGGTGGATCC CCCCCGGGGGTCGCTGGGGCCAGG GGACAATGGTCACCGTCTCGAGT |
| SEQ ID NO: 129 | mAb IsdH0016 VL nucleotide sequence | TCTTCTGAGCTGACTCAGGACCCTAC TCTGTCTGTGGCCCTGGGACAGACA GTCAGAATCACATGCCAAGGAGACAG CCTCCGAAGATCTTTTGCAAGTTGGT ACCAGAAGAAGCCAGGACAGGCCCC TGTACTTCTCATCTATGGTCAAAATAA GCGGCCCGCAGGGATCCCAGACCGA TTCTCTGGCTCCAGGTCAGGAAACTC AGCTTCGTTGACCATCACAGGGGCTC AGGCGGAAGATGAGGCTGACTATTAC TGTAATTCCCGCGACGCCAGACTTAA CCCTTATATACTCTTCGGCGGTGGGA CCAAGCTGACCGTCCTA |

TABLE 14

Representative Amino Acid Sequences for Antibodies that Specifically Bind to *S. aureus* surface antigen ClfA

| Description | VH or VL sequence (with CDRs in bold) | CDR1 | CDR2 | CDR3 |
|---|---|---|---|---|
| mAb 23D6 VH | QVQLVESGGGVVQPGRSLRL SCAASVFTFSSYGMHWVRQA PGKGLEWVA**LIWF 5. The isolated antibody or antigen binding fragment thereof of embodiment 4, wherein the VH amino acid sequence is identical to, or comprises 1 to 10 amino acid residue mutations relative to, the amino acid sequence of SEQ ID NO: 80, 82, 84, 86, or 88.

6. An isolated antibody or antigen binding fragment thereof that specifically binds to the *Staphylococcus aureus* (*S. aureus*) IsdH surface determinant antigen, wherein the VL amino acid sequence is at least 80%, 85%. 90%, 95% or 100% identical to the amino acid sequence of SEQ ID NO: 81, 83, 85, 87, or 89.

7. The isolated antibody or antigen binding fragment thereof of embodiment 6, wherein the VL amino acid sequence is identical to, or comprises 1 to 10 amino acid residue mutations relative to, the amino acid sequence of SEQ ID NO: 81, 83, 85, 87, or 89.

8. An isolated antibody or antigen binding fragment thereof of any one of embodiments 1-7, wherein the VH amino acid sequence is at least 80%, 85%. 90%, 95% or 100% identical to the amino acid sequence of SEQ ID NO: 80, 82, 84, 86, or 88 and the VL amino acid sequence is at least 80%, 85%. 90%, 95% or 100% identical to the amino acid sequence of SEQ ID NO: 81, 83, 85, 87, or 89.

9. The isolated antibody or antigen binding fragment thereof of embodiment 8, wherein the VH amino acid sequence corresponds to the amino acid sequence of SEQ ID NO: 80, 82, 84, 86, or 88 and the VL amino acid sequence corresponds to the amino acid sequence of SEQ ID NO: 81, 83, 85, 87, or 89.

10. The isolated antibody or antigen binding fragment thereof of any one of embodiments 1-8, wherein the VH and VL are selected from the group consisting of SEQ ID NOs: 80 and 81; SEQ ID NOs: 82 and 83; SEQ ID NOs: 84 and 85; SEQ ID NOs: 86 and 87; and SEQ ID NOs: 88 and 89.

11. The isolated antibody of fragment of any one of embodiments 1-3, wherein the VH CDR1, VH CDR2, VH CDR3, VL CDR1, VL CDR2 and VL CDR3 corresponds to the set of amino acid sequences selected from the group consisting of SEQ ID NOs: 90, 91, 92, 93, 94 and 95.

12. The isolated antibody or antigen binding fragment thereof of embodiment 1 or 2, wherein the VH amino acid sequence comprises four VH framework regions (FR1, FR2, FR3, FR4), and wherein the four VH framework regions have amino acid sequences that are at least about 80%, 85%. 90%, 95% or 100% identical to the corresponding amino acid sequences of the four VH framework regions in SEQ ID NO: 80, 82, 84, 86, or 88.

13. The isolated antibody or antigen binding fragment thereof of embodiment 1 or 2, wherein the VL amino acid sequence comprises four VL framework regions (FR1, FR2, FR3, FR4), and wherein the four VL framework regions have amino acid sequences that are at least about 80%, 85%. 90%, 95% or 100% identical to the corresponding amino acid sequences of the four VL framework regions in SEQ ID NO: 81, 83, 85, 87, or 89.

14. The isolated antibody or antigen binding fragment thereof of embodiment 1 or 2, wherein the four VH framework regions have amino acid sequences that are at least about 80%, 85%. 90%, 95% or 100% identical to the corresponding amino acid sequences of the four VH framework regions in SEQ ID NO: 80, 82, 84, 86, or 88, and wherein the four VL framework regions have amino acid sequences that are at least about 80%, 85%. 90%, 95% or 100% identical to the corresponding amino acid sequences of the four VL framework regions in SEQ ID NO: 81, 83, 85, 87, or 89.

15. The isolated antibody or antigen binding fragment thereof of any of embodiments 1-14, wherein the VH and VL correspond to SEQ ID NOs 80 and 81.

16. The isolated antibody or antigen binding fragment thereof of any one of embodiments 1-15, wherein the antibody or antigen binding fragment thereof has at least one of:
   a. a disassociation constant (KD) for an *S. aureus* surface antigen of about 70 nM or less;
   b. an ability to reduce the capability of *S. aureus* to evade opsonophagocytosis by at least 50%, as measured by an opsonophagocytic killing assay; or
   c. an ability to reduce the number of *S. aureus* colony forming units (CFUs) by at least 50%, as measured by a bacteremia model.

17. An isolated antibody or antigen binding fragment thereof that specifically binds to the *Staphylococcus aureus* (*S. aureus*) IsdH surface determinant antigen, and wherein the antibody or antigen binding fragment thereof has at least one of:
   a. a disassociation constant (KD) for an *S. aureus* surface antigen of about 70 nM or less;
   b. an ability to reduce the capability of *S. aureus* to evade opsonophagocytosis by at least 50%, as measured by an opsonophagocytic killing assay;
   c. an ability to reduce the number of *S. aureus* colony forming units (CFUs) by at least 50%, as measured by a bacteremia model;
   d. an ability to reduce immune cell infiltration, bacterial burden, and pro-inflammatory cytokine release, as measured in an animal organ burden model.

18. An isolated antibody or antigen binding fragment thereof of embodiment 17, having the amino acid sequence of the antibody or antigen binding fragment thereof of any one of embodiments 1-16.

19. A composition comprising the isolated antibody or antigen binding fragment thereof of any one of embodiments 1-18, and a pharmaceutically acceptable excipient.

20. An isolated nucleic acid encoding the amino acid sequence of any one of embodiments 1-15.

21. An isolated antibody or antigen binding fragment thereof that specifically binds to the *Staphylococcus aureus* (*S. aureus*) ClfA surface determinant antigen,
   wherein the isolated antibody or antigen binding fragment thereof comprises a heavy chain variable region (VH) and a light chain variable region (VH), each of which comprises three complementarity determining regions (CDR1, CDR2, and CDR3) and wherein:
   a. a VH CDR1 is identical to, or comprises 1, 2, or 3 amino acid residue mutations relative to, the amino acid sequence of SEQ ID NO: 133 or 141;
   b. a VH CDR2 is identical to, or comprises 1, 2, or 3 amino acid residue mutations relative to, the amino acid sequence of SEQ ID NO: 134 or 142; and
   c. a VH CDR3 is identical to, or comprises 1, 2, or 3 amino acid residue mutations relative to, the amino acid sequence of SEQ ID NO: 135 or 143;
   and/or
   d. a VL CDR1 is identical to, or comprises 1, 2, or 3 amino acid residue mutations relative to, the amino acid sequence of SEQ ID NO: 137 or 145;
   e. a VL CDR2 is identical to, or comprises 1, 2, or 3 amino acid residue mutations relative to, the amino acid sequence of SEQ ID NO: 138 or 146; and
   f. a VL CDR3 is identical to, or comprises 1, 2, or 3 amino acid residue mutations relative to, the amino acid sequence of SEQ ID NO: 139 or 147.

22. The isolated antibody or antigen binding fragment thereof of embodiment 21, wherein the isolated antibody or antigen binding fragment thereof comprises:
   a. a VH CDR1 identical to, or comprising 1, 2, or 3 amino acid residue mutations relative to, the amino acid sequence of SEQ ID NO: 133 or 141
   b. a VH CDR2 identical to, or comprising 1, 2, or 3 amino acid residue mutations relative to, the amino acid sequence of SEQ ID NO: 134 or 142;
   c. a VH CDR3 identical to, or comprising 1, 2, or 3 amino acid residue mutations relative to, the amino acid sequence of SEQ ID NO: 135 or 143;
   d. a VL CDR1 identical to, or comprising 1, 2, or 3 amino acid residue mutations relative to, the amino acid sequence of SEQ ID NO: 137 or 145;
   e. a VL CDR2 identical to, or comprising 1, 2, or 3 amino acid residue mutations relative to, the amino acid sequence of SEQ ID NO: 138 or 146; and
   f. a VL CDR3 identical to, or comprising 1, 2, or 3 amino acid residue mutations relative to, the amino acid sequence of SEQ ID NO: 139 or 147.

23. The isolated antibody or antigen binding fragment thereof of embodiment 21 or 22, wherein the VH CDR1, VH CDR2, VH CDR3, VL CDR1, VL CDR2 and VL CDR3 corresponds to the set of amino acid sequences selected from the group consisting of SEQ ID NOs: 133, 134, 135, 137, 138 and 139; and SEQ ID NOs: 137, 138, 139, 145, 146 and 147.

24. An isolated antibody or antigen binding fragment thereof that specifically binds to the *Staphylococcus aureus* (*S. aureus*) ClfA surface determinant antigen, wherein the VH amino acid sequence is at least 80%, 85%. 90%, 95% or 100% identical to the amino acid sequence of SEQ ID NO: 132 or 140.

25. The isolated antibody or antigen binding fragment thereof of embodiment 24, wherein the VH amino acid sequence is identical to, or comprises 1 to 10 amino acid residue mutations relative to, the amino acid sequence of SEQ ID NO: 132 or 140.

26. An isolated antibody or antigen binding fragment thereof that specifically binds to the *Staphylococcus aureus* (*S. aureus*) ClfA surface determinant antigen, wherein the VL amino acid sequence is at least 80%, 85%. 90%, 95% or 100% identical to the amino acid sequence of SEQ ID NO: 136 or 144.

27. The isolated antibody or antigen binding fragment thereof of embodiment 26, wherein the VL amino acid sequence is identical to, or comprises 1 to 10 amino acid residue mutations relative to, the amino acid sequence of SEQ ID NO: 136 or 144.

28. An isolated antibody or antigen binding fragment thereof of any one of embodiments 21-27, wherein the VH amino acid sequence is at least 80%, 85%. 90%, 95% or 100% identical to the amino acid sequence of SEQ ID NO: 132 or 140 and the VL amino acid sequence is at least 80%, 85%. 90%, 95% or 100% identical to the amino acid sequence of SEQ ID NO: 136 or 144.

29. The isolated antibody or antigen binding fragment thereof of embodiment 28, wherein the VH amino acid sequence corresponds to the amino acid sequence of SEQ ID NO: 132 or 140; and the VL amino acid sequence corresponds to the amino acid sequence of SEQ ID NO: 136 or 144.

30. The isolated antibody or antigen binding fragment thereof of any one of embodiments 21-28, wherein the VH and VL are selected from the group consisting of SEQ ID NOs: 132 and 136; and SEQ ID NOs: 140 and 144.

31. The isolated antibody of fragment of any one of embodiments 21-23, wherein the VH CDR1, VH CDR2, VH CDR3, VL CDR1, VL CDR2 and VL CDR3 corresponds to the set of amino acid sequences selected from the group consisting of SEQ ID NOs: 141, 142, 143, 144, 145, 146 and 147.

32. The isolated antibody or antigen binding fragment thereof of embodiment 21 or 22, wherein the VH amino acid sequence comprises four VH framework regions (FR1, FR2, FR3, FR4), and wherein the four VH framework regions have amino acid sequences that are at least about 80%, 85%. 90%, 95% or 100% identical to the corresponding amino acid sequences of the four VH framework regions in SEQ ID NO: 132 or 140.

33. The isolated antibody or antigen binding fragment thereof of embodiment 21 or 22, wherein the VL amino acid sequence comprises four VL framework regions (FR1, FR2, FR3, FR4), and wherein the four VL framework regions have amino acid sequences that are at least about 80%, 85%. 90%, 95% or 100% identical to the corresponding amino acid sequences of the four VL framework regions in SEQ ID NO: 136 or 144.

34. The isolated antibody or antigen binding fragment thereof of embodiment 21 or 22, wherein the four VH framework regions have amino acid sequences that are at least about 80%, 85%. 90%, 95% or 100% identical to the corresponding amino acid sequences of the four VH framework regions in SEQ ID NO: 132 or 144, and wherein the four VL framework regions have amino acid sequences that are at least about 80%, 85%. 90%, 95% or 100% identical to the corresponding amino acid sequences of the four VL framework regions in SEQ ID NO: 136 or 144.

35. The isolated antibody or antigen binding fragment thereof of any of embodiments 21-34, wherein the VH and VL correspond to SEQ ID NOs 140 and 144.

36. A composition comprising the isolated antibody or antigen binding fragment thereof of any one of embodiments 21-35, and a pharmaceutically acceptable excipient.

37. An isolated nucleic acid encoding the amino acid sequence of any one of embodiments 21-35.

38. A composition comprising an isolated antibody or antigen binding fragment thereof that specifically binds to an *S. aureus* alpha toxin (AT) and an isolated antibody or antigen binding fragment thereof that specifically binds to an *S. aureus* surface determinant antigen.

39. The composition of embodiment 38, wherein the *S. aureus* surface determinant antigen is selected from the group consisting of SdrC, SdrD, SdrE, ClfA, ClfB, IsdA, IsdB, IsdC, IsdE, IsdH, SpA, FnbA and PNAG.

40. The composition of embodiment 38 or 39, wherein the surface determinant antigen is IsdH.

41. The composition of embodiment 40, wherein the isolated antibody or antigen binding fragment thereof that specifically binds IsdH is an antibody or antigen binding fragment thereof according to any one of embodiments 1-18.

42. The composition of embodiment 38 or 39, wherein the surface determinant antigen is ClfA.

43. The composition of embodiment 42, wherein the isolated antibody or antigen binding fragment thereof that specifically binds ClfA is an antibody or antigen binding fragment thereof according to any one of embodiments 21-35.

44. The composition of any of embodiments 38-43, wherein the isolated antibody or antigen binding fragment thereof that specifically binds AT comprises:

a. a VH CDR1 comprising an amino acid sequence identical to or comprising 1, 2, or 3 amino acid residue mutations relative to SEQ ID NO 7, 10, 13, or 69;
b. a VH CDR2 comprising an amino acid sequence identical to or comprising 1, 2, or 3 amino acid residue mutations relative to SEQ ID NO 8, 11, 14, 17, 70, or 75; and
c. a VH CDR3 comprising an amino acid sequence identical to or comprising 1, 2, or 3 amino acid residue mutations relative to SEQ ID NO 9, 12, 15, 16, 18, 65, 66, 67, 71, 72, 76, or 78;
and/or
d. a VL CDR1 comprising the amino acid sequence of SEQ ID NO: 1 or 4;
e. a VL CDR2 comprising the amino acid sequence of SEQ ID NO: 2, 5, 73 or 77;
and
f. a VL CDR3 comprising the amino acid sequence of SEQ ID NO: 3, 6, 64, 68 or 74.

45. The composition of any of embodiments 38-43, wherein the isolated antibody or antigen binding fragment thereof that specifically binds AT comprises:
a. a VH CDR1 comprising the amino acid sequence of SEQ ID NO: 7, 10, 13 or 69;
b. a VH CDR2 comprising the amino acid sequence of SEQ ID NO: 8, 11, 14, 17, 70 or 75;
c. a VH CDR3 comprising the amino acid sequence of SEQ ID NO: 9, 12, 15, 18, 16, 65, 66, 67, 71, 72, 76 or 78;
d. a VL CDR1 comprising the amino acid sequence of SEQ ID NO: 1 or 4;
e. a VL CDR2 comprising the amino acid sequence of SEQ ID NO: 2, 5, 73 or 77;
and
f. a VL CDR3 comprising the amino acid sequence of SEQ ID NO: 3, 6, 64, 68 or 74.

46. The composition of any one of embodiments 38-45, wherein the VH CDR1, VH CDR2, VH CDR3, VL CDR1, VL CDR2 and VL CDR3 of the isolated antibody or antigen binding fragment thereof that specifically binds AT corresponds to the amino acid sequences of SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs; 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; SEQ ID NOs: 69, 70, 71, 1, 77 and 74.

47. The composition of any one of embodiments 38-43, wherein the isolated antibody or antigen binding fragment thereof that specifically binds AT comprises a heavy chain variable domain having at least 90% identity to the amino acid sequence of SEQ ID NO: 20, 22, 24, 26, 28, 41, 43, 45, 47, 49, 51, 53, 55, 57, 79, 59, 61, or 62 and/or (iii) comprises a light chain variable domain having at least 90% identity to the amino acid sequence of SEQ ID NO: 19, 21, 23, 25, 27, 42, 44, 46, 48, 50, 52, 54, 56, 58, 60 or 63.

48. The composition of any one of embodiments 38-43, wherein the isolated antibody or antigen binding fragment thereof that specifically binds AT comprises a heavy chain variable domain having the amino acid sequence of SEQ ID NO: 20, 22, 24, 26, 28, 41, 43, 45, 47, 49, 51, 53, 55, 57, 79, 59, 61, or 62 and (iii) comprises a light chain variable domain having the amino acid sequence of SEQ ID NO: 19, 21, 23, 25, 27, 42, 44, 46, 48, 50, 52, 54, 56, 58, 60 or 63.

49. The composition of any one of embodiments 38-48, wherein the VH CDR1, VH CDR2, VH CDR3, VL CDR1, VL CDR2 and VL CDR3 of the isolated antibody or antigen binding fragment thereof that specifically binds AT corresponds to the amino acid sequences of SEQ ID NOs: 69, 70, 71, 1, 2 and 68.

50. The composition of any one of embodiments 38-49, wherein the isolated antibody or antigen binding fragment thereof that specifically binds AT comprises a heavy chain variable domain having the amino acid sequence of SEQ ID NO: 57 and comprises the light chain variable domain having the amino acid sequence of SEQ ID NO: 58.

51. The composition of any one of embodiment 38-50, wherein the isolated antibody or antigen binding fragment thereof hat specifically binds AT, further comprises an Fc variant region.

52. The composition of embodiment 51, wherein the isolated antibody or antigen binding fragment thereof that specifically binds AT comprises SEQ ID NO: 130 and SEQ ID NO: 131.

53. The composition of any of embodiments 30 or 40-41, further comprising an isolated antibody or antigen binding fragment thereof that specifically binds to ClfA.

54. The composition of embodiment 53, wherein the isolated antibody or antigen binding fragment thereof that specifically binds ClfA is an antibody or antigen binding fragment thereof according to any one of embodiments 21-35.

55. A method of determining the presence of S. aureus in a test sample, comprising contacting the test sample with the isolated antibody or antigen binding fragment thereof of any one of embodiments 1-15 or 21-34 and a detectable label.

56. The method of embodiment 55, comprising:
a. contacting the test sample with the antibody or antigen binding fragment thereof, wherein the antibody or antigen binding fragment thereof binds to an S. aureus surface determinant antigen, so as to form a first complex;
b. contacting the complex with the detectable label, wherein the detectable label binds to the antibody or antigen binding fragment thereof, or to the antigen, so as to form a second complex; and
c. detecting the presence of S. aureus in the test sample based on the signal generated by the detectable label in the second complex, wherein the presence of S. aureus is directly correlated with the signal generated by the detectable label.

57. The method of embodiment 55, comprising:
a. contacting the test sample with the antibody or antigen binding fragment thereof, wherein the antibody or antigen binding fragment thereof binds to an S. aureus surface determinant antigen, so as to form a first complex;
b. contacting the complex with the detectable label, wherein the detectable label competes with the antigen for binding to the antibody or antigen binding fragment thereof so as to form a second complex; and
c. detecting the presence of S. aureus in the test sample based on the signal generated by the detectable label in the second complex, wherein the presence of S. aureus is indirectly correlated with the signal generated by the detectable label.

58. The method of any of embodiments 55-57, wherein the sample is a patient sample and the method further comprises diagnosing a patient with an S. aureus infection.

59. The method of any one of embodiments 55-58, wherein the method is adapted for use in an automated system or a semi-automated system.

60. A method of determining the presence of *S. aureus* in a test sample, comprising contacting the test sample with the composition of embodiment 19 or 36 and at least one detectable label.

61. The method of embodiment 60, comprising:
a. contacting the test sample with the composition of embodiment 13, wherein the composition binds to an *S. aureus* surface determinant antigen and an *S. aureus* secreted toxin polypeptide;
b. contacting the test sample with the at least one detectable label, wherein the at least one detectable label binds to the surface determinant antigen, the secreted toxin, or an antibody or antigen binding fragment thereof that is bound to the surface determinant antigen or the secreted toxin; and
c. detecting the presence of *S. aureus* in the test sample based on the signal generated by the at least one detectable label, wherein the presence of *S. aureus* is directly correlated with the signal generated by the at least one detectable label.

62. The method of embodiment 60, comprising:
a. contacting the test sample with the composition of embodiment 13, wherein the composition binds to an *S. aureus* surface determinant antigen and an *S. aureus* secreted toxin polypeptide;
b. contacting the test sample with the at least one detectable label, wherein the at least one detectable label competes with the surface determinant antigen or the secreted toxin for binding to an antibody in the composition of embodiment 13; and
c. detecting the presence of *S. aureus* in the test sample based on the signal generated by the at least one detectable label, wherein the presence of *S. aureus* is indirectly correlated with the signal generated by the at least one detectable label.

63. The method of any one of embodiments 60-62, wherein the sample is a patient sample and the method further comprises diagnosing a patient with an *S. aureus* infection.

64. The method of any one of embodiments 60-63, wherein the method is adapted for use in an automated system or a semi-automated system.

65. A method of treating an *S. aureus* infection in a patient, comprising administering the isolated antibody or antigen binding fragment thereof of any one of embodiments 1-18 or 21-35, or the composition of any one of embodiments 19, 36 or 38-54, to a patient.

66. A method for preventing or reducing the severity of *S. aureus*-associated sepsis in a patient, comprising administering the isolated antibody or antigen binding fragment thereof of any one of embodiments 1-18 or 21-35, or the composition of any one of embodiments 19, 36 or 38-54, to a patient.

67. A method of delaying the onset of sepsis associated with *S. aureus* infection in a patient, comprising administering the isolated antibody or antigen binding fragment thereof of any one of embodiments 1-18 or 21-35, or the composition of any one of embodiments 19, 36 or 38-54, to a patient.

68. A method of preventing the onset of sepsis associated with *S. aureus* infection in a patient, comprising administering the isolated antibody or antigen binding fragment thereof of any one of embodiments 1-18 or 21-35, or the composition of any one of embodiments 19, 36 or 38-54, to a patient.

69. A method of reducing *S. aureus* bacterial load in the bloodstream or heart in a patient comprising administering to said patient an effective amount of an isolated anti-the isolated antibody or antigen binding fragment thereof of any one of embodiments 1-18.

70. A method of reducing *S. aureus* bacterial agglutination and/or thromboembolic lesion formation in a patient comprising administering to said patient an effective amount of an isolated anti-the isolated antibody or antigen binding fragment thereof of any one of embodiments 1-18.

71. The method of any of embodiments 65-70, further comprising administering an antibiotic to the patient.

72. The method of embodiment 69, wherein the antibiotic is penicillin, oxacillin, flucloxacillin, or vancomycin.

What is claimed is:

1. An isolated antibody or antigen binding fragment thereof that specifically binds to the *Staphylococcus aureus* (*S. aureus*) ClfA surface determinant antigen,
   wherein the isolated antibody or antigen binding fragment thereof comprises a heavy chain variable region (VH) and a light chain variable region VL [(VH)], each of which comprises three complementarity determining regions (CDR1, CDR2, and CDR3)
   and wherein:
   a. a VH CDR1 is identical to the amino acid sequence of SEQ ID NO: 133;
   b. a VH CDR2 is identical to the amino acid sequence of SEQ ID NO: 134; and
   c. a VH CDR3 is identical to the amino acid sequence of SEQ ID NO: 135; and
   d. a VL CDR1 is identical to the amino acid sequence of SEQ ID NO: 137;
   e. a VL CDR2 is identical to the amino acid sequence of SEQ ID NO: 138; and
   f. a VL CDR3 is identical to the amino acid sequence of SEQ ID NO: 139.

2. An isolated antibody or antigen binding fragment thereof of claim 1, wherein the VH amino acid sequence is 100% identical to the amino acid sequence of SEQ ID NO: 132 and the VL amino acid sequence is 100% identical to the amino acid sequence of SEQ ID NO: 136.

3. A composition comprising the isolated antibody or antigen binding fragment thereof of claim 1, and a pharmaceutically acceptable excipient.

4. An isolated antibody or antigen binding fragment thereof that specifically binds to the *Staphylococcus aureus* (*S. aureus*) ClfA surface determinant antigen,
   wherein the isolated antibody or antigen binding fragment thereof comprises a heavy chain variable region (VH) and a light chain variable region VL [(VH)], each of which comprises three complementarity determining regions (CDR1, CDR2, and CDR3)
   and wherein:
   a. a VH CDR1 is identical to the amino acid sequence of SEQ ID NO: 141;
   b. a VH CDR2 is identical to the amino acid sequence of SEQ ID NO: 142; and
   c. a VH CDR3 is identical to the amino acid sequence of SEQ ID NO: 143; and
   d. a VL CDR1 is identical to the amino acid sequence of SEQ ID NO: 145;
   e. a VL CDR2 is identical to the amino acid sequence of SEQ ID NO: 146; and
   f. a VL CDR3 is identical to the amino acid sequence of SEQ ID NO: 147.

5. An isolated antibody or antigen binding fragment thereof of claim 4, wherein the VH amino acid sequence is identical to the amino acid sequence of SEQ ID NO: 140 and the VL amino acid sequence is identical to the amino acid sequence of SEQ ID NO: 144.

6. A composition comprising the isolated antibody or antigen binding fragment thereof of claim 4, and a pharmaceutically acceptable excipient.

* * * * *

SEQUENCE LISTING

```
<160> NUMBER OF SEQ ID NOS: 148

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Gln Ser Ile Ser Ser Trp Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ala Ser Ser Leu Glu Ser
1               5
```

```
<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Tyr Asn Ser Tyr Trp Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Gly Ile Arg Asn Asp Leu Gly
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Asp Tyr Asn Tyr Pro Trp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Tyr Asp Met His
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

Gly Ile Gly Thr Ala Gly Asp Thr Tyr Tyr Pro Ser Val Lys Gly
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Asn Tyr Ser Ser Thr Gly Gly Tyr Tyr Gly Met Asp Val
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Tyr Asp Met His
1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ile Gly Thr Asp Gly Asp Thr Tyr Tyr Pro Gly Ser Val Lys Gly
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Tyr Ser Ser Ser Asn His Tyr Asn Gly Met Asp Val
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Tyr Ala Met Thr
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ile Ser Gly Ser Gly Gly Ser Thr Tyr Tyr Ala Asp Ser Val Lys
1               5                   10                  15

Gly

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Gly Arg Gln Val Glu Asp Tyr Tyr Tyr Tyr Gly Met Asp Val
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Tyr Ser Pro Thr Gly His Tyr Met Gly Met Asp Val
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Ile Asp Thr Ala Gly Asp Thr Tyr Tyr Pro Gly Ser Val Lys Gly
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Arg Tyr Ser Gly Asn Phe His Tyr Asn Gly Met Asp Val
1               5                   10

<210> SEQ ID NO 19
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Thr Leu Ser Ala Ser Val Gly

```
                1               5                  10                 15
Asp Arg Val Thr Ile Thr Cys Arg Ala Ser Gln Ser Ile Ser Ser Trp
                20                 25                 30

Leu Ala Trp Tyr Gln Gln Lys Pro Gly Lys Ala Pro Lys Leu Leu Ile
        35                 40                 45

Tyr Lys Ala Ser Ser Leu Glu Ser Gly Val Pro Ser Arg Phe Ser Gly
    50                 55                 60

Ser Gly Ser Gly Thr Glu Phe Thr Leu Thr Ile Ser Ser Leu Gln Pro
65                 70                 75                 80

Asp Asp Phe Ala Thr Tyr Tyr Cys Gln Gln Tyr Asn Ser Tyr Trp Thr
                85                 90                 95

Phe Gly Gln Gly Thr Lys Val Glu Ile Lys
            100                105
```

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 20

```
Glu Val Gln Leu Val Glu Ser Gly Gly Leu Val Gln Pro Gly Gly
1               5                  10                 15

Ser Leu Arg Leu Ser Cys Ala Ala Ser Gly Phe Thr Phe Ser Ser Tyr
            20                 25                 30

Asp Met His Trp Val Arg Gln Ala Thr Gly Lys Gly Leu Glu Trp Val
        35                 40                 45

Ser Gly Ile Gly Thr Ala Gly Asp Thr Tyr Tyr Pro Gly Ser Val Lys
    50                 55                 60

Gly Arg Phe Thr Ile Ser Arg Glu Asn Ala Lys Asn Ser Leu Tyr Leu
65                 70                 75                 80

Gln Leu Asn Ser Leu Arg Ala Gly Asp Thr Ala Val Tyr Phe Cys Ala
                85                 90                 95

Arg Asp Asn Tyr Ser Ser Thr Gly Gly Tyr Tyr Gly Met Asp Val Trp
            100                105                110

Gly Gln Gly Thr Thr Val Thr Val Ser Ser
        115                120
```

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 21

```
Asp Ile Gln Met Thr Gln Ser Pro Ser Thr Leu Ser Ala Ser Val Gly
1               5                  10                 15

Asp Arg Val Thr Ile Thr Cys Arg Ala Ser Gln Ser Ile Ser Ser Trp
            20                 25                 30

Leu Ala Trp Tyr Gln Gln Lys Pro Gly Lys Ala Pro Lys Leu Leu Ile
        35                 40                 45

Tyr Lys Ala Ser Ser Leu Glu Ser Gly Val Pro Ser Arg Phe Ser Gly
    50                 55                 60

Ser Gly Ser Gly Thr Glu Phe Thr Leu Thr Ile Ser Ser Leu Gln Pro
```

```
                65                  70                  75                  80
Asp Asp Phe Ala Thr Tyr Tyr Cys Gln Gln Tyr Asn Ser Tyr Trp Thr
                    85                  90                  95

Phe Gly Gln Gly Thr Lys Val Glu Ile Lys
                100                 105
```

<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Thr Gly Lys Gly Leu Glu Trp Val
        35                  40                  45

Ser Val Ile Gly Thr Asp Gly Asp Thr Tyr Tyr Pro Gly Ser Val Lys
    50                  55                  60

Gly Arg Phe Ile Ile Ser Arg Glu Asn Ala Lys Asn Ser Leu Tyr Leu
65                  70                  75                  80

Glu Met Asn Ser Leu Arg Ala Gly Asp Thr Ala Val Tyr Tyr Cys Ala
                85                  90                  95

Arg Asp Arg Tyr Ser Ser Ser Asn His Tyr Asn Gly Met Asp Val Trp
            100                 105                 110

Gly Gln Gly Thr Thr Val Thr Val Ser Ser
        115                 120
```

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
                100                 105
```

<210> SEQ ID NO 24
<211> LENGTH: 122
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Thr Gly Lys Gly Leu Glu Trp Val
        35                  40                  45

Ser Val Ile Gly Thr Asp Gly Asp Thr Tyr Tyr Pro Gly Ser Val Lys
    50                  55                  60

Gly Arg Phe Ile Ile Ser Arg Glu Asn Ala Lys Asn Ser Leu Tyr Leu
65                  70                  75                  80

Glu Met Asn Ser Leu Arg Ala Gly Asp Thr Ala Val Tyr Tyr Cys Ala
                85                  90                  95

Arg Asp Arg Tyr Ser Ser Ser Asn His Tyr Asn Gly Met Asp Val Trp
            100                 105                 110

Gly Gln Gly Thr Thr Val Thr Val Ser Ser
        115                 120

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 26
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Thr Trp Val Arg Gln Ala Pro Gly Lys Gly Leu Glu Trp Val
            35                  40                  45

Ser Val Ile Ser Gly Ser Gly Gly Ser Thr Tyr Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Arg Gln Val Glu Asp Tyr Tyr Tyr Tyr Gly Met
            100                 105                 110

Asp Val Trp Gly Gln Gly Thr Thr Val Thr Val Ser Ser
            115                 120                 125

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 28
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Val Ile Asp Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95
```

Arg Asp Arg Tyr Ser Gly Asn Phe His Tyr Asn Gly Met Asp Val Trp
            100                 105                 110

Gly Gln Gly Thr Thr Val Thr Val Ser Ser
        115                 120

<210> SEQ ID NO 29
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaaactcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attggacgtt cggccaaggg     300
accaaggtgg aaatcaaa                                                   318

<210> SEQ ID NO 30
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gaggtgcagc tggtggagtc tgggggaggc ttggtacagc ctggggggtc cctgagactc      60
tcctgtgcag cctctggatt caccttcagt agctacgaca tgcactgggt ccgccaagct     120
acaggaaaag gtctggagtg ggtctcaggt attggcactg ctggtgacac atattatcca     180
ggctccgtga agggccgatt caccatctcc agagaaaatg ccaagaactc cttgtatctt     240
caattgaaca gcctgagagc cggggacacg gctgtgtact tctgtgcaag agacaattat     300
agcagcaccg gggggtacta cggtatggac gtctggggcc aagggaccac ggtcaccgtc     360
tcctca                                                                366

<210> SEQ ID NO 31
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaaactcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attggacgtt cggccaaggg     300
accaaggtgg aaatcaaa                                                   318

```
<210> SEQ ID NO 32
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gaggtgcagc tggtggagtc tgggggaggc ttggtacagc ctgggggtc cctgagactc        60 tcctgtgcag cctctggatt caccttcagt aggtacgaca tgcactgggt ccgccaagct      120
acaggaaaag gtctggagtg gtctcagtt attggtactg atggtgacac atactatcca       180
ggctccgtga agggccgatt catcatctcc agagaaaatg ccaagaactc cttgtatctt      240
gaaatgaaca gcctgagagc cggggacacg gctgtgtatt actgtgcaag agatcggtat      300
agcagctcga accactacaa cggtatggac gtctggggcc aagggaccac ggtcaccgtc      360
tcctca                                                                 366

<210> SEQ ID NO 33
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gacatccaga tgacccagtc tccttccacc ctgtctgcat ctgtaggaga cagagtcacc       60
atcacttgcc gggccagtca gagtattagt agctggttgg cctggtatca gcagaaacca     120
gggaaagccc ctaaggtcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attggacgtt cggccaaggg     300
accaaggtgg aaatcaaa                                                   318

<210> SEQ ID NO 34
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gaggtgcagc tggtggagtc tgggggaggc ttggtacagc ctgggggtc cctgagactc        60 tcctgtgcag cctctggatt caccttcagt aggtacgaca tgcactgggt ccgccaagct      120
acaggaaaag gtctggagtg gtctcagtt attggtactg atggtgacac atactatcca       180
ggctccgtga agggccgatt catcatctcc agagaaaatg ccaagaactc cttgtatctt      240
gaaatgaaca gcctgagagc cggggacacg gctgtgtatt actgtgcaag agatcggtat      300
agcagctcga accactacaa cggtatggac gtctggggcc aagggaccac ggtcaccgtc      360
tcctca                                                                 366

<210> SEQ ID NO 35
<211> LENGTH: 321
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 35

```
gccatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagctcct gatctatgat gcatccagtt tacaaagtgg ggtcccatca    180
aggttcagcg gcagtggatc tggcacagat ttcactctca ccatcagcag cctgcagcct    240
gaagattttg caacttatta ctgtctacaa gattacaatt acccgtggac gttcggccaa    300
gggaccaagg tggaaatcaa a                                              321
```

<210> SEQ ID NO 36
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
gaggtgcagc tgttggagtc tgggggaggc ttggtacagc ctggggggtc cctgagactc     60
tcctgtgcag cctctggatt cacctttagc agctatgcca tgacctgggt ccgccaggct   120
ccagggaagg ggctggaatg ggtctcagtt attagtggta gtggtggtag cacatactac   180
gcagactccg tgaagggccg gttcaccgtc tccagagaca attccaagaa cacgctgtat   240
ctgcaaatga acagcctgag agccgaggac acggccgtat attactgtgc gaaagatggg   300
aggcaggtcg aggattacta ctactactac ggtatggacg tctggggcca agggaccacg   360
gtcaccgtct cctca                                                     375
```

<210> SEQ ID NO 37
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
gacatccaga tgacccagtc tccttccacc ctgtctgcat ctgtaggaga cagagtcacc     60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attggacgtt cggccaaggg   300
accaaggtgg aaatcaaa                                                  318
```

<210> SEQ ID NO 38
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
gaggtgcagc tgttggagtc tgggggaggc ttggtacagc ctggggggtc cctgagactc     60
tcctgtacag cctctggatt cacctttcagt agttacgaca tgcactgggt ccgccaagct   120
```

```
acaggaaaag gtctggagtg ggtctcagtt attgatactg ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgtaag agataggtat    300
agtgggaact ccactacaa cggtatggac gtctggggcc aagggaccac ggtcaccgtc     360
tcctca                                                                366
```

<210> SEQ ID NO 39
<211> LENGTH: 293
<212> TYPE: PRT
<213> ORGANISM: Staphylococcus aureus

<400> SEQUENCE: 39

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 40
<211> LENGTH: 293
<212> TYPE: PRT

<213> ORGANISM: Staphylococcus aureus

<400> SEQUENCE: 40

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val 35                  40                  45
Ser Gly Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Arg Tyr Ser Pro Thr Gly His Tyr Met Gly Met Asp Val Trp
            100                 105                 110

Gly Gln Gly Thr Thr Val Thr Val Ser Ser
            115                 120

<210> SEQ ID NO 42
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Tyr Trp Thr
                 85                  90                  95

Phe Gly Gln Gly Thr Lys Val Glu Ile Lys
            100                 105

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Asp Met His Trp Val Arg Gln Ala Thr Gly Lys Gly Leu Glu Trp Val
             35                  40                  45

Ser Gly Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Arg Tyr Ser Arg Thr Gly His Tyr Met Gly Met Asp Val Trp

```
                100                 105                 110
Gly Gln Gly Thr Thr Val Thr Val Ser Ser
        115                 120

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 45
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Arg Thr Gly His Tyr Met Gly Met Ser Leu Trp
            100                 105                 110

Gly Gln Gly Thr Thr Val Thr Val Ser Ser
        115                 120

<210> SEQ ID NO 46
<211> LENGTH: 106
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 46

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Arg Thr Gly His Tyr Met Gly Met Asp Val Trp
            100                 105                 110

Gly Gln Gly Thr Thr Val Thr Val Ser Ser
        115                 120

<210> SEQ ID NO 48
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 49
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Arg Thr Gly His Tyr Met Gly Met Asp Val Trp
            100                 105                 110

Gly Gln Gly Thr Thr Val Thr Val Ser Ser
        115                 120

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 51
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Met Gly Met Ser Leu Trp
            100                 105                 110

Gly Gln Gly Thr Thr Val Thr Val Ser Ser
        115                 120

<210> SEQ ID NO 52
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 53
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
            85                  90                  95

Arg Asp Arg Tyr Ser Arg Thr Gly His Tyr Met Gly Met Asp Val Trp
            100                 105                 110

Gly Gln Gly Thr Thr Val Thr Val Ser Ser
            115                 120

<210> SEQ ID NO 54
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
            85                  90                  95

Phe Gly Gln Gly Thr Lys Val Glu Ile Lys
            100                 105

<210> SEQ ID NO 55
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60
```

```
Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Asn Tyr Ser Ser Thr Gly Gly Tyr Tyr Gly Met Asp Val Trp
            100                 105                 110

Gly Gln Gly Thr Thr Val Thr Val Ser Ser
            115                 120
```

```
<210> SEQ ID NO 56
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Trp Thr
                 85                  90                  95

Phe Gly Gln Gly Thr Lys Val Glu Ile Lys
            100                 105
```

```
<210> SEQ ID NO 57
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser His
             20                  25                  30

Asp Met His Trp Val Arg Gln Ala Thr Gly Lys Gly Leu Glu Trp Val
         35                  40                  45

Ser Gly Ile Gly Thr Ala Gly Asp Thr Tyr Tyr Pro Asp Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
            115                 120
```

<210> SEQ ID NO 58
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 59
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Pro Thr Gly Gly Tyr Tyr Gly Met Asp Val Trp
            100                 105                 110

Gly Gln Gly Thr Thr Val Thr Val Ser Ser
        115                 120

<210> SEQ ID NO 60
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Thr Leu Ser Ala Ser Val Gly

-continued

```
              1               5                  10                 15
Asp Arg Val Thr Ile Thr Cys Arg Ala Ser Gln Ser Ile Ser Ser Trp
              20                 25                 30

Leu Ala Trp Tyr Gln Gln Lys Pro Gly Lys Ala Pro Lys Leu Leu Ile
              35                 40                 45

Tyr Lys Ala Ser Ser Leu Lys Ser Gly Val Pro Ser Arg Phe Ser Gly
     50                 55                 60

Ser Gly Ser Gly Thr Glu Phe Thr Leu Thr Ile Ser Ser Leu Gln Pro
65                 70                 75                 80

Asp Asp Phe Ala Thr Tyr Tyr Cys Gln Gln Tyr Glu Ser Tyr Trp Thr
                 85                 90                 95

Phe Gly Gln Gly Thr Lys Val Glu Ile Lys
                 100                105
```

<210> SEQ ID NO 61
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Ser Ser His
              20                 25                 30

Asp Met His Trp Val Arg Gln Ala Thr Gly Lys Gly Leu Glu Trp Val
              35                 40                 45

Ser Gly Ile Gly Thr Arg Gly Asp Thr Tyr Tyr Pro Asp Ser Val Lys
     50                 55                 60

Gly Arg Phe Thr Ile Ser Arg Glu Asn Ala Lys Asn Ser Leu Tyr Leu
65                 70                 75                 80

Gln Met Asn Ser Leu Arg Ala Gly Asp Thr Ala Val Tyr Tyr Cys Ala
                 85                 90                 95

Arg Asp Arg Tyr Ser Pro Thr Gly His Tyr Tyr Gly Met Asp Val Trp
                 100                105                110

Gly Gln Gly Thr Thr Val Thr Val Ser Ser
        115                120
```

<210> SEQ ID NO 62
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Ser Ser His
              20                 25                 30

Asp Met His Trp Val Arg Gln Ala Thr Gly Lys Gly Leu Glu Trp Val
              35                 40                 45

Ser Gly Ile Gly Thr Arg Gly Asp Thr Tyr Tyr Pro Asp Ser Val Lys
     50                 55                 60

Gly Arg Phe Thr Ile Ser Arg Glu Asn Ala Lys Asn Ser Leu Tyr Leu
```

```
                65                  70                  75                  80
Gln Met Asn Ser Leu Arg Ala Gly Asp Thr Ala Val Tyr Tyr Cys Ala
                    85                  90                  95

Arg Asp Lys Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 63
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Val Lys Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Trp Thr
                85                  90                  95

Phe Gly Gln Gly Thr Lys Val Glu Ile Lys
            100                 105

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Gln Tyr Asp Thr Tyr Trp Thr
1               5

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Arg Tyr Ser Arg Thr Gly His Tyr Met Gly Met Asp Val
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 66

Asp Arg Tyr Ser Arg Thr Gly His Tyr Met Gly Met Ser Leu
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Asn Tyr Ser Arg Thr Gly His Tyr Met Gly Met Asp Val
1               5                   10

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gln Tyr Ala Asp Tyr Trp Thr
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser His Asp Met His
1               5

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ile Gly Thr Ala Gly Asp Thr Tyr Tyr Pro Asp Ser Val Lys Gly
1               5                   10                  15

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Arg Tyr Ser Pro Thr Gly His Tyr Tyr Gly Met Asp Val
1               5                   10

<210> SEQ ID NO 72
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Asn Tyr Ser Pro Thr Gly Gly Tyr Tyr Gly Met Asp Val
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Ala Ser Ser Leu Lys Ser
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Tyr Glu Ser Tyr Trp Thr
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ile Gly Thr Arg Gly Asp Thr Tyr Tyr Pro Asp Ser Val Lys Gly
1               5                   10                  15

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Lys Tyr Ser Pro Thr Gly His Tyr Tyr Gly Met Asp Val
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Ala Ser Ser Leu Val Lys
```

```
<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Arg Tyr Ser Pro Thr Gly His Tyr Met Gly Met Ser Leu
1               5                   10

<210> SEQ ID NO 79
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 80
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Met Met Gln Trp Val Arg Gln Ala Pro Gly Lys Gly Leu Glu Trp Val
        35                  40                  45

Ser Ser Ile Trp Pro Ser Gly Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

Ala Arg Val Arg Arg Gly Gly Ala Thr Asp Tyr Trp Gly Gln Gly Thr
            100                 105                 110

Leu Val Thr Val Ser Ser
        115

<210> SEQ ID NO 81
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Gly Trp Tyr Gln Gln Lys Pro Gly Gln Ala Pro Arg Leu Leu Ile
        35                  40                  45

Tyr Gly Ala Ser Thr Arg Ala Thr Gly Ile Pro Thr Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Thr Tyr Tyr Cys Gln Gln Tyr Gln Asn Trp Pro Leu
                85                  90                  95

Leu Thr Phe Gly Gly Gly Thr Lys Val Glu Ile Lys
            100                 105

<210> SEQ ID NO 82
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Trp Trp Val Arg Gln Ala Pro Gly Lys Gly Leu Glu Trp Val
        35                  40                  45

Ser Val Ile Gly Pro Ser Gly Gly Pro Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gly Arg Tyr Ser Val Phe Glu Thr Trp Gly Gln Gly
            100                 105                 110

Thr Met Val Thr Val Ser Ser
        115

<210> SEQ ID NO 83
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Gln Met Thr Gln Ser Pro Ala Thr Leu Ser Val Ser Pro Gly
1               5                   10                  15

Gly Arg Ala Thr Leu Ser Cys Arg Ala Ser Gln Ser Val Arg Lys Asn
            20                  25                  30

Val Ala Trp Tyr Gln Gln Lys Pro Gly Gln Pro Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Thr Glu Phe Thr Leu Thr Ile Ser Arg Met Gln Pro
65                  70                  75                  80

Glu Asp Phe Val Val Tyr His Cys Gln Gln Tyr Ser Ser Trp Pro Ala
                85                  90                  95

Phe Gly Gln Gly Thr Met Val Glu Ile Asn
            100                 105

<210> SEQ ID NO 84
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Phe Met Gly Trp Val Arg Gln Ala Pro Gly Lys Gly Leu Glu Trp Val
        35                  40                  45

Ser Ser Ile Tyr Ser Ser Gly Gly Tyr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Trp Arg Asp Gly Thr Phe Asp Tyr Trp Gly Gln Gly Thr
            100                 105                 110

Leu Val Thr Val Ser Ser
        115

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ile Gln Met Thr Gln Ser Pro Ser Ser Leu Ser Ala Ser Ile Gly
1               5                   10                  15

Asp Arg Val Thr Ile Ser Cys Arg Ala Ser Gln Ser Val Arg Glu Tyr
            20                  25                  30

Leu Asn Trp Tyr Gln Gln Lys Pro Gly Lys Ala Pro Lys Leu Leu Ile
                35                  40                  45

Phe Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Arg Phe
                85                  90                  95

Thr Phe Gly Pro Gly Thr Lys Val Asp Ile Lys
            100                 105

<210> SEQ ID NO 86
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Pro Ile Ser Trp Val Arg Gln Ala Pro Gly Gln Gly Leu Glu Trp Met
            35                  40                  45

Gly Lys Ile Ile Pro Ile Phe Gly Thr Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Ser Pro Asn Arg Pro Tyr Asn Ile Gly Trp His Tyr Tyr Phe Asp
            100                 105                 110

Tyr Trp Gly Lys Gly Thr Leu Val Thr Val Ser Ser
        115                 120

<210> SEQ ID NO 87
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Gly Ser Lys Arg Pro Ser Gly Val Ser Asn Arg Phe
        50                  55                  60

Ser Gly Ser Arg Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Thr Val Leu
            100                 105                 110

<210> SEQ ID NO 88
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asp Glu Gly Arg Ala Asn Asn Trp Trp Ile Pro Pro
            100                 105                 110

Gly Gly Arg Trp Gly Gln Gly Thr Met Val Thr Val Ser Ser
        115                 120                 125

<210> SEQ ID NO 89
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ser Ser Glu Leu Thr Gln Asp Pro Thr Leu Ser Val Ala Leu Gly Gln
1               5                   10                  15

Thr Val Arg Ile Thr Cys Gln Gly Asp Ser Leu Arg Arg Ser Phe Ala
            20                  25                  30

Ser Trp Tyr Gln Lys Lys Pro Gly Gln Ala Pro Val Leu Leu Ile Tyr
        35                  40                  45

Gly Gln Asn Lys Arg Pro Ala Gly Ile Pro Asp Arg Phe Ser Gly Ser
    50                  55                  60

Arg Ser Gly Asn Ser Ala Ser Leu Thr Ile Thr Gly Ala Gln Ala Glu
65                  70                  75                  80

Asp Glu Ala Asp Tyr Tyr Cys Asn Ser Arg Asp Ala Arg Leu Asn Pro
                85                  90                  95

Tyr Ile Leu Phe Gly Gly Gly Thr Lys Leu Thr Val Leu
            100                 105

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 90

Pro Tyr Met Met Gln
1               5

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Ile Trp Pro Ser Gly Gly Lys Thr Tyr Tyr Ala Asp Ser Val Lys
1               5                   10                  15
Gly

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Arg Arg Gly Gly Ala Thr Asp Tyr
1               5

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Ala Ser Gln Ser Val Ser Ser Asn Leu Gly
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ala Ser Thr Arg Ala Thr
1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Tyr Gln Asn Trp Pro Leu Leu Thr
1               5                   10

<210> SEQ ID NO 96
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asn Tyr Tyr Met Trp
1               5

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Val Ile Gly Pro Ser Gly Gly Pro Thr Gln Tyr Ala Asp Ser Val Lys
1               5                   10                  15

Gly

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Gly Gly Arg Tyr Ser Val Phe Glu Thr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Ser Gln Ser Val Arg Lys Asn Val Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Ala Ser Thr Arg Ala Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 101

Gln Gln Tyr Ser Ser Trp Pro Ala Phe
1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Tyr Phe Met Gly
1               5

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Ile Tyr Ser Ser Gly Gly Tyr Thr Ser Tyr Ala Asp Ser Val Lys
1               5                   10                  15

Gly

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Trp Arg Asp Gly Thr Phe Asp Tyr
1               5

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ala Ser Gln Ser Val Arg Glu Tyr Leu Asn
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Ala Ser Ser Leu Gln Ser
1               5

<210> SEQ ID NO 107
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gln Ser Tyr Ser Thr Arg Phe Thr
1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Tyr Pro Ile Ser
1               5

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Lys Ile Ile Pro Ile Phe Gly Thr Thr Asn Tyr Ala Gln Lys Phe Gln
1               5                   10                  15

Gly

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Asn Arg Pro Tyr Asn Ile Gly Trp His Tyr Tyr Phe Asp Tyr
1               5                   10                  15

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Gly Thr Ser Ser Asp Val Gly Gly Tyr Asn Tyr Val Ser
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 112

Glu Gly Ser Lys Arg Pro Ser
1               5

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Ser Tyr Thr Thr Arg Ser Thr Arg Val
1               5                   10

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Tyr Ala Met Ser
1               5

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Ile Ser Gly Ser Gly Gly Ser Thr Tyr Tyr Ala Asp Ser Val Lys
1               5                   10                  15

Gly

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Gln Asp Glu Gly Arg Ala Asn Asn Trp Trp Ile Pro Pro Gly Gly
1               5                   10                  15

Arg

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gly Asp Ser Leu Arg Arg Ser Phe Ala Ser
1               5                   10
```

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gln Asn Lys Arg Pro Ala
1               5

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asn Ser Arg Asp Ala Arg Leu Asn Pro Tyr Ile Leu
1               5                   10

<210> SEQ ID NO 120
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
gaagttcaat tgttagagtc tggtggcggt cttgttcagc ctggtggttc tttacgtctt      60
tcttgcgctg cttccggatt cactttctct ccttacatga tgcagtgggt tcgccaagct     120
cctggtaaag gtttggagtg gtttcttcta atctggcctt ctggtggcaa gacttattat     180
gctgactccg ttaaaggtcg cttcactatc tctagagaca actctaagaa tactctctac     240
ttgcagatga acagcttaag ggctgaggac acggccgtgt attactgtgc gagagtgcgg     300
agggggggag ctactgacta ctggggccag ggaaccctgg tcaccgtctc aagc           354

<210> SEQ ID NO 121
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gacatccaga tgacccagtc tccagccacc ctgtctgtgt ctccagggga aagagccacc      60
ctctcctgca gggccagtca gagtgttagc agcaacttag ctggtacca gcagaaacct     120 ggccaggctc ccaggctcct catctatggt gcatccacca gggccactgg tatcccaacc     180
aggttcagtg gcagtgggtc tgggacagag ttcactctca ccatcagcag cctgcagtct     240
gaagattttg caacttatta ctgtcagcag tatcagaact ggcccttgct cactttcggc     300
ggagggacca aggtggaaat caaa                                           324

<210> SEQ ID NO 122
<211> LENGTH: 357
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 122
gaagttcaat tgttagagtc tggtggcggt cttgttcagc ctggtggttc tttacgtctt      60
tcttgcgctg cttccggatt cactttctct aattactata tgtggtgggt tcgccaagct     120
cctggtaaag gtttggagtg ggtttctgtt atcggtcctt ctggtggccc tactcagtat     180
gctgactccg ttaaaggtcg cttcactatc tctagagaca actctaagaa tactctctac     240
ttgcagatga acagcttaag ggctgaggac acggccgtgt attactgtgc gagatggggt     300
gggaggtact ctgtatttga aacctggggc caagggacaa tggtcaccgt ctcaagc        357

<210> SEQ ID NO 123
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
gacatccaga tgacccagtc tccagccact ctgtctgtgt ctccagggga agagccacc       60 ctctcctgca gggccagtca gagtgttaga aaaaacgtag cctggtatca gcagaaacct    120
ggccagcctc ccaggctcct catctatggt gcatccacca gggccactgg tgtcccagcc    180
aggttcagtg gcagtgggtc tgggacagag ttcactctca ccatcagcag gatgcagcct    240
gaagattttg tagtttatca ctgtcagcag tatagtagct ggccggcgtt cggccagggg    300
accatggtgg aaatcaac                                                  318

<210> SEQ ID NO 124
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gaagttcaat tgttagagtc tggtggcggt cttgttcagc ctggtggttc tttacgtctt      60
tcttgcgctg cttccggatt cactttctct cgttacttta tgggttgggt tcgccaagct     120
cctggtaaag gtttggagtg ggtttcttct atctattctt ctggtggcta tacttcttat     180
gctgactccg ttaaaggtcg cttcactatc tctagagaca actctaagaa tactctctac     240
ttgcagatga acagcttaag ggctgaggac acggccgtgt attactgtgc gagacggtgg     300
cgagatggca cctttgacta ctggggccag ggaaccctgg tcaccgtctc aagc           354

<210> SEQ ID NO 125
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gacatccaga tgacccagtc tccatcctcc ctgtctgcat ctattggaga cagagtcacc      60
atctcttgcc gggcaagtca gagcgttaga gagtatctaa attggtatca acaaaaacca    120
```

| | |
|---|---|
| gggaaagccc ctaaactcct gatctttgct gcatccagtt tgcagagtgg ggtcccatca | 180 |
| agattcagtg gcagtggatc tgggacagat ttcactctca ccatcagcag tctgcaacct | 240 |
| gaagattttg caacttatta ctgtcaacag agttacagta cccgattcac tttcggccct | 300 |
| gggaccaaag tggacatcaa a | 321 |

<210> SEQ ID NO 126
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

| | |
|---|---|
| caggtacagc tgcagcagtc aggggctgag gtgaagaagc ctgggtcctc ggtgaaggtc | 60 |
| tcctgcaagg cttctggagg caccttcagc agctatccta tcagctgggt gcgacaggcc | 120 |
| cctggacaag gcttgagtg gatgggaaag atcatcccta tctttggtac aacaaactac | 180 |
| gcgcagaagt tccagggcag agtcacgatt accgcggacg aatccacgag cactgcctac | 240 |
| atggaactga gcagcctgag atctgaggac acggccatat attactgtgc gagccccaat | 300 |
| cgaccctata acattggctg gcactactac tttgactact ggggcaaagg aaccctggtc | 360 |
| accgtctcct ca | 372 |

<210> SEQ ID NO 127
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

| | |
|---|---|
| cagtctgtgc tgactcagcc tgcctccgtg tctgggtctc ctggacagtc gatcaccatc | 60 |
| tcctgcactg gaaccagcag tgacgttggt ggttataact atgtctcctg gtaccaacaa | 120 |
| cacccaggca aagcccccaa actcatgatt tatgagggca gtaagcggcc ctcagggg tt | 180 |
| tctaatcgct tctctggctc caggtctggc aacacggcct ccctgacaat ctctgggctc | 240 |
| caggctgagg acgaggctga ttattactgc agctcatata caaccaggag cactcgagtc | 300 |
| ttcggcggag ggaccaagct gaccgtccta | 330 |

<210> SEQ ID NO 128
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

| | |
|---|---|
| gaggtgcagc tgttggagtc tgggggaggc ttggtacagc ctggggggtc cctgagactc | 60 |
| tcctgtgcag cctctggatt cacctttagc agctatgcca tgagctgggt ccgccaggct | 120 |
| ccagggaagg gctggagtg gtctcagct attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtgt attactgtgc aagagatcag | 300 |
| gacgaaggta gagcgaacaa ctggtggatc cccccgggg gtcgctgggg ccaggggaca | 360 |

```
atggtcaccg tctcgagt                                                      378
```

<210> SEQ ID NO 129
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
tcttctgagc tgactcagga ccctactctg tctgtggccc tgggacagac agtcagaatc    60
acatgccaag agacagcct ccgaagatct tttgcaagtt ggtaccagaa gaagccagga    120
caggcccctg tacttctcat ctatggtcaa aataagcggc cgcagggat cccagaccga    180 ttctctggct ccaggtcagg aaactcagct tcgttgacca tcacagggc tcaggcggaa    240 gatgaggctg actattactg taattcccgc gacgccagac ttaacccta tatactcttc    300 ggcggtggga ccaagctgac cgtccta                                        327
```

<210> SEQ ID NO 130
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
```

```
225                 230                 235                 240

Gly Gly Pro Ser Val Phe Leu Phe Pro Pro Lys Pro Lys Asp Thr Leu
            245                 250                 255

Tyr Ile Thr Arg Glu Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 131
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
            85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu
    210

<210> SEQ ID NO 132
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Val Glu Ser Gly Gly Gly Val Val Gln Pro Gly Arg
1               5                   10                  15

Ser Leu Arg Leu Ser Cys Ala Ala Ser Val Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Phe Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Gly Tyr Tyr Tyr Tyr Gly Met Asp Val Trp
            100                 105                 110

Gly Gln Gly Thr Thr Val Thr Val Ser Ser
        115                 120

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Tyr Gly Met His
1               5

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Leu Ile Trp Phe Asp Gly Ser Asn Glu Tyr Tyr Ala Asp Ser Val Lys
```

```
1               5                   10                  15
Gly

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Gly Gly Gly Tyr Tyr Tyr Tyr Gly Met Asp Val
1               5                   10

<210> SEQ ID NO 136
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Ala Ser Gln Gly Ile Arg Asn Asp Leu Gly
1               5                   10

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ala Ser Ser Leu Gln Ser
1               5
```

```
<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Leu Gln His Asn Ser Tyr Pro Tyr Thr
1               5

<210> SEQ ID NO 140
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Tyr
            20                  25                  30

Gly Ile Ser Trp Val Arg Gln Ala Pro Gly Gln Gly His Glu Trp Met
        35                  40                  45

Gly Trp Ile Ser Ser Tyr Asn Gly Asn Thr Asn Tyr Ala Gln Lys Leu
    50                  55                  60

Gln Gly Arg Val Thr Met Thr Ser Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ile Ala Ala Arg Gly Tyr Tyr Tyr Gly Met Asp Val Trp Gly
            100                 105                 110

Gln Gly Thr Thr Val Thr Val Ser Ser
        115                 120

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Tyr Gly Ile Ser
1               5

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Trp Ile Ser Ser Tyr Asn Gly Asn Thr Asn Tyr Ala Gln Lys Leu Gln
1               5                   10                  15

Gly
```

```
<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Ala Arg Gly Tyr Tyr Tyr Gly Met Asp
1               5                   10

<210> SEQ ID NO 144
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Arg Ala Ser Gln Ser Ile Ser Gly Ser Tyr Leu Ala
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Ala Ser Ser Arg Ala Thr
1               5

<210> SEQ ID NO 147
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 147

Gln Gln Tyr Ser Ser Trp Pro Ala Phe
1               5

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Val Ile Asp Thr Ala Gly Asp Thr Tyr Tyr Pro Gly Ser Val Lys
1               5                   10                  15

Gly
```